United States Patent
Hantash et al.

(10) Patent No.: US 11,466,325 B2
(45) Date of Patent: Oct. 11, 2022

(54) METHOD TO DETECT REPEAT SEQUENCE MOTIFS IN NUCLEIC ACID

(71) Applicant: Quest Diagnostics Investments LLC, Secaucus, NJ (US)

(72) Inventors: Feras Hantash, Mission Viejo, CA (US); Weimin Sun, Irvine, CA (US); David C. Tsao, Hacienda Heights, CA (US); Dana Marie Root, Orange, CA (US); Charles M Strom, San Clemente, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 76 days.

(21) Appl. No.: 16/357,247

(22) Filed: Mar. 18, 2019

(65) Prior Publication Data

US 2019/0376138 A1 Dec. 12, 2019

Related U.S. Application Data

(60) Division of application No. 15/174,038, filed on Jun. 6, 2016, now Pat. No. 10,233,497, which is a
(Continued)

(51) Int. Cl.
*C12Q 1/68* (2018.01)
*C07H 21/04* (2006.01)
(Continued)

(52) U.S. Cl.
CPC ........... *C12Q 1/6883* (2013.01); *C12Q 1/683* (2013.01); *C12Q 1/6827* (2013.01);
(Continued)

(58) Field of Classification Search
None
See application file for complete search history.

(56) References Cited

U.S. PATENT DOCUMENTS 5,474,796 A * 12/1995 Brennan .............. B01J 19/0046
422/547
6,090,558 A * 7/2000 Butler .................. C12Q 1/6858
435/6.11
(Continued)

FOREIGN PATENT DOCUMENTS

WO WO 2010/110835 A1 9/2010
WO WO 2011/006165 1/2011
WO WO 2011/046518 A1 4/2011

OTHER PUBLICATIONS

Tassone et al. (J. of Molecular Diagnostics, vol. 10, No. 1, pp. 43-49, Jan. 2008).*
(Continued)

*Primary Examiner* — Jeanine A Goldberg
(74) *Attorney, Agent, or Firm* — Foley & Lardner LLP

(57) ABSTRACT

Methods for determining the presence or absence of expansion of CGG repeat sequence in the FMR1 gene presence or absence of expansion of CCG repeat sequence in the FMR2 gene are provided. The methods are useful in identifying an individual with normal/intermediate, versus premutation or full mutation allele of FMR1 gene and FMR2 gene due to the expansion of CGG repeats and CCG repeats in the 5'-untranslated region respectively. The methods are also useful for screening newborns for fragile X syndrome or for screening women to determine heterozygosity status with full premutation of the CCG repeat tract. The methods are also useful in estimating the premutation and full mutation carrier frequency and estimating the prevalence of FXTAS AND FXPOI in a population. The methods are simple, rapid and require small amount of sample.

5 Claims, 25 Drawing Sheets

Specification includes a Sequence Listing.

Related U.S. Application Data continuation of application No. 13/576,840, filed as application No. PCT/US2011/023777 on Feb. 4, 2011, now Pat. No. 9,382,586.

(60) Provisional application No. 61/302,059, filed on Feb. 5, 2010.

(51) Int. Cl.
  *C12Q 1/6883* (2018.01)
  *C12Q 1/6827* (2018.01)
  *C12Q 1/683* (2018.01)
  *C12Q 1/6858* (2018.01)
  *G16B 25/20* (2019.01)
  *G16B 99/00* (2019.01)

(52) U.S. Cl.
  CPC .......... *C12Q 1/6858* (2013.01); *G16B 25/20* (2019.02); *C12Q 2600/154* (2013.01); *C12Q 2600/156* (2013.01); *C12Q 2600/158* (2013.01); *C12Q 2600/16* (2013.01); *G16B 99/00* (2019.02)

(56) References Cited

U.S. PATENT DOCUMENTS

| | | | |
|---|---|---|---|
| 2002/0187475 | A1 | 12/2002 | Coticone et al. |
| 2003/0190645 | A1* | 10/2003 | Van Eijk ............. C12Q 1/6858 435/6.12 |
| 2004/0072159 | A1 | 4/2004 | Takaiwa et al. |
| 2005/0191636 | A1 | 9/2005 | Hahn |
| 2007/0178445 | A1 | 8/2007 | Eshleman et al. |
| 2007/0178491 | A1 | 8/2007 | Park et al. |
| 2008/0113355 | A1 | 5/2008 | Hagerman et al. |
| 2008/0124709 | A1 | 5/2008 | Huang et al. |

OTHER PUBLICATIONS

NEB catalog (1998/1999), pp. 121, 284. (Year: 1998).*
Rothstein et al. (1994) PNAS USA 91: 4155-4159. (Year: 1994).*
Extended European Search Report and Opinion in EP 18188881.9, dated Jan. 21, 2019, 6 pages.
Hantash, F.M., et al., "Qualitative assessment of FMR1 (CGG)n triplet repeat status in normal, intermediate, premutation, full mutation, and mosaic carriers in both sexes: Implications for fragile X syndrome carrier and newborn screening", Genetics in Medicine, Feb. 17, 2010, 12(3):162-173.
Wang, Q., et al., "A rapid, non-radioactive screening test for fragile X mutations at the FRAXA and FRAXE loci", J Med Genet, Mar. 1, 1995, 32(3): 170-173.
Rousseau et al., "Prevalence of Carriers of Premutations-Size-Alleles of the FMRI Gene—Implications for the Population Genetics of the Fragile X Syndrome," Am. J. Hum. Genet., vol. 57, pp. 1006-1018, 1995.
Hagerman et al., "Advances in the Treatment of Fragile X Syndrome," Pediatrics, vol. 123, No. 1, pp. 378-390, Jan. 2009.
International Search Report issued in application No. PCT/US11/23777 dated Jul. 29, 2011.
Tassone et al., "A Rapid Polymerase Chain Reaction-Based Screening Method for Identification of All Expanded Alleles of the Fragile X (FMR1) Gene in Newborn and High-Risk Populations," Journal of Molecular Diagnostics, vol. 10, No. 1, pp. 43-40, Jan. 1, 2008.
European Search Report issued in application No. EP 11 74 0443 dated Aug. 28, 2013.
Mc Conlogue et al., "Structure-independent DNA amplification by PCR using 7-deaza-2'-deoxyguanosine," Nucleic Acids Research, vol. 16, No. 20, p. 9869, 1988.
Larsen et al., "High-throughput analysis of Fragile X $(CGG)_n$ alleles in the normal and permutation range by PCR amplification and automated capillary electrophoresis," Human Genetics, vol. 100, pp. 564-568, 1997.
Filipovic-Sadic et al., "A Novel FMR1 PCR Method for the Routine Detection of Low-Abundunce Expanded Alleles and Full Mutations in Fragile X Syndrome," Clinical Chemistry, vol. 56, No. 3, pp. 1-10, 2010.
Lyon et al., "A Simple, High-Throughput Assay for Fragile X Expanded Alleles Using Triple Retreat Primed PCR and Capillary Electronphoresis," Journal of Molecular Diagnostics, vol. 12, No. 4, pp. 1-7, Jul. 2010.
Office Action dated Jun. 24, 2014 in U.S. Appl. No. 13/576,740.
Office Action dated Oct. 14, 2014 in U.S. Appl. No. 13/576,740.
Office Action dated Apr. 1, 2015 in U.S. Appl. No. 13/576,740.
Office Action dated Jul. 23, 2015 in U.S. Appl. No. 13/576,740.
Office Action dated Dec. 11, 2015 in U.S. Appl. No. 13/576,740.
Notice of Allowance dated Mar. 7, 2016 in U.S. Appl. No. 13/576,740.
Zhou et al., "Simplified molecular diagnosis of fragile X syndrome by fluorescent methylation-specific PCR and GeneScan analysis," Clinical Chemistry, vol. 52, No. 8, pp. 1492-1500, Aug. 2006.
European Search Report dated Jun. 16, 2016 in application No. EP 16151944.
Geez et al., Genomics, 1997, 44:201-213.
Larsen et al., Human Genetics, 1997, 100:564-568.

* cited by examiner

FIG. 1  (SEQ ID NO:1)

```
13081 aatccatgtc ccttaaaggg cacaggtgt ctccacaggg ccgcccaaaa tctggtgaga
13141 gagggcgtag acgcctcacc ttctgcctct acgggtcaca aaagcctggg tcaccctggt
13201 tgccactgtt cctagttcaa agtcttcttc tgtctaatcc ttcacccta ttctcgcctt
13261 ccactccacc tcccgctcag tcagactgcg ctactttgaa ccggaccaaa ccaaaccaaa
13321 ccaaaccaaa ccaaaccaga ccagacaccc cctcccgcgg aatcccagag aggccgaact
13381 gggataaccg gatgcatttg atttcccacg ccactgagtg cacctctgca gaaatgggcg
13441 ttctggccct cgcgaggcag tgcgacctgt caccgccctt cagccttccc gccctccacc
13501 aagcccgcgc acgcccggcc cgcgcgtctg tctttcgacc cggcaccccg gccggttccc
13561 agcagcgcgc atgcgcgcgc tcccaggcca cttgaagaga gagggcgggg ccgagggggct
13621 gagcccgcgg ggggagggaa cagcgttgat cacgtgacgt ggtttcagtg tttacacccg
13681 cagcgggccg ggggttcggc ctcagtcagg cgctcagctc cgtttcggtt tcacttccgg
13741 tggagggccg cctctgagcg ggcggcgggc cgacggcgag cgcgggcggc ggcggtgacg
13801 gaggcgccgc tgccaggggg cgtgcggcag cgcggcggcg gcggcggcgg cggcggcggc
13861 ggaggcggcg gcggcggcgg cggcggcggc ggctgggcct cgagcgcccg cagcccacct
13921 ctcgggggcg ggctcccggc gctagcaggg ctgaagagaa gatggaggag ctggtggtgg
13981 aagtgcgggg ctccaatggc gctttctaca aggtacttgg ctctagggca ggccccatct
14041 tcgcccttcc ttccctccct tttcttcttg gtgtcggcgg gaggcaggcc cggggccctc
14101 ttcccgagca ccgcgcctgg gtgccagggc acgctcggcg ggatgttgtt gggagggaag
14161 gactggactt ggggcctgtt ggaagcccct ctccgactcc gagaggccct agcgcctatc
14221 gaaatgagag accagcgagg agagggttct ctttcggcgc cgagcccgc cggggtgagc
14281 tggggatggg cgagggccgg cggcaggtac tagagccggg cgggaagggc cgaaatcggc
14341 gctaagtgac ggcgatggct tattcccct ttcctaaaca tcatctccca gcgggatccg
14401 ggcctgtcgt gtgggtagtt gtggaggagc gggggcgct tcagccgggc cgcctcctgc
14461 agcgccaaga gggcttcagg tctcctttgg cttctctttt ccggtctagc attgggactt
14521 cggagagctc cactgttctg ggcgagggct gtgaagaaag agtagtaaga agcggtagtc
14581 ggcaccaaat cacaatggca actgatttt agtggcttct ctttgtggat tcggaggag
14641 attttagatc caaaagtttc aggaagaccc taacatggcc cagcagtgca ttgaagaagt
14701 tgatcatcgt gaatattcgc gtccccttt ttgttaaacg ggtaaattc aggaatgcac
14761 atgcttcagc gtctaaaacc attagcagcg ctgctactta aaaattgtgt gtgtgtgttt
14821 aagtttccaa agacctaaat atatgccatg aaacttcagg taattaactg agagtatatt
14881 attactaggg catttttttt ttaactgagc gaaaatattt ttgtgcccct aagaacttga
14941 ccacatttcc tttgaatttg tggtgttgca gtggactgaa ttgttgaggc tttatatagg
15001 cattcatggg tttactgtgc ttttaaagt tacaccattg cagatcaact aacacctttc
15061 agttttaaaa ggaagattta caatttgat gtagcagtag tgcgtttgtt ggtatgtagg
15121 tgctgtataa attcatctat aaattctcat ttccttttga atgtctataa cctcttcaa
15181 taatatccca ccttactaca gtattttggc aatagaaggt gcgtgtggaa ggaaggctgg
15241 aaaatagcta ttagcagtgt ccaacacaat tcttaaatgt attgtagaat ggcttgaatg
15301 tttcagacag gacacgtttg gctataggaa aataaacaat tgactttatt ctgtgtttac
15361 caatttatg aagacatttg gagatcagta tatttcataa atgagtaaag tatgtaaact
15421 gttccatact ttgagcacaa agataaagcc ttttgctgta aaaggaggca aaggtaacc
15481 ccgcgtttat gttcttaaca gtctcatgaa tatgaaattg tttcagttga ctctgcagtc
15541 aaaattttaa tttcattgat tttattgatc cataatttct tctggtgagt ttgcgtagaa
15601 tcgttcacgg tcctagatta gtggttttgg tcactagatt tctggcacta ataactataa
15661 tacatataca tatatatgtg tgagtaacgg ctaatggtta ggcaagattt tgattgacct
15721 gtgatataaa cttagattgg atgccactaa agtttgctta tcacagaggg caagtagcac
15781 attatggcct tgaagtactt attgttctct tccagcaact tatgatttgc tccagtgatt
15841 ttgcttgcac actgactgga atataagaaa tgccttctat ttttgctatt aattccctcc
15901 ttttttgttt tgttttgtaa cgaagttgtt taacttgaag gtgaatgaag aataggttgg
15961 ttgccccta gttcctgag gagaaatgtt aatacttgaa caagtgtgtg tcagacaaat
16021 tgctgttatg tttatttaat taagtttgat ttctaagaaa atctcaaatg gtctgcactg
16081 atggaagaac agttctgta acaaaaagc ttgaaatttt tatatgactt ataatactgc
16141 tgtgagtttt aaaagtaaag caaagtaaa ctgagttgct tgtccagtgg gatggacagg
16201 aaagatgtga aataaaaacc aatgaaaaat gaactgctgt ggagaagtgt tacatttatg
16261 gaaaagaaa taggaaccctt gttcatcaaa ttgatagaaa agcttttaaa actaaacaaa
```

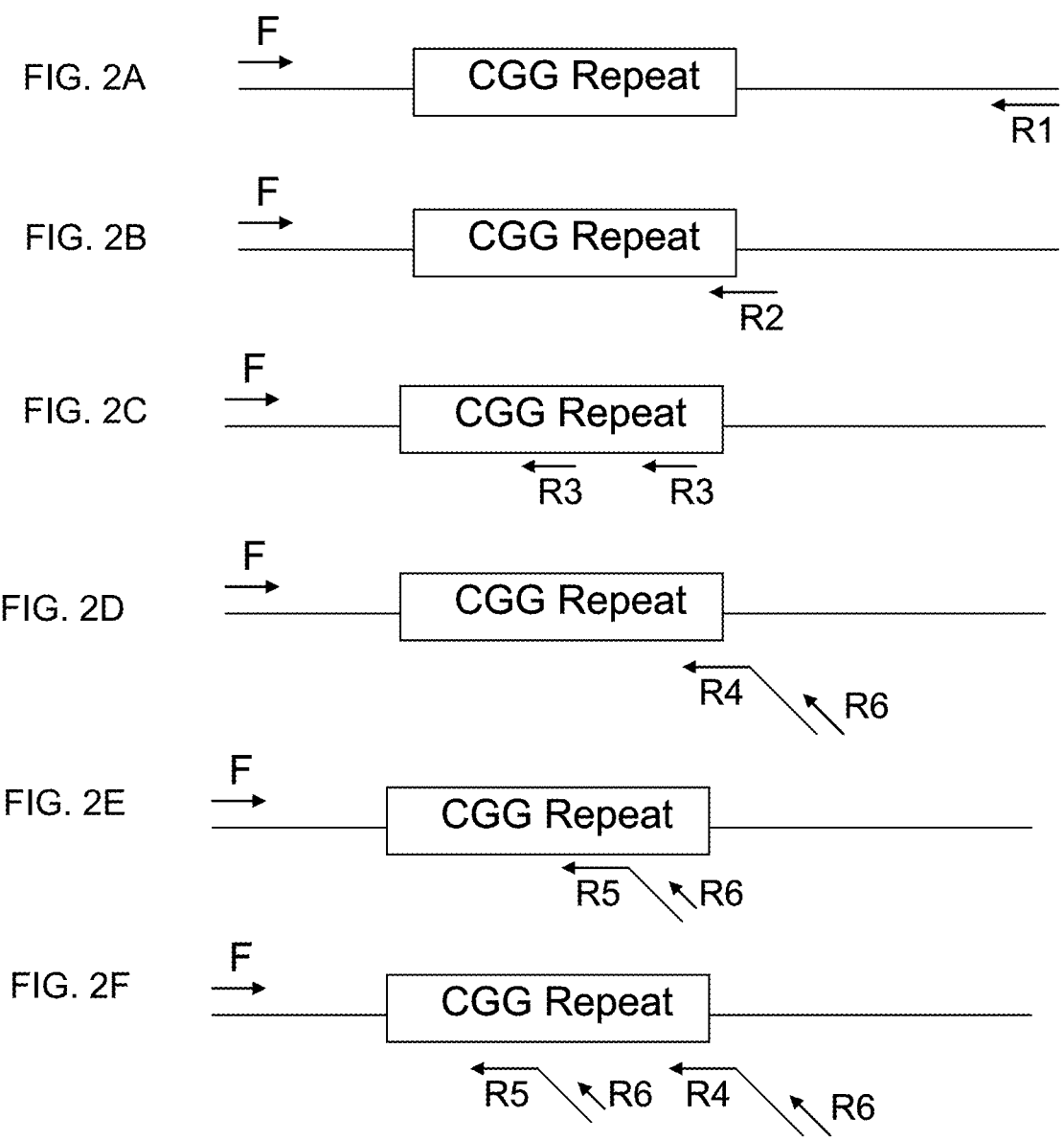

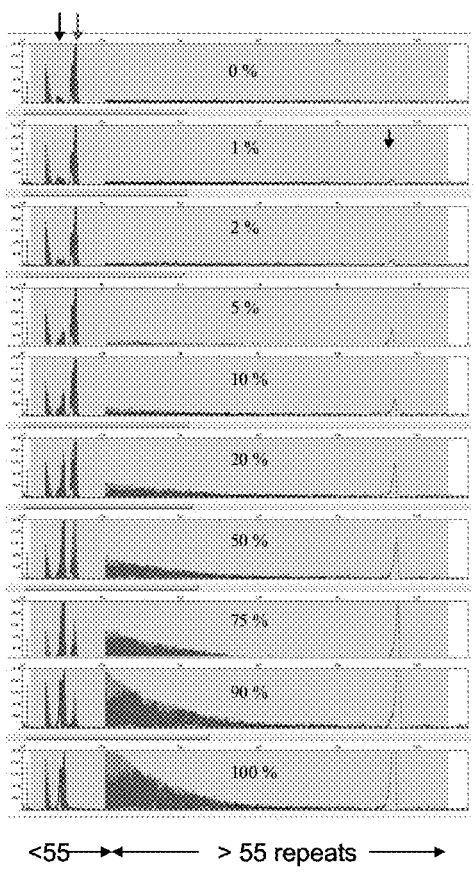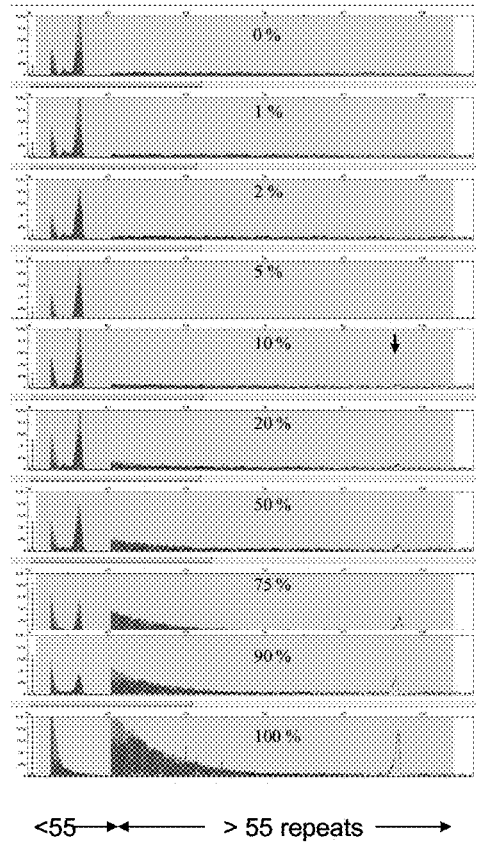
FIG. 6B
FIG. 6C

CGG1: CAGGAAACAGCTATGACC CG CCG CCG CC

CGG2: CAGGAAACAGCTATGACC CCG CCG XCG CCG CCG CC

CGG3: CAGGAAACAGCTATGACCCCGCCGCCGCCGCCGCCGCCGCCGCCG

CGG3-1: CAGGAAACAGCTATGACCCCGCCGCCGCCGCCGCCGCCGCC

CGG4-1: CAGGAAACAGCTATGACC CCG CCG CCG CCG CCG CCG

| | |
|---|---|
| (CCG)n | n= 1-15 |
| (CCG)₂ DCG (CCG)₂ CC | D= A, G, T |
| CG (CCG)₂ DCG (CCG)₂ CC | D= A, G, T |
| (CCG)₂ DCG (CCG)₂ | D= A, G, T |
| CG(CCG)₂ DCG (CCG)₂ C | D= A, G, T |
| G(CGG)₂ DGG (CGG)₂ C | D= A, G, T |
| (CCG)₂ N (CCG)₂ | N= A, C, G, T |
| CG(CCG)₂ N (CCG)₂CC | N= A, C, G, T |
| G(CCG)₂ N (CCG)₂CC | N= A, C, G, T |
| CG(CCG)₂ N (CCG)₂C | N= A, C, G, T |
| (CCG)₂ DCG (CCG)₂ DCG (CCG)₂CC | D= A, G, T |
| CG(CCG)₂ DCG (CCG)₂ DCG (CCG)₂CC | D= A, G, T |
| (CCG)₂ N (CCG)₂ N (CCG)₂ | N= A, C, G, T |
| (CCG)₂ N (CCG)₂ N (CCG)₂ CC | N= A, C, G, T |
| CG (CCG)₂ N (CCG)₂ N (CCG)₂ CC | N= A, C, G, T |
| CGCCGNCCGCC | N= A, C, G, T |
| GCCGNCCGCC | N= A, C, G, T |
| CGCCGCCGCC | |

FIG. 15

| | |
|---|---|
| (CGG)n | n= 1-15 |
| (CGG)₂ DGG (CGG)₂ CG | D= A, G, T |
| GG (CGG)₂ DGG (CGG)₂ CG | D= A, G, T |
| (CGG)₂ DGG (CGG)₂ | D= A, G, T |
| GG(CGG)₂ DGG (CGG)₂ C | D= A, G, T |
| G(CGG)₂ DGG (CGG)₂ C | D= A, G, T |
| (CGG)₂ N (CGG)₂ | N= A, C, G, T |
| GG(CGG)₂ N (CGG)₂CG | N= A, C, G, T |
| G(CGG)₂ N (CGG)₂CG | N= A, C, G, T |
| G(CGG)₂ N (CGG)₂C | N= A, C, G, T |
| (CGG)₂ DGG (CGG)₂ DGG (CGG)₂CG | D= A, G, T |
| GG(CGG)₂ DGG (CGG)₂ DGG (CGG)₂CG | D= A, G, T |
| (CGG)₂ N (CGG)₂ N (CGG)₂ | N= A, C, G, T |
| (CGG)₂ N (CGG)₂ N (CGG)₂ CG | N= A, C, G, T |
| GG (CGG)₂ N (CGG)₂ N (CGG)₂ CG | N= A, C, G, T |
| GGCGGNCGGCG | N= A, C, G, T |
| GCGGNCGGCG | N= A, C, G, T |
| GGCGGCGGCG | N= A, C, G, T |

FIG. 16

```
  1 cgccgcctgt gcagccgctg ccgccgccgc cgccgccgcc gccgccgccg ccgccgccgc
 61 cgccgctgcc gccccggctg ccgccgccgc ccgctgcctc tgccccggcc gccccccgcg
121 ccgctgccgc cgccggcccg cgccggcccg cagccagcca ggcgggcggc ccagcccgcc tgagcccgca
181 gcggctgccg ccgcagcgtc gggtcgctgg gtgcgcgggc taccgcggac cgagcggacc
241 cgagtgggcg accaggcgct tgcccgccca gtgccactgc cgccgcttcc tcgccggagc
301 acaggaccag acacctccag cgcccgctgc tgctgccgat gcggcccgga cactttttagc
361 tgggcgggag ggctggagag ccggggcccg ccagaaccg ccagcgagct gtgccgagag
421 ccgcgccgac ccgctgcgat cagggacagg cgcccgcccg ccgccgccgc ctggccgct  (SEQ ID NO: 75)
```

FIG. 21

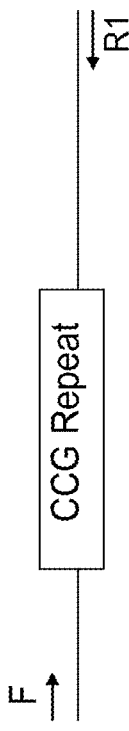
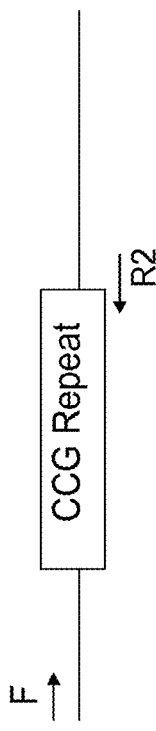
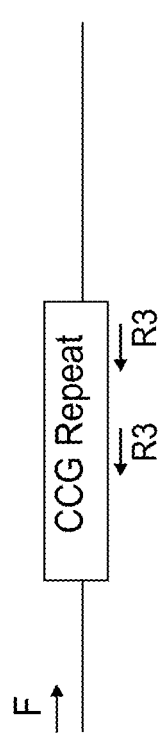
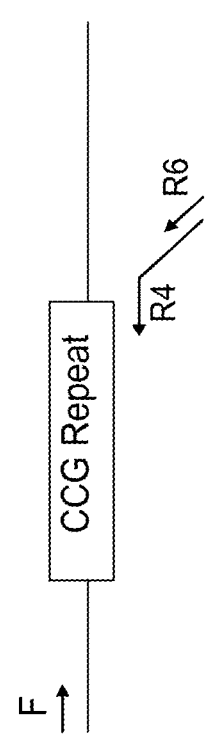
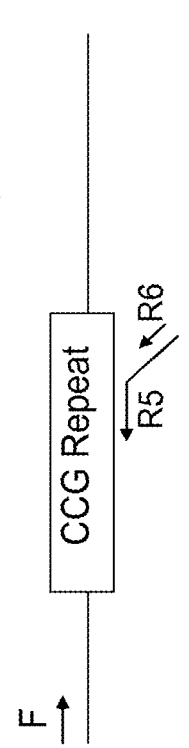
FIG. 22A  FIG. 22B  FIG. 22C  FIG. 22D  FIG. 22E  FIG. 22F

SEQUENCE LISTING

<160> NUMBER OF SEQ ID NOS: 113

<210> SEQ ID NO 1
<211> LENGTH: 3240
<212> TYPE: DNA
<213> ORGANISM: Homo sapiens

<400> SEQUENCE: 1

```
aatccatgtc ccttaaaggg cacagggtgt ctccacaggg ccgcccaaaa tctggtgaga      60
gagggcgtag acgcctcacc ttctgcctct acgggtcaca aaagcctggg tcaccctggt     120
tgccactgtt cctagttcaa agtcttcttc tgtctaatcc ttcaccccta ttctcgcctt     180
ccactccacc tcccgctcag tcagactgcg ctactttgaa ccggaccaaa ccaaaccaaa     240
ccaaaccaaa ccaaaccaga ccagacaccc cctcccgcgg aatcccagag aggccgaact     300
gggataaccg gatgcatttg atttcccacg ccactgagtg cacctctgca gaaatgggcg     360
ttctggccct cgcgaggcag tgcgacctgt caccgccctt cagccttccc gccctccacc     420
```

```
aagcccgcgc acgcccggcc cgcgcgtctg tctttcgacc cggcaccccg gccggttccc    480
agcagcgcgc atgcgcgcgc tcccaggcca cttgaagaga gagggcgggg ccgaggggct    540
gagcccgcgg ggggagggaa cagcgttgat cacgtgacgt ggtttcagtg tttacacccg    600
cagcgggccg ggggttcggc ctcagtcagg cgctcagctc cgtttcggtt tcacttccgg    660
tggagggccg cctctgagcg ggcggcgggc cgacggcgag cgcgggcggc ggcggtgacg    720
gaggcgccgc tgccaggggg cgtgcggcag cgcggcggcg gcggcggcgg cggcggcggc    780
ggaggcggcg gcggcggcgg cggcgcggc ggctgggcct cgagcgcccg cagcccacct     840
ctcgggggcg ggctcccggc gctagcaggg ctgaagagaa gatggaggag ctggtggtgg    900
aagtgcgggg ctccaatggc gctttctaca aggtacttgg ctctagggca ggcccatct     960 tcgcccttcc ttccctccct tttcttcttg gtgtcggcgg gaggcaggcc cggggccctc   1020
ttcccgagca ccgcgcctgg gtgccagggc acgctcggcg ggatgttgtt gggagggaag   1080
gactggactt ggggcctgtt ggaagccccc ctccgactcc gagaggccct agcgcctatc   1140
gaaatgagag accagcgagg agagggttct ctttcggcgc cgagcccgc cggggtgagc    1200 tggggatggg cgagggccgg cggcaggtac tagagccggg cgggaagggc cgaaatcggc   1260
gctaagtgac ggcgatggct tattccccct ttcctaaaca tcatctccca gcgggatccg   1320
ggcctgtcgt gtgggtagtt gtggaggagc gggggcgct tcagccgggc cgcctcctgc    1380
agcgccaaga gggcttcagg tctcctttgg cttctctttt ccggtctagc attgggactt   1440
cggagagctc cactgttctg ggcgagggct gtgaagaaag agtagtaaga agcggtagtc   1500
ggcaccaaat cacaatggca actgattttt agtggcttct ctttgtggat ttcggaggag   1560
attttagatc caaaagtttc aggaagaccc taacatggcc cagcagtgca ttgaagaagt   1620
tgatcatcgt gaatattcgc gtccccctt ttgttaaacg gggtaaattc aggaatgcac    1680
atgcttcagc gtctaaaacc attagcagcg ctgctactta aaaattgtgt gtgtgtgttt   1740
aagtttccaa agacctaaat atatgccatg aaacttcagg taattaactg agagtatatt   1800
attactaggg cattttttt ttaactgagc gaaaatattt ttgtgcccct aagaacttga    1860
ccacatttcc tttgaatttg tggtgttgca gtggactgaa ttgttgaggc tttatatagg   1920
cattcatggg tttactgtgc tttttaaagt tacaccattg cagatcaact aacacctttc   1980
agttttaaaa ggaagattta caaatttgat gtagcagtag tgcgtttgtt ggtatgtagg   2040
tgctgtataa attcatctat aaattctcat ttccttttga atgtctataa cctctttcaa   2100
taatatccca ccttactaca gtattttggc aatagaaggt gcgtgtggaa ggaaggctgg   2160
aaaatagcta ttagcagtgt ccaacacaat tcttaaatgt attgtagaat ggcttgaatg   2220
tttcagacag gacacgtttg gctataggaa aataaacaat tgactttatt ctgtgtttac   2280
caattttatg aagacatttg gagatcagta tatttcataa atgagtaaag tatgtaaact   2340
gttccatact ttgagcacaa agataaagcc ttttgctgta aaaggaggca aaaggtaacc   2400
ccgcgtttat gttcttaaca gtctcatgaa tatgaaattg tttcagttga ctctgcagtc   2460
aaaattttaa tttcattgat tttattgatc cataatttct tctggtgagt ttgcgtagaa   2520
tcgttcacgg tcctagatta gtggttttgg tcactgatt tctggcacta ataactataa    2580
tacatataca tatatatgtg tgagtaacgg ctaatggtta ggcaagattt tgattgacct   2640
gtgatataaa cttagattgg atgccactaa agtttgctta tcacagaggg caagtagcac   2700
attatggcct tgaagtactt attgttctct tccagcaact tatgatttgc tccagtgatt   2760
ttgcttgcac actgactgga atataagaaa tgccttctat ttttgctatt aattccctcc   2820
```

```
tttttttgttt tgttttgtaa cgaagttgtt taacttgaag gtgaatgaag aataggttgg    2880 ttgccccttta gttccctgag gagaaatgtt aatacttgaa caagtgtgtg tcagacaaat    2940
tgctgttatg tttatttaat taagtttgat ttctaagaaa atctcaaatg gtctgcactg    3000
atggaagaac agtttctgta acaaaaaagc ttgaaattt tatatgactt ataatactgc      3060
tgtgagtttt aaaagtaaag caaaagtaaa ctgagttgct tgtccagtgg gatggacagg    3120
aaagatgtga aataaaaacc aatgaaaaat gaactgctgt ggagaagtgt tacatttatg    3180 gaaaagaaa taggaacctt gttcatcaaa ttgatagaaa agcttttaaa actaaacaaa     3240
```

```
<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgtaaaacga cggccagtgc tcagctccgt ttcggtttca cttccggt                  48

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caggaaacag ctatgaccct cgaggcccag ccgccgccgc c                         41

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caggaaacag ctatgacccc gccgccgcc                                       29

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggaaacag ctatgacccg ccgccgcc                                        28

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggaaacag ctatgacccc gccgdcgccg ccgcc                                35
```

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caggaaacag ctatgacccc gccgccgccg ccgccgccgc cgccgccg                    48

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggaaacag ctatgacccc gccgccgccg ccgccgccg                             39

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caggaaacag ctatgacccc gccgccgccg ccgccgccgc cgccgcc                    47

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caggaaacag ctatgacccc gccgccgccg ccgccgcc                              38

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caggaaacag ctatgacc                                                    18

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctcagctcc gtttcggttt cacttccggt                                       30

```
<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agccccgcac ttccactttc ggtttcactt ccggt                              35

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgccgccgcc                                                          10

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccgccgaccg ccg                                                      13

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgccgtccg ccg                                                      13

<210> SEQ ID NO 17
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccgccggccg ccg                                                      13

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgccgcccg ccg                                                      13
```

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
cgccgccgac gccgccgcc         19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cgccgccgtc gccgccgcc         19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cgccgccggc gccgccgcc         19

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
cgccgccgcc cgccgcc           17

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ctcgaggccc agccgccg           18

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ctcgaggccc agccgtcgcc g         21

<210> SEQ ID NO 25

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctcgaggccc agccgacgcc g                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcgaggccc agccggcgcc g                                              21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caggaaacag ctatgacccg ccg                                            23

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caggaaacag ctatgacgcc gccgcc                                         26

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caggaaacag ctatgacccg ccgaccgccg                                     30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caggaaacag ctatgacccg ccgtccgccg                                     30

<210> SEQ ID NO 31
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caggaaacag ctatgacccg ccggccgccg                                        30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caggaaacag ctatgacccg ccgcccgccg                                        30

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caggaaacag ctatgacgcc gccgacgccg ccgcc                                  35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caggaaacag ctatgacgcc gccgtcgccg ccgcc                                  35

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caggaaacag ctatgacgcc gccggcgccg ccgcc                                  35

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caggaaacag ctatgacgcc gccgcccgcc gcc                                    33

<210> SEQ ID NO 37
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
caggaaacag ctatgacctc gaggcccacc gccg                                34

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caggaaacag ctatgacctc gaggcccagc cgtcgccgcc g                        41

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caggaaacag ctatgacctc gaggcccagc cgacgccgcc g                        41

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caggaaacag ctatgacctc gaggcccagc cggcgccgcc g                        41

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgcggcggcg                                                           10

<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cggcggacgg cgg                                                       13

<210> SEQ ID NO 43
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
cggcggtcgg cgg                                                        13

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cggcgggcgg cgg                                                        13

<210> SEQ ID NO 45
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cggcggccgg cgg                                                        13

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggcggcggag gcggcggcg                                                  19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggcggcggtg gcggcggcg                                                  19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcggcgggg gcggcggcg                                                  19

<210> SEQ ID NO 49
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 49
ggcggcggcc ggcggcg                                                    17

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine

<400> SEQUENCE: 50
cgtgcngcag cgcggcgg                                                   18

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine

<400> SEQUENCE: 51
cgtgcngcag cgcggtggcg g                                               21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine

<400> SEQUENCE: 52
cgtgcngcag cgcggaggcg g                                               21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine

<400> SEQUENCE: 53
cgtgcngcag cgcggggcg g                                                21

<210> SEQ ID NO 54
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 54
caggaaacag ctatgaccgg cgg                                              23

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caggaaacag ctatgaccgg cggcg                                            25

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caggaaacag ctatgaccgg cggacggcgg                                       30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caggaaacag ctatgaccgg cggtcggcgg                                       30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caggaaacag ctatgaccgg cggccggcgg                                       30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
caggaaacag ctatgaccgg cgggcggcgg                                       30

<210> SEQ ID NO 60
<211> LENGTH: 35
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 60
caggaaacag ctatgacccg gcggaggcgg cggcg                                35

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caggaaacag ctatgacccg gcggtggcgg cggcg                                35

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caggaaacag ctatgacccg gcgggggcgg cggcg                                35

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
caggaaacag ctatgacccg gcggccggcg gcg                                  33

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caggaaacag ctatgacccg gcggtcggcg gcg                                  33

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caggaaacag ctatgacccg gcgggcggcg gcg                                  33

<210> SEQ ID NO 66
<211> LENGTH: 33
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 66
caggaaacag ctatgacccg gcggacggcg gcg                                    33

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Inosine

<400> SEQUENCE: 67
caggaaacag ctatgacccg tgcngcagcg cggtggcggc gg                          42

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Inosine

<400> SEQUENCE: 68
caggaaacag ctatgacccg tgcngcagcg cggaggcggc gg                          42

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Inosine

<400> SEQUENCE: 69
caggaaacag ctatgacccg tgcngcagcg cggggcggc gg                           42

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
taatacgact cactataggg                                                   20

<210> SEQ ID NO 71
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
caggaaacag ctatgaccct cgaggcccag ccgccgccgc cgcc        44

<210> SEQ ID NO 72
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caggaaacag ctatgaccct cgaggcccag ccgccgccgc cgccgcc     47

<210> SEQ ID NO 73
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caggaaacag ctatgaccct cgaggcccag ccgccgcc              38

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caggaaacag ctatgaccct cgaggcccag ccgccg                36

<210> SEQ ID NO 75
<211> LENGTH: 479
<212> TYPE: DNA
<213> ORGANISM: Homo sapiens

<400> SEQUENCE: 75
cgccgcctgt gcagccgctg ccgccgccgc cgccgccgcc gccgccgccg ccgccgccgc      60
cgccgctgcc gccccggctg ccgcgccgcg ccgctgcctc tgccccggcc gccccgccg      120 ccgctgccgc cgccggcccg cagccagcca ggcgggcggc ccagcccgcc tgagcccgca     180
gcggctgccg ccgcagcgtc gggtcgctgg gtgcgcgggc taccgcggac cgagcggacc     240
cgagtgggcg accaggcgct tgcccgccca gtgccactgc cgccgcttcc tcgccggagc     300
acaggaccag acacctccag cgcccgctgc tgctgccgat gcggcccgga cactttagc      360 tgggcgggag ggctggagag ccgggggccg ccgagaaccg ccagcgagct gtgccgagag     420
ccgcgccgac ccgctgcgat cagggacagg cgcccgcccg ccgccgccgc ctggccgct      479

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cgccgcctgt gcagccgctg                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gccccggctg ccgcgccgcg                                              20

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(45)
<223> OTHER INFORMATION: This region may encompass 1 to 15 "ccg"
      repeating units

<400> SEQUENCE: 78
ccgccgccgc cgccgccgcc gccgccgccg ccgccgccgc cgccg                  45

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ccgccgdcgc cgccgcc                                                 17

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgccgccgdc gccgccgcc                                               19

<210> SEQ ID NO 81
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccgccgdcgc cgccg                                                   15

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
cgccgccgdc gccgccgc                                               18

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcggcggdgg cggcggc                                                17

<210> SEQ ID NO 84
<211> LENGTH: 13
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: a, c, t or g

<400> SEQUENCE: 84
ccgccgnccg ccg                                                    13

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t or g

<400> SEQUENCE: 85
cgccgccgnc cgccgcc                                                17

<210> SEQ ID NO 86
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: a, c, t or g

<400> SEQUENCE: 86
gccgccgncc gccgcc                                                 16

<210> SEQ ID NO 87
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<221> NAME/KEY: modified_base
<222> LOCATION: (9)..(9)
<223> OTHER INFORMATION: a, c, t or g

<400> SEQUENCE: 87
cgccgccgnc cgccgc                                                   16

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccgccgdcgc cgccgdcgcc gccgcc                                        26

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgccgccgdc gccgccgdcg ccgccgcc                                      28

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (14)..(14)
<223> OTHER INFORMATION: a, c, t or g

<400> SEQUENCE: 90
ccgccgnccg ccgnccgccg                                               20

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (14)..(14)
<223> OTHER INFORMATION: a, c, t or g

<400> SEQUENCE: 91
ccgccgnccg ccgnccgccg cc                                            22

<210> SEQ ID NO 92
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (16)..(16)
<223> OTHER INFORMATION: a, c, t or g

<400> SEQUENCE: 92
cgccgccgnc cgccgnccgc cgcc                                            24

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t or g

<400> SEQUENCE: 93
cgccgnccgc c                                                          11

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, t or g

<400> SEQUENCE: 94 gccgnccgcc                                                            10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgccgccgcc                                                            10

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(45)
<223> OTHER INFORMATION: This region may encompass 1 to 15 "cgg"
      repeating units
```

```
<400> SEQUENCE: 96
cggcggcggc ggcggcggcg gcggcggcgg cggcggcggc ggcgg          45

<210> SEQ ID NO 97
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cggcggdggc ggcggcg                                          17

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ggcggcggdg gcggcggcg                                        19

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cggcggdggc ggcgg                                            15

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggcggcggdg gcggcggc                                         18

<210> SEQ ID NO 101
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcggcggdgg cggcggc                                          17

<210> SEQ ID NO 102
<211> LENGTH: 13
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

```
<222> LOCATION: (7)..(7)
<223> OTHER INFORMATION: a, c, t or g

<400> SEQUENCE: 102
cggcggncgg cgg                                                      13

<210> SEQ ID NO 103
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t or g

<400> SEQUENCE: 103
ggcggcggnc ggcggcg                                                  17

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: a, c, t or g

<400> SEQUENCE: 104
gcggcggncg gcggcg                                                   16

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: a, c, t or g

<400> SEQUENCE: 105
gcggcggncg gcggc                                                    15

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cggcggdggc ggcggdggcg gcggcg                                        26

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 107
ggcggcggdg gcggcggdgg cggcggcg                                          28

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (14)..(14)
<223> OTHER INFORMATION: a, c, t or g

<400> SEQUENCE: 108
cggcggncgg cggncggcgg                                                   20

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (14)..(14)
<223> OTHER INFORMATION: a, c, t or g

<400> SEQUENCE: 109
cggcggncgg cggncggcgg cg                                                22

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (16)..(16)
<223> OTHER INFORMATION: a, c, t or g

<400> SEQUENCE: 110
ggcggcggnc ggcggncggc ggcg                                              24

<210> SEQ ID NO 111
<211> LENGTH: 11
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)

```
<223> OTHER INFORMATION: a, c, t or g

<400> SEQUENCE: 111
ggcggncggc g                                                    11

<210> SEQ ID NO 112
<211> LENGTH: 10
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, t or g

<400> SEQUENCE: 112 gcggncggcg                                                      10

<210> SEQ ID NO 113
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggcggcggcg                                                      10
```

METHOD TO DETECT REPEAT SEQUENCE MOTIFS IN NUCLEIC ACID

CROSS-REFERENCE TO RELATED PATENT APPLICATIONS

This application is a Divisional of U.S. application Ser. No. 15/174,038, filed Jun. 6, 2016, which is a Continuation of U.S. application Ser. No. 13/576,740, which is the U.S. National Stage of PCT/US2011/023777, filed Feb. 4, 2011, which claims the priority of U.S. Provisional Application No. 61/302,059 filed Feb. 5, 2010 which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 22, 2019, is named sequence.txt and is 32,801 bytes in size.

FIELD OF THE INVENTION

This invention relates to methods of detecting genetic mutations characterized by an expansion of tandem repeats such as CGG repeats in the FMR1 gene and CCG repeats in FMR2 gene.

BACKGROUND

A tandem repeat in DNA represents two or more contiguous approximate copies of a pattern of nucleotides. Tandem repeats have been shown to be associated with a variety of human diseases. Dramatic expansion of trinucleotide repeats has been associated with such diseases as fragile-X mental retardation (see Verkerk, et al., (1991) Cell, 65, 905-914), Huntington's disease (see Huntington's Disease Collaborative Research Group. (1993) Cell, 72, 971-983), myotonic dystrophy (see Fu, et al., (1992) Science, 255, 1256-1258), spinal and bulbar muscular atrophy (see La Spada, et al., (1991) Nature, 352, 77-79) and Friedreich's ataxia (see Campuzano, et al., (1996) Science, 271, 1423-1427).

Fragile X syndrome (FXS, OMIM # 300624) is the most common inherited mental retardation syndrome, affecting ~1:4000 males and ~1:8000 females. The disease is caused by the expansion of the trinucleotide CGG repeat in the 5'-untranslated (UTR) region of the fragile X mental retardation protein 1 (FMR1) gene. Methylation of the CGG tract leads to silencing of expression of the FMR1 gene. The American College of Medical Genetics (Maddalena et al. Genet Med 2001; 3(3):200-5; Sherman et al. Genet Med 2005;7(8):584-7) defines a normal repeat length as between 5-44. Intermediate alleles of between 45-54 repeats show almost no expansion. Premutation alleles have 55-200 CGG, while full mutation alleles have >200 repeats. As an X-linked dominant disease, FXS is diagnosed more frequently in males than females, but females can present with milder symptoms, or with FXS due to skewed X-inactivation. Thirty-forty percent of male carriers of a premutation allele will suffer from Fragile X-associated Tremor and Ataxia (FXTAS) by age 50 (Hagerman et al. Ment Retard Dev Disabil Res Rev 2004; 10(1): 25-30; Hagerman et al. Am J Hum Genet 2004; 74(5): 1051-6) Various studies showed that the larger the repeat size the stronger the chance of presenting with FXTAS, but the penetrance i.e. the chance of being affected by FXTAS seems to be around 33% for male carriers of alleles ~70 repeats or higher. Some female premutation carriers are affected with premature ovarian insufficiency (FXPOI; also know as premature ovarian failure) (Allingham-Hawkins et al. Am J Med Genet 1999;83 (4):322-5; Hundscheid et al. Hum. Reprod. 2001; 13(3): 457-462). Female premutation carriers showed overall higher levels of follicular stimulating hormone than normal or full mutation carriers and decreased levels of anti-Mullerian hormone, Inhibin A and inhibin B, all indicators of ovarian decline (Hundscheid et al. Hum. Reprod. 2001; 13(3): 457-462). The reported penetrance i.e. the chance of being affected by FXPOI in female premutation carriers is 20-28% of larger alleles.

Several studies have examined the carrier frequency of premutation and/or full mutation alleles in FMR1 gene in different populations, and as in any other genetic disease, the frequency varies by population and region; 1:113 in Israel (Toledano-Alhadef et al. Am J Hum Genet 2001; 69(2):351-60), 1:259 in Quebec (Rousseau et al. Am J Hum Genet 1995;57(5):1006-18), in Finland the frequency was 1:246, and in the U.S. state of Georgia it was 1:436. The frequency was found to be between 1:257-1:382 in the U.S. population in general (Cronister et al. Genet Med 2005;7(4):246-50). Methods of amplifying the CGG repeat tract in the FMR1 gene has previously been reported. See, Fu et al. Cell 1991; 67: 1047-1058; Erster et al. Hum Genet. 1992; 90: 55-61; Pergolizzi et al. Lancet. 1992; 339: 271-272; Warner et al. J Med Genet. 1996; 33: 1022-1026; Daniels et al. J Assist Reprod Genet. 1996; 13(2): 163-169; Strelnikov et al. Hum Mutat. 1999; 13(2): 166-169; Zhou et al. J Med Genet. 2004; 41(4): e45; Saluto et al. J Mol Diagn. 2005; 7(5): 605-612; Zhou et al. Clin Chem. 2006; 52(8): 1492-1500; Dahl et al. Clin Chem. 2007; 53(4): 790-793; Strom et al. Genet Med. 2007; 9(4): 199-207; Khaniani et al. Mol Cytogenet. April 8; 1:5; Tassone et al. J Mol Diagn. 2008; 10(1): 43-49; Filipovic-Sadic et al. Clin Chem. Jan. 7 2010 (epub); Lyon et al. J Mol. Diagn. 2010; 12(4): 505-511; Hantash et al. Genet Med. Feb. 17 2010 (epub); U.S. Pat. Nos. 5,658,764, 6,200, 747, and 6,114,150, and US Patent Application Publication 2008/0113355.

Fragile X E (FRAXE) mental retardation (OMIM 309548) is associated to a fragile site localized in chromosome Xq28 and is the cause of a non-syndromic X-linked mental retardation affecting 1/50,000 newborn males. The disorder is due to the silencing of the Fragile X Mental Retardation 2 (FMR2) gene, as a consequence of a CCG expansion located upstream to this gene. FRAXE alleles can be divided into four categories: normal (6-30 CCG repeats), intermediate (31-60 CCG repeats), premutation (61-200 CCG repeats), and full mutation (over 200 CCG repeats). See, Gecz et al. Nat. Genet. 1996;13: 105-108; Gu et al. Nat. Genet. 1996;13:109-113; Knight et al. Cell. 1993;74:127-134; and Strelnikov et al. Hum Mutat. 1999;13(2):166-9.

SUMMARY OF THE INVENTION

Described is a nucleic acid amplification method for detecting whether a gene associated with a tandem triplet repeat tract has a normal, or an expanded triplet repeat track. The expanded triplet repeat tract may include a premutation or may include a full mutation with a greater number of repeats than the premutation. In one embodiment, amplification is by the polymerase chain reaction using a pair of primers. The amplified triplet repeat tract and any portions thereof are separated according to size. In one embodiment, the method of separation is electrophoresis, which preferably is capillary gel electrophoresis.

In one aspect, the method is used to determine the presence or absence of an expansion of the CGG repeat tract in the 5'-untranslated region (5'-UTR) of fragile X related mental retardation gene 1 (FMR1) in an individual. The method involves amplification using at least a primer pair wherein one or both primers of the primer pair hybridize to and prime in the CGG repeat tract so as to generate amplicons that contain all or portions of the CGG repeat tract. The primer pair can include a downstream primer that comprises a CCG repeat segment which contains less than four consecutive CCG triplet repeats and hybridizes to at least a portion of said CGG repeat tract. Alternatively or in addition, the primer pair can include an upstream primer that comprises a CGG repeat segment which contains less than four consecutive CGG triplet repeats and hybridizes to at least a portion of the complement of said CGG repeat tract. The amplicons generated are then separated according to size, wherein the size(s) of the amplicons indicates the presence or absence of expansion of the CGG repeat tract in said 5'-UTR of the FMR1 gene.

In some embodiments, when the primer pair for amplifying CGG repeat tract in the 5'-UTR of FMR1 gene includes a downstream primer that comprises less than four consecutive CCG triplet repeats and hybridizes to at least a portion of the CGG repeat tract, the upstream primer is complementary to a region upstream of the CGG repeat tract. Likewise, when the primer pair includes an upstream primer that comprises less than four consecutive CGG triplet repeats and hybridizes to at least a portion of the complement of the CGG repeat tract, the downstream primer is complementary to sequence downstream of the CGG tract.

In another aspect, the method is used to determine the presence or absence of an expansion of the CCG repeat tract in the 5'-untranslated region (5'-UTR) of fragile X related mental retardation gene 2 (FMR2) in an individual. The method involves amplification using at least a primer pair wherein one or both primers of the primer pair hybridize to and prime in the CCG repeat tract so as to generate amplicons that contain all or portions of the CCG repeat tract. The primer pair can include a downstream primer that comprises one or more CGG triplet repeats and hybridizes to at least a portion of said CCG repeat tract. In some embodiments, the downstream primer may comprise two or more consecutive CGG triplet repeats. Alternatively or in addition, the primer pair can include an upstream primer that comprises one or more CCG repeat segment and hybridizes to at least a portion of the complement of said CCG repeat tract. In some embodiments, the upstream primer may comprise two or more consecutive CCG triplet repeats. The amplicons generated are then separated according to size, wherein the size(s) of the amplicons indicates the presence or absence of expansion of the CCG repeat tract in said 5'-UTR of the FMR2 gene.

In some embodiments, when the primer pair for amplifying CCG repeat tract in the 5'-UTR of FMR2 gene includes a downstream primer that comprises one or more consecutive CGG triplet repeats and hybridizes to at least a portion of the CCG repeat tract, the upstream primer is complementary to a region upstream of the CCG repeat tract. Likewise, when the primer pair includes an upstream primer that comprises one or more consecutive CCG triplet repeats and hybridizes to at least a portion of the complement of the CCG repeat tract, the downstream primer is complementary to sequence downstream of the CCG tract.

The primers can include 5' tails that can function as a priming site and have sequence with little to no sequence homology to the FMR1 or FMR2 gene. Thus, an additional primer (e.g. M13 sequence) can be used which primes in the tail segment of one or both primers of the initial primer to boost the amount of amplicons generated.

The CGG or CCG repeat segments of the primers can have various combinations of triplets such as are shown in FIG. 15 for primers comprising CCG triplets and FIG. 16 for primers comprising CGG triplets. In one embodiment, the primer that has the CGG or CCG repeat segment also includes sequence that flanks the CGG or CCG repeat track so as to allow the primer to hybridize at the junction between the CGG repeat tract or CCG repeat tract and flanking sequence. For example, in the case of FMR1 gene, the "junctional" downstream primer has CCG repeat sequence at the 3' end of the primer which sequence includes sequence upstream from the 3' end of the repeat tract and continues into the flanking sequence that is directly downstream of the repeat tract. Likewise, the "junctional" form of the upstream primer has at its 3' end CGG repeat sequence that includes sequence downstream from the 5' end of the repeat tract and continues upstream into the flanking sequence located 5' to the repeat tract. As already discussed, these junctional primers can include a tail for priming by an additional primer.

In some embodiments, for amplifying CGG repeat tract in the 5'-UTR of FMR1 gene the downstream primer comprises or consists essentially of a sequence selected from the group consisting of SEQ ID NOs: 3-6, SEQ ID NOs 14-40, SEQ ID NOs 71-74 and the upstream primer comprises or consists essentially of a sequence selected from the group consisting of SEQ ID NOs: 41-69. In some embodiments, for amplifying CGG repeat tract in the 5'-UTR of FMR1 gene the CGG or CCG repeat segments of the primer can have less than 3 consecutive CGG or CCG repeats. In some embodiments, the downstream primer CCG hybridizing sequence has two sets of two consecutive CCG triplets (separated by at least one base) and the upstream primer has as the CGG hybridizing sequence two sets of two consecutive CGG triplets (separated by at least one base). In these embodiments, the downstream primer comprises or consists essentially of a sequence selected from the group consisting of SEQ ID NOs: 15-22 and 29-36 and the upstream primer comprises or consists essentially of a sequence selected from the group consisting of SEQ ID NOs. 42-49 and 56-66.

In some embodiments, for amplifying CCG repeat tract in the 5'-UTR of FMR2 gene the upstream primer comprises or consists essentially of a sequence selected from the group consisting of SEQ ID NOs: 14-40, 71-74, and 76 and the downstream primer comprises or consists essentially of a sequence selected from the group consisting of SEQ ID NOs: 41-69 and 77. In some embodiments, for amplifying CCG repeat tract in the 5'-UTR of FMR2 gene, the CGG or CCG repeat segments of the primer can have less than 3 consecutive CGG or CCG repeats. In some embodiments, the upstream primer has two sets of two consecutive CCG triplets (separated by at least one base) and the downstream primer has two sets of two consecutive CGG triplets (separated by at least one base). In these embodiments, the upstream primer comprises or consists essentially of a sequence selected from the group consisting of SEQ ID NOs: 15-22 and 29-36 and the downstream primer comprises or consists essentially of a sequence selected from the group consisting of SEQ ID NOs. 42-49 and 56-66.

In accordance with the method, amplification of extended triplet repeats including premutation and full mutation following size separation of the amplicons yields a tapering or stutter pattern of amplicon sizes. In some embodiments, in the case of a full mutation in FMR1 gene, a lone peak is visible at about 1050 bp on a capillary gel.

In some embodiments, the signal for the full mutation lone peak can be enhanced by using a deoxy GTP analogue such as 7-deaza-2'-deoxy GTP in the amplification reaction mixture. In some embodiments, the dGTP analogue substitutes entirely for dGTP in the reaction mixture.

In some embodiments, the amplification is cyclic and the ramp rate between cycles is selected at about 60-70% (about 0.4° C. to 0.6° C./sec) for the denaturation and/or extension steps and about 20-30% (about 0.4° C. to 0.6° C./sec) for the annealing step.

In another aspect, the method of triplet primed amplification is used to identify a female that is homozygous normal versus a female that is heterozygous and having a normal allele and an allele with an expanded CGG tract length in the 5'-UTR of FMR1 gene. The above described methods may be used in this instance to obtain amplicons which are separated according to size so as to estimate the number of CGG repeats in said amplicons, wherein detection of only a normal number of CGG repeats indicates a homozygous normal female and detection of both amplicons with a normal number of CGG repeats and detection of amplicons with an abnormally high number of CGG repeats indicates a female heterozygous and having an allele with an expanded CGG tract length. In some embodiments, the normal number of CGG repeats is between 4 to 44 repeats while an abnormally high number of repeats is greater than 54 repeats. In some embodiments, an expanded CGG tract length representing a premutation has CGG repeats of between 55-200 while in other embodiments, an expanded CGG tract length representing a full mutation has greater than 200 CGG triplet repeats.

In another aspect, the method of triplet primed amplification is used to identify a female that is homozygous normal versus a female that is heterozygous and having a normal allele and an allele with an expanded CCG tract length in the 5'-UTR of FMR2 gene. The above described methods may be used in this instance to obtain amplicons which are separated according to size so as to estimate the number of CCG repeats in said amplicons, wherein detection of only a normal number of CCG repeats indicates a homozygous normal female and detection of both amplicons with a normal number of CCG repeats and detection of amplicons with an abnormally high number of CCG repeats indicates a female heterozygous and having an allele with an expanded CCG tract length. In some embodiments, the normal number of CCG repeats is between 6 to 30 repeats while an abnormally high number of repeats is greater than 60 repeats. In some embodiments, an expanded CCG tract length representing a premutation has CCG repeats of between 61-200 while in other embodiments, an expanded CCG tract length representing a full mutation has greater than 200 CCG triplet repeats.

In yet a further aspect, the method of triplet primed amplification is used to screen newborns to determine if they have an expanded CGG tract in the FMR1 gene. This method can be performed as for the method above for screening females to determine normal homozygous versus heterozygous with a expanded CGG repeat tract.

"Primer" as used herein refers to an oligonucleotide that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3'-end of the primer in the presence of a DNA or RNA polymerase. The 3'-nucleotide of the primer should generally be complementary to the target sequence at a corresponding nucleotide position for optimal expression and amplification. An oligonucleotide "primer" may occur naturally, as in a purified restriction digest or may be produced synthetically. The term "primer" as used herein includes all forms of primers that may be synthesized including peptide nucleic acid primers, locked nucleic acid primers, phosphorothioate modified primers, labeled primers, and the like.

Primers are typically between about 10 and about 100 nucleotides in length, preferably between about 15 and about 60 nucleotides in length, more preferably between about 20 and about 50 nucleotides in length, and most preferably between about 25 and about 40 nucleotides in length. In some embodiments, primers can be at least 8, at least 12, at least 16, at least 20, at least 25, at least 30, at least 35, at least 40, at least 45, at least 50, at least 55, at least 60 nucleotides in length. An optimal length for a particular primer application may be readily determined in the manner described in H. Erlich, PCR Technology, Principles and Application for DNA Amplification (1989).

As used herein, a "carrier" is an individual who carries a mutated or altered allele of a gene but is not affected by the disorder or disease associated with the mutation. Carriers can pass the mutation to a child or offspring in future generations, who may be affected with the disease or disorder. With respect to Fragile X syndrome, both males and females may be carriers. As used herein, the term carrier encompasses individuals having a premutation allele or a full mutation allele. Such individual carriers may also be referred to herein as "premutation carrier" (i.e., having a premutation FMR1 allele) or a "full mutation carrier" (i.e., having a full mutation FMR1 allele).

As used herein, "5'-untranslated region (5'-UTR)" of the FMR1 gene means the region of FMR1 gene upstream of the first codon that is not translated into a protein. In one embodiment, the 5'-UTR of FMR1 gene includes promoters, enhancers and CGG repeats.

As used herein "CGG repeat tract" means the sequence of tandem repeats of CGG trinucleotides in the 5'-UTR of the FMR1 gene. The number of CGG repeats in the CGG repeat tract may vary within an individual or between two individuals. The number of CGG repeats in the CGG repeat tract of the FMR1 gene can be at least 5, 10, 15, 20, 30, 40, 50, 75, 100, 200, 300, 500, 1,000, 2,000 or more. In some embodiments, the number of CGG repeats in the CGG repeat tract can vary from about 5 to about 2,000, to about 2,100, to about 2,300, to about 2,500 repeats. An exemplary CGG repeat tract sequence of FMR1 gene corresponds to nucleotide positions 13833 to 13962 of SEQ ID NO: 1.

As used herein "CGG repeat expansion" means a number of CGG repeats at the 5'-UTR of FMR1 gene which is greater than the normal range of 5-44 repeats. Typically normal repeat lengths are between 5-44. In some embodiments, the repeat lengths can increase to 45-54 repeats. In some embodiments, repeat lengths can increase to between 55-200 CGG repeats. Individuals having between 55-200 CGG repeats in the 5'-UTR of FMR1 gene are considered to have premutation allele. In some embodiments, the repeat lengths can increase to over 200 repeats. Individuals having greater than 200 repeats in the 5'-UTR of the FMR1 gene are considered to have a full mutation allele. The following abbreviations are used. NF: normal female; GF, intermediate female; PF, premutation female; FF; affected female; NM, normal male; GM, intermediate male; PM, premutation male; FM, affected male. "Normal" is used herein has 5-44 repeats, "Intermediate has 45-54 repeats, "Premutation" has 55-200 repeats and "Full Mutation" has >200 repeats.

As used herein, "5'-untranslated region (5'-UTR)" of the FMR2 gene means the region of FMR2 gene upstream of the first codon that is not translated into a protein. In one embodiment, the 5'-UTR of FMR2 gene includes promoters, enhancers and CCG repeats.

As used herein "CCG repeat tract" means the sequence of tandem repeats of CCG trinucleotides in the 5'-UTR of the FMR2 gene. The number of CCG repeats in the CCG repeat tract may vary within an individual or between two individuals. The number of CCG repeats in the CCG repeat tract of the FMR2 gene can be at least 5, 10, 15, 20, 30, 40, 50, 75, 100, 200, 300, 500, 1,000, 2,000 or more. In some embodiments, the number of CCG repeats in the CCG repeat tract can vary from about 5 to about 2,000, to about 2,100, to about 2,300, to about 2,500 repeats. An exemplary CCG repeat tract sequence of FMR2 gene corresponds to nucleotide positions 21 to 65 of SEQ ID NO: 75.

As used herein "CCG repeat expansion" means a number of CCG repeats at the 5'-UTR of FMR2 gene which is greater than the normal range of 6-30 repeats. Typically normal repeat lengths are between 6-30. In some embodiments, the repeat lengths can increase to 31-60 repeats. In some embodiments, repeat lengths can increase to between 61-200 CCG repeats. Individuals having between 31-60 CCG repeats in the 5'-UTR of FMR2 gene are considered to have intermediate allele. Individuals having between 61-200 CCG repeats in the 5'-UTR of FMR2 gene are considered to have premutation allele. In some embodiments, the repeat lengths can increase to over 200 repeats. Individuals having greater than 200 CCG repeats in the 5'-UTR of the FMR2 gene are considered to have a full mutation allele. The following abbreviations are used. NF: normal female; GF, intermediate female; PF, premutation female; FF; affected female; NM, normal male; GM, intermediate male; PM, premutation male; FM, affected male. "Normal" as used herein has 6-30 repeats, "Intermediate has 31-60 repeats, "Premutation" has 61-200 repeats and "Full Mutation" has >200 repeats.

As used herein, "penetrance in patients" in the context of Fragile X-associated tremor and ataxia syndrome (FXTAS) and Fragile X-associated premature ovarian insufficiency (FXPOI) means the chance of being affected by FXTAS or FXPOI as is calculated by the fraction of the population affected with FXTAS and FXPOI having premutation in FMR1 gene which may be ≥30 CGG repeats, ≥40 CGG repeats, ≥50 CGG repeats, ≥70 CGG repeats, or ≥100 CGG repeats. Alternatively, the permutation size may be determined relative to the population affected with FXTAS and/or FXPOI.

"Sample" or "patient sample" as used herein includes biological samples such as cells, cell lysates, tissues and body fluids. Sample may be of human or non-human origin. Sample may include, but are not limited to, amniotic fluid, biopsies, blood, blood spots, blood cells, bone marrow, amniotic fluid, cerebrospinal fluid, chorionic villi, fecal samples, excrements, fine needle biopsy samples, peritoneal fluid, plasma, pleural fluid, bronchial alveolar lavage, bronchial wash, saliva, semen, serum, sputum, tears, buccal swab, tissue, tissue homogenates, frozen tissue, paraffin sections of tissue, tissue culture media, cells, fetal cells, cell lysates, cell from culture, cell culture supernatant, fetus, embryo, and urine. A sample may include a body fluid that is "acellular."

An "acellular body fluid" is a sample that contains less than about 1% (w/w) of whole cellular material. Acellular body fluid includes samples that are naturally acellular when obtained from the individual, or may be cellular fluids that are made to be acellular. For example, plasma is an acellular body fluid derived from blood by removing whole cellular material from blood by methods known in the art (e.g., centrifugation, filtration, and the like). Serum is an acellular body fluid obtained from clotted blood after the clotted fraction is removed. Naturally occurring acellular body fluids include, for example, certain samples of spinal fluid and urine, such as are typically obtained from a normal healthy individual.

As used herein, the term "oligonucleotide" refers to a short polymer composed of deoxyribonucleotides, ribonucleotides or any combination thereof. Oligonucleotides of the invention are generally between about 10 and about 100 nucleotides in length. Oligonucleotides are preferably 15 to 70 nucleotides long, with 20 to 26 nucleotides being the most common. The single letter code for nucleotides is as described in the U.S. Patent Office Manual of Patent Examining Procedure, section 2422, table 1. In this regard, the nucleotide designation "R" means guanine or adenine, "Y" means thymine (uracil if RNA) or cytosine; and "M" means adenine or cytosine. An oligonucleotide may be used as a primer or as a probe.

As used herein, the term "nucleic acid" or "nucleic acid sequence" refers to an oligonucleotide, nucleotide or polynucleotide, and fragments or portions thereof, which may be single or double stranded, or partially double stranded and represent the sense or antisense strand. A nucleic acid may include DNA or RNA, and may be of natural or synthetic origin and may contain deoxyribonucleotides, ribonucleotides, or nucleotide analogs in any combination. Nucleic acid may comprise a detectable label. Although a sequence of the nucleic acids may be shown in the form of DNA, a person of ordinary skill in the art recognizes that the corresponding RNA sequence will have a similar sequence with the thymine being replaced by uracil i.e. "t" with "u".

Non-limiting examples of nucleic acid include a gene or gene fragment, genomic DNA, exons, introns, mRNA, tRNA, rRNA, ribozymes, cDNA, recombinant nucleic acid, branched nucleic acid, plasmids, vectors, isolated DNA of any sequence, isolated RNA of any sequence, synthetic nucleic acid, nucleic acid probes and primers. Nucleic acid may comprise modified nucleotides, such as methylated nucleotides and nucleotide analogs, uracyl, other sugars and linking groups such as fluororibose and thiolate, and nucleotide branches. A nucleic acid may be modified such as by conjugation, with a labeling component. Other types of modifications included in this definition are caps, substitution of one or more of the naturally occurring nucleotides with an analog, and introduction of chemical entities for attaching the polynucleotide to other molecules such as proteins, metal ions, labeling components, other nucleic acid or a solid support. Nucleic acid may include nucleic acid that has been amplified (e.g., using polymerase chain reaction).

"Genomic nucleic acid" as used herein, refers to the nucleic acid in a cell that is present in the cell chromosome(s) of an organism which contains the genes that encode the various proteins of the cells of that organism. A preferred type of genomic nucleic acid is that present in the nucleus of a eukaryotic cell. In a preferred embodiment, a genomic nucleic acid is DNA. Genomic nucleic acid can be double stranded or single stranded, or partially double stranded, or partially single stranded or a hairpin molecule. Genomic nucleic acid may be intact or fragmented (e.g., digested with restriction endonucleases or by sonication or by applying shearing force by methods known in the art). In some cases, genomic nucleic acid may include sequence from all or a portion of a single gene or from multiple genes, sequence from one or more chromosomes, or sequence from all chromosomes of a cell. As is well known, genomic nucleic acid includes gene coding regions, introns, 5' and 3' untranslated regions, 5' and 3' flanking DNA and structural segments such as telomeric and centromeric DNA, replication origins, and intergenic DNA. Genomic nucleic acid representing the total nucleic acid of the genome is referred to as "total genomic nucleic acid."

Genomic nucleic acid may be obtained by methods of extraction/purification from cellular or acellular material as is well known in the art. The ultimate source of genomic nucleic acid can be normal cells or may be cells that contain one or more mutations in the genomic nucleic acid, e.g., duplication, deletion, translocation, and transversion. Included in the meaning of genomic nucleic acid is genomic nucleic acid that has undergone recombination and may comprise rearranged genes. Also included in the meaning of genomic nucleic acid is genomic nucleic acid that has been subjected to an amplification step that increases the amount of the target sequence of interest sought to be detected relative to other nucleic acid sequences in the genomic nucleic acid. In some embodiments, genomic nucleic acid may be substantially purified from its natural environment. In another embodiment, genomic nucleic acid may not be purified from its natural environment. In some embodiments, genomic nucleic acid may be present in an environment comprising RNA, proteins such as in cell lysates, tissue homogenates.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization and washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

The term "complement" as used herein means the complementary sequence to a nucleic acid according to standard Watson/Crick pairing rules. A complement sequence can also be a sequence of RNA complementary to the DNA sequence or its complement sequence, and can also be a cDNA.

As used herein the term "at least a portion of" in the context of nucleic acid means at least 5, at least about 15, 20, 25, 30, 35, 40, 45, 50, 75, 100, 200, 300, 400, 500, or 1,000 contiguous nucleotides or more in length.

As used herein, the term "about," unless indicated otherwise, means in quantitative terms, plus or minus 10%.

BRIEF DESCRIPTION OF THE FIGURES

FIG. 1 shows the genomic nucleic acid sequence of a portion of the human FMR1 gene including the 5'-untranslated region (SEQ ID NO: 1).

FIGS. 6A-6C are electropherograms showing the results of assay sensitivity to detect low levels of full mutations in the 5'-UTR of FMR1 gene. DNA samples from normal males or females were mixed with affected males or females to give final concentrations of full mutation content as shown in each panel and were amplified using primers FMR1F and FMR1R and M13R in presence of 7-deaza-dGTP. The normal alleles show full scale low number repeat signal while the mutant alleles show stutter amplification. FIG. 6A) Set A, from mixed normal male (28 repeats) and affected male (850 repeats), shows detection of full mutation at 5% "mosaic" content. FIG. 6B) Set B, from mixed normal homozygous female (28/28 repeats) and affected female (19/450 repeats), shows detection of full mutation in female DNA at 1% indicated by the arrow in the electropherogram at the right. In this instance, the full mutation allele represents only 1 of the four alleles present in the mix, and is present at very low amounts in the low "mosaic" content. FIG. 6C) Set C, from mixed normal male (28 repeats) and affected male (853 repeats) shows "mosaic" detection from males at 10% "mosaic" content indicated by the arrow in the electropherogram at the right. The disappearance of the normal 28 repeat allele (right most arrow in <55 repeat segment) occurs as the % full mutation is increased.

FIG. 15 shows exemplary arrangement of CCG triplet sequences relative to each other in the primer.

FIG. 16 shows exemplary arrangement of CGG triplet sequences relative to each other in the primer.

FIG. 18A is an electropherogram showing the results CCG repeat-primed PCR assay using reverse primer FMR1R (SEQ ID NO: 3), forward primer FMR1F, and M13R in presence of 7-deazadGTP. FIG. 18B shows the reconfirmation of the results CCG repeat-primed PCR assay using the CSA method with gender confirmation.

FIG. 20A is an electropherogram showing a late migrating fragment on capillary electrophoresis as an evidence of full mutation in the FMR1 gene. FIG. 20B shows the size separation of restriction endonuclease digested fragments to indicate the methylation status of CGG repeat tract of the 5'-UTR of FMR1 gene. The appearance of additional DNA fragments (shown by arrow) along with the expected fragment sizes is indicative of heterogeneity in DNA methylation.

FIG. 21 shows an exemplary nucleic acid sequence of the 5'-UTR of FMR2 gene comprising the CCG repeats (SEQ ID NO: 75).

DETAILED DESCRIPTION OF THE INVENTION

Figure 2G:
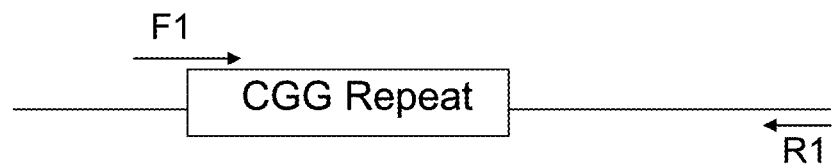
FIG. 2 A-K shows a schematic representation of the relative position of the primers for amplifying CGG repeat tract of 5'-UTR of FMR1 gene.
FIG. 2A shows a forward primer (F) and reverse primer (R1) hybridizing to 5'-UTR of FMR1 gene nucleotide sequences upstream and downstream of CGG repeat tract, respectively. The reverse primers R2 and R4, shown in FIG. 2B and 2D, respectively, hybridize to a portion of CGG repeat, the junction of 3'-end of CGG repeat tract and down stream sequences. The reverse primers R3 and R5, shown in FIG. 2C and 2E, respectively, hybridize randomly to the CGG repeat tract. Reverse primers R4 and R5, shown in FIG. 2D and 2E, respectively, further include a sequence with no homology to FMR1 gene. This sequence is complementary to primer R6 which can serve as a primer for subsequent amplification. The forward primers F1 and F3 shown in FIG. 2G and 2I, respectively, hybridize to a portion (technically the complement) of the CGG repeat and the junction of 5'-end of CGG tract and upstream sequences. The forward primers F2 and F4 shown in FIG. 2H and 2J, respectively, hybridize randomly to the CGG repeat sequence (technically the complement of this sequence). Forward primers F3 and F4 shown in FIG. 2K further include a sequence with no homology to FMR1 gene. This sequence is identical to primer F5 which can serve as a primer for subsequent amplification. After initial rounds of PCR, extended forward or reverse primers can themselves serve as both templates and primers. This results in various PCR product sizes giving the "stutter" pattern upon capillary electrophoresis.
Figure 2H:
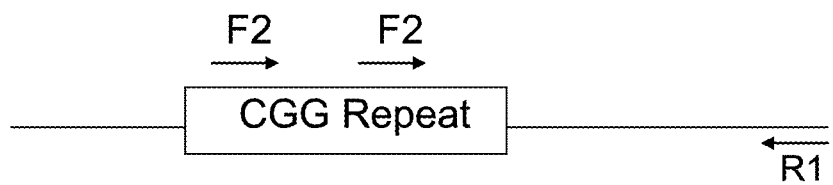
Figure 2I:
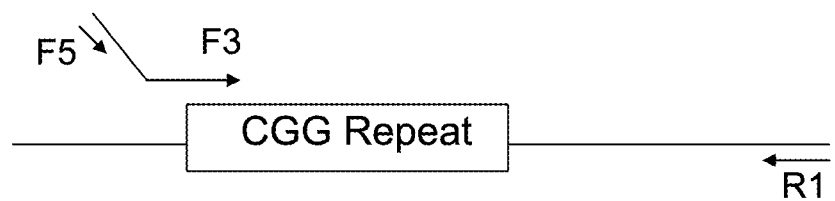
Figure 2J:
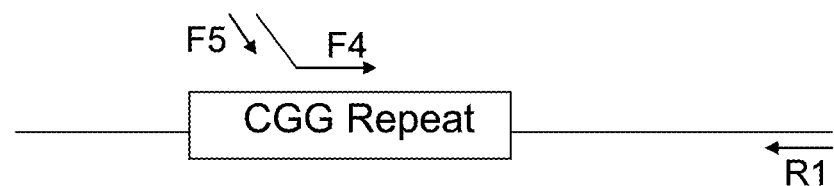
Figure 2K:
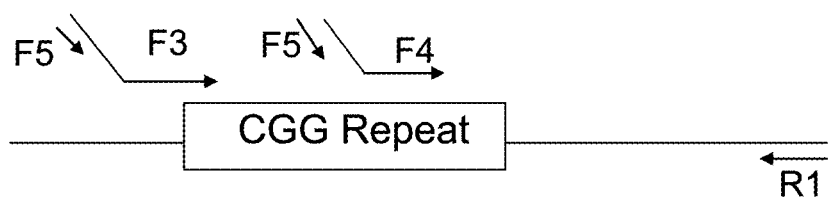

Repeat expansion disease includes any of about two dozen human diseases displaying Mendelian inheritance patterns shown to be caused by expansions of intrinsically polymorphic tandem repeats, mainly involving different trinucleotide motifs but also longer repetitive sequences up to 12-mers (Table 1). A characteristic of an allele containing an expanded tandem repeat is an excessive instability in successive generations (dynamic mutations). Furthermore, these alleles can differ in lengths among cell populations of the same organism (mosaicism). One type of repeat expansion disease is the trinucleotide repeat disorders (e.g., fragile X syndrome, myotonic dystrophy 1, etc.), the most abundant form of repeat expansion diseases. These diseases exhibit intergenerational repeat instability with a tendency towards further expansion of the tandem repeat. Increased repeat lengths in successive generations can lead to an earlier age of onset in affected individuals and/or an accentuation of clinical symptoms. The methods of the present invention which are experimentally exemplified for determining an expansion of the CGG repeat tract of the FMR1 gene also are applicable to detecting the same repeat tracts in genes associated with other diseases as shown in Table 1.

TABLE 1

Exemplary tandem repeat expansion diseases

| Disease (gene designation) | Protein | Tandem repeat sequence | Repeat Localization | Normal repeat range | Expanded repeat |
|---|---|---|---|---|---|
| Dentatorubral-pallidoluysian atrophy (DRPLA) | atrophin-1 | CAG | coding | 6-35 | 49-88 |
| Progressive myclonus epilepsy (EPM1)# | CSTB | CCCCGC CCCGCG | 5' UTR | 2-3 | 50-80 |
| Fragile XA-syndrome (FRAXA)* | FMR1 | CGG | 5' UTR | 5-44 | >230 |
| Fragile XE-syndrome (FMR1)* | FMR-2 | CCG | 5' UTR | 6-30 | >200 |
| Friedreich ataxia (FRDA)# | Frataxin | GAA | intronic | 7-34 | >100 |
| Huntington disease (huntingtin) | huntingtin | CAG | coding | 4-35 | 36-250 |
| Huntington disease-like 2 (JPH-3) | junctophilin-3 | CTG | coding | 6-27 | >40-60 |

TABLE 1-continued

Exemplary tandem repeat expansion diseases

| Disease (gene designation) | Protein | Tandem repeat sequence | Repeat Localization | Normal repeat range | Expanded repeat |
|---|---|---|---|---|---|
| Spinobulbar musc. atrophy, Kennedy disease (AR)* | androgen rec. | CAG | coding | 9-36 | 38-62 |
| Myotonic dystrophy 1 (DM1) | DMPK/SIX5 | CTG | 3' UTR | 5-37 | >50 |
| Myotonic dystrophy 2 (DM2) | ZNF9 | CCTG | intronic | 10-26 | 175->11000 |
| Spinocerebellar ataxia 1 (SCA1) | ataxin-1 | CAG | coding | 6-44 | 39-82 |
| Spinocerebellar ataxia 2 (SCA2) | ataxin-2 | CAG | coding | 15-31 | 36-63 |
| Spinocerebellar ataxia 3, Machado-Joseph disease (SCA3) | Ataxin-3 | CAG | coding | 12-40 | 55-84 |
| Spinocerebellar ataxia 6 (SCA6) | CACNA1A | CAG | coding | 4-18 | 21-33 |
| Spinocerebellar ataxia 7 (SCA7) | Ataxin-7 | CAG | coding | 4-35 | 37-306 |
| Spinocerebellar ataxia 8 (SCA8) | not known | CTG | 3' UTR | 16-37 | 110-250 |
| Spinocerebellar ataxia 10 (SCA10) | Ataxin-10 | ATTCT | intronic | 10-22 | 800-4600 |
| Spinocerebellar ataxia 12 (SCA12) | PP2A-PR55B | CAG | promotor | 7-28 | 66-78 |
| Spinocerebellar ataxia 17 (SCA17) | TBP | CAG | coding | 25-42 | 47-63 |
| Oculopharyngeal muscular dystrophy (PABPN1) | PABPN1 | GCG | coding | 6 | 7-13 |
| Synpolydactyly, type II (HOXD13) | HOXD13 | GCN | coding | 15 | 22-24 |

\* = X chromosome;
\# = autosomal recessive;
undesignated = autosomal dominant

Methods of detecting a particular nucleic acid segment of interest in a sample of nucleic acids are provided. In particular embodiments, the particular nucleic acid segment of interest is a tandem repeat and the method is used to determine information about the size of such tandem repeat. In some embodiments, the methods are useful for detecting CGG repeats in the FMR1 gene. In some embodiments, the methods are useful for detecting CCG repeats in the FMR2 gene. The methods are useful in detecting over 2,000 CGG and/or CCG repeats in the highly GC rich, CGG containing 5'-UTR the region of FMR1 gene and CCG containing 5'-UTR the region of FMR2 gene respectively. The methods involve amplifying the CGG containing 5'-UTR region of the FMR1 gene and/or CCG containing 5'-UTR region of the FMR2 gene followed by detecting the amplicons. The methods allow detection of CGG expansions and full mutations in FMR1 gene of both males and females. The methods also allow detection of CCG expansions and full mutations in FMR2 gene of both males and females. The methods can be used on small sample amounts such as a blood spot that are typically available in newborn screening programs. The methods are useful to determine the frequency of Fragile X syndrome premutations and full mutations in non-selected unbiased populations undergoing routine carrier screening.

FMR1 Gene

Human FMR1 gene is located in chromosome X. Fragile X syndrome (FXS) is caused by expansion and subsequent methylation of the CGG trinucleotide repeat in the FMR1 5'-untranslated region (5'-UTR). Typically, normal repeat lengths are between 5-44, intermediate are between 45-54, premutation are between 55-200 CGG, while full mutation are greater than 200. Exemplary FMR1 genomic nucleic acid sequence comprising the 5'-UTR include, but is not limited to, sequence in GenBank accession number NG_007529 and in L29074. These sequences are incorporated herein by reference. Exemplary FMR1 nucleic acid sequence comprising the 5'-UTR, as well as the start codon and a portion of the beginning of the coding sequence as set forth in GenBank accession number L29074 is disclosed as SEQ ID NO: 12 in US Patent Application Publication 2008/0113355. The sequence of SEQ ID NO: 12 of US 2008/0113355 is incorporated herein by reference. The CGG repeat tract starts at position 13833 and ends in position 13962 and is depicted herein in SEQ ID NO: 1.

FMR2 Gene

Human FMR2 gene is located in chromosome Xq28, 600 kb distal to FMR1 gene. The FMR2 (FRAXE) mutation is an expansion of the CCG containing repeats in the 5'-UTR of FMR2 gene that result in the methylation of a nearby CpG island. Typically, normal CCG repeat lengths are between 6-30, intermediate are between 31-60, permutations are between 61-200 and full mutations are greater than 200. Exemplary FMR1 genomic nucleic acid sequence comprising the 5'-UTR include, but is not limited to, sequence in GenBank accession number AH005569. This sequence is incorporated herein by reference. An exemplary sequence of the 5'-UTR of FMR2 gene comprising the CCG repeats is shown in FIG. 21 and depicted as SEQ ID NO: 75.

Biological Sample Collection and Preparation

The biological sample may be obtained from a stage of life such as a fetus, young adult, adult, and the like. In one example, subjects are humans being tested for the existence expanded CGG repeats in the 5'-UTR of FMR1 gene. In another example, subjects are humans being tested for the existence expanded CCG repeats in the 5'-UTR of FMR2 gene. In one embodiment, the sample may be obtained from an individual who is suspected of having a fragile X syndrome. In another embodiment, the sample may be obtained from a healthy individual who is assumed of having no disease, or a genetic abnormality. In another embodiment, the sample may be obtained from an individual suspected of being a carrier of fragile X syndrome but not affected by the disease.

Sample Collection: Methods of obtaining samples are well known to those of skill in the art and include, but are not limited to, aspirations, tissue sections, drawing of blood or other fluids, surgical or needle biopsies, collection of paraffin embedded tissue, collection of body fluids, collection of stool, and the like.

The methods can be used to assist with prenatal diagnosis of fragile X or other triplet repeat disease using any type of embryonic or fetal cell or nucleic acid containing body fluid. Fetal cells can be obtained through the pregnant female, or from a sample of an embryo. Thus, fetal cells are present in amniotic fluid obtained by amniocentesis, chorionic villi aspirated by syringe, percutaneous umbilical blood, a fetal skin biopsy, a blastomere from a four-cell to eight-cell stage embryo (pre-implantation), or a trophectoderm sample from a blastocyst (pre-implantation or by uterine lavage).

Genomic nucleic acid: In one embodiment, nucleic acid is genomic nucleic acid. Genomic nucleic acid may be intact. In another embodiment, genomic nucleic acid may be fragmented (e.g., digested with restriction endonucleases, or by sonication or by applying shearing force by methods known in the art).

Sample Preparation: The nucleic acid (DNA or RNA) may be isolated from the sample according to any methods well known to those of skill in the art. If necessary, the sample may be collected or concentrated by centrifugation and the like. The sample may be subjected to lysis, such as by treatments with enzymes, heat, surfactants, ultrasonication, or a combination thereof. The lysis treatment is performed in order to obtain a sufficient amount of nucleic acid. The sample may be subjected to liquid chromatography to partially purify the genomic nucleic acid.

Suitable DNA isolation methods include phenol and chloroform extraction. See Maniatis et al., Molecular Cloning, A Laboratory Manual, 2d, Cold Spring Harbor Laboratory Press, page 16.54 (1989). Numerous commercial kits also yield suitable DNA including, but not limited to, QIAamp™ mini blood kit, Agencourt Genfind™, Roche Cobas® Roche MagNA Pure® or phenol:chloroform extraction using Eppendorf Phase Lock Gels®.

Total DNA (e.g., genomic, mitochondrial, microbial, viral,) can be purified from any biological sample using commercially available kits e.g. QIAamp DNA and QIAamp DNA Blood mini kits, Qiagen M96 robot and reagents, Qiagen Gentra robot and reagents, and Qiagen 9604 reagents (Qiagen, Valencia, Calif.). In one example, blood can be spotted on Guthrie cards. Blood spots can be punched from each card using BSD1000 GenePunch Instrument and DNA was extracted using Qiagen BioSprint reagents.

Genomic DNA may be isolated from cells or tissues using standard methods, see, e.g., Sambrook, et al., 1989, Molecular Cloning: A Laboratory Manual, Second Edition, Cold Spring Harbor Press, Plainview, N.Y.

In another embodiment, sample nucleic acid may be mRNA or cDNA generated from mRNA or total RNA. RNA can be isolated from cells or tissue samples using standard techniques, see, e.g., Sambrook, et al., 1989, Molecular Cloning: A Laboratory Manual, Second Edition, Cold Spring Harbor Press, Plainview, N.Y. In addition, kits for isolating mRNA and synthesizing cDNA are commercially available e.g. RNeasy Protect Mini kit, RNeasy Protect Cell Mini kit from Qiagen.

Nucleic acid need not be extracted, but may be made available by suitable treatment of cells or tissue such as described in U.S. Pat. No. 7,521,213.

Nucleic Acid Amplification

Nucleic acid comprising triplet repeat sequences can be amplified by various methods known to the skilled artisan. In one embodiment, nucleic acid comprising CGG repeat sequences of the FMR1 gene or nucleic acid comprising CCG repeat sequences of the FMR 2 gene can be amplified by PCR. PCR methods to amplify CGG repeats and CCG repeats include, but are not limited to, nested PCR which involves a set of outer primer and a set of inner primer, semi-nested PCR which involves a common primer, an outward primer and an inner primer, and standard PCR with a primer pair. Efficient amplification of the GC rich CGG repeat and CCG repeat containing 5-UTR region of FMR 1 and FMR 2 respectively will depend on several parameters including, but not limited to, primer location, primer sequence, nucleotide concentrations, use of a dGTP analogue such as 7-deaza-2-deoxyGTP, and inclusion of additives to increase the yield, specificity and consistency.

Primer Locations and Primer Sequences:

Primer Locations for the Detection of CGG Repeats in FMR1 Gene

In one embodiment, the forward and reverse primers may hybridize to regions in the 5'-UTR of the FMR1 gene outside the CGG repeat sequence as shown in FIG. 2A. In another embodiment, the reverse primer may comprise one or more CCG triplet sequences and include sequence complementary to the junction sequence of the 3'-end of the CGG repeat tract and flanking sequence and a portion of the sequence downstream of the CGG repeat tract as shown in FIG. 2B. One or more CCG triplets will hybridize to the CGG repeats and permit amplification of the CGG repeat sequences. In yet another embodiment, the reverse primer may comprise one or more CCG triplet sequences without any flanking and junction sequences such that the reverse primers may hybridize randomly to the CGG repeat sequence and initiate DNA synthesis to generate a broad spectrum of amplicons of varying length or stutter. Exemplary reverse primers are shown in FIG. 2A-F.

In another embodiment, the forward primer may comprise one or more CGG triplet sequences, the junction sequence of the 5'-end of the CGG repeat tract and flanking sequence and a portion of the sequence upstream of the CGG repeat tract as shown in FIG. 2G. One or more CGG triplets will hybridize to the CCG repeats of the complementary strand and permit amplification of the CGG repeat sequences. In yet another embodiment, the forward primer may comprise one or more CGG triplet sequences without any flanking and junction sequences such that the forward primers may hybridize randomly to the complementary strand of CGG repeat sequence and initiate DNA synthesis to generate a broad spectrum of amplicons of varying length or stutter. Exemplary forward primers are shown in FIG. 2G-K.

Primer Locations for the Detection of CCG Repeats in FMR2 Gene

In one embodiment, the forward and reverse primers may hybridize to regions in the 5'-UTR of the FMR2 gene outside the CCG repeat sequence as shown in FIG. 22A. In another embodiment, the reverse primer may comprise one or more CGG triplet sequences and include sequence complementary to the junction sequence of the 3'-end of the CCG repeat tract and flanking sequence and a portion of the sequence downstream of the CCG repeat tract as shown in FIG. 22B. One or more CGG triplets will hybridize to the CCG repeats and permit amplification of the CCG repeat sequences. In yet another embodiment, the reverse primer may comprise one or more CGG triplet sequences without any flanking and junction sequences such that the reverse primers may hybridize randomly to the CCG repeat sequence and initiate DNA synthesis to generate a broad spectrum of amplicons of varying length or stutter. Exemplary reverse primers are shown in FIG. 22A-F.

Figure 22G:
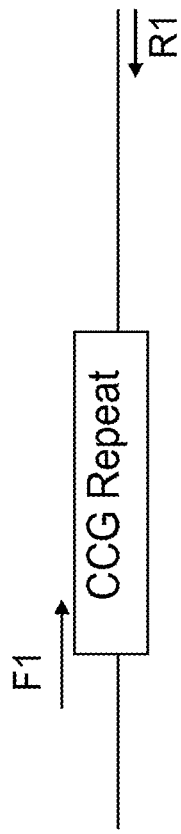
FIG. 22 A-K shows a schematic representation of the relative position of the amplification primers for amplifying CCG repeat tract in the 5'-UTR of FMR2 gene.
FIG. 22A shows a forward primer (F) and reverse primer (R1) hybridizing to 5'-UTR of FMR2 gene nucleotide sequences upstream and downstream of CCG repeat tract respectively. The reverse primers R2 and R4, shown in FIG. 22B and 22D, respectively, hybridize to a portion of CCG repeat, the junction of 3'-end of CCG repeat tract and down stream sequences. The reverse primers R3 and R5, shown in FIG. 22C and 22E, respectively, hybridize randomly to the CCG repeat tract. Reverse primers R4 and R5, shown in FIG. 22D and 22E, respectively, further include a sequence with no homology to FMR2 gene. This sequence is complementary to primer R6 which can serve as a primer for subsequent amplification. The forward primers F1 and F3 shown in FIG. 22G and 22I, respectively, hybridize to a portion (technically the complement) of the CCG repeat and the junction of 5'-end of CCG tract and upstream sequences. The forward primers F2 and F4 shown in FIG. 22H and 22J, respectively, hybridize randomly to the CCG repeat sequence (technically the complement of this sequence). Forward primers F3 and F4 shown in FIG. 22K further include a sequence with no homology to FMR2 gene. This sequence is identical to primer F5 which can serve as a primer for subsequent amplification. After initial rounds of PCR, extended forward or reverse primers can themselves serve as both templates and primers. This results in various PCR product sizes giving the "stutter" pattern upon capillary electrophoresis.
Figure 22H:
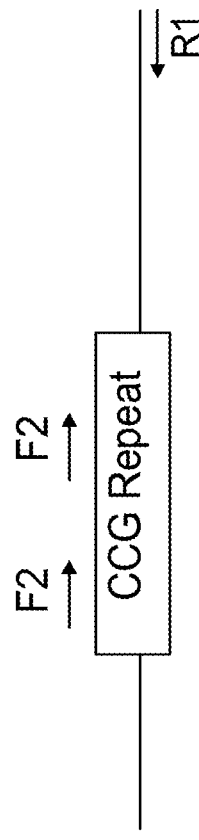
Figure 22I:
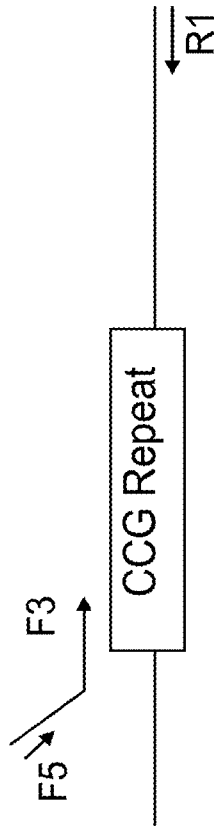
Figure 22J:
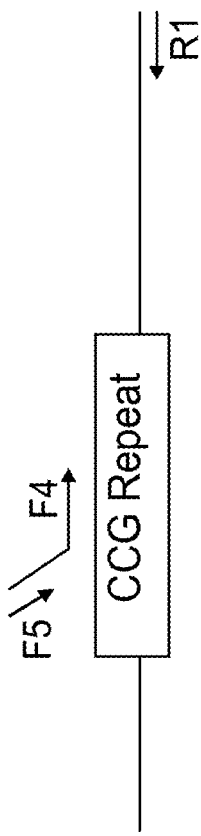
Figure 22K:
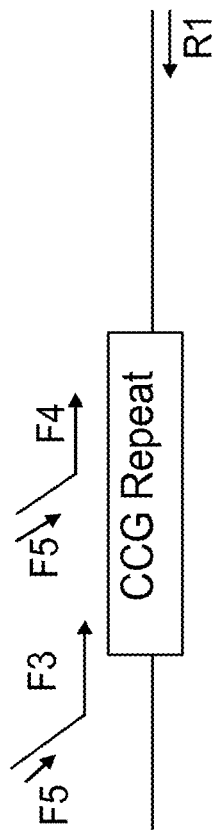

In another embodiment, the forward primer may comprise one or more CCG triplet sequences, the junction sequence of the 5'-end of the CCG repeat tract and flanking sequence and a portion of the sequence upstream of the CCG repeat tract as shown in FIG. 22G. One or more CCG triplets will hybridize to the CGG repeats of the complementary strand and permit amplification of the CCG repeat sequences. In yet another embodiment, the forward primer may comprise one or more CCG triplet sequences without any flanking and junction sequences such that the forward primers may hybridize randomly to the complementary strand of CCG repeat sequence and initiate DNA synthesis to generate a broad spectrum of amplicons of varying length or stutter. Exemplary forward primers are shown in FIG. 22G-K.

In some embodiments, the one or more primers can be labeled with a detectable label. Exemplary detectable label includes but not limited to fluorophores, radiolabels, chemiluminescent compound, colorimetric labels (e.g., colloidal gold), magnetic labels (e.g., Dynabeads™), biotin, digoxigenin, haptens, proteins, enzymes.

In some embodiments, the forward or the reverse or both primers may comprise degenerate bases. In some embodiments, the forward or the reverse or both primers may comprise universal bases. Exemplary universal bases include 3-nitropyrrole, 5'-nitroindole.

In some embodiments, the forward or the reverse or both primers may further comprise an optional sequence at the 5'-end that has no homology with the target sequence of SEQ ID NO: 1 or SEQ ID NO: 75 (see, FIGS. 2 D-F, 2 I-K, 22 D-F, and 22 I-K). Such 5'-end sequences can be 6-50 nucleotides in length, 10-30 nucleotides in length, or 15-25 nucleotides in length. In one embodiment, the optional 5'-end sequence may be from bacteriophage M13 or from T7 promoter. In another embodiment, the optional 5'-end sequence may be a random sequence. After a few rounds of amplification, the resulting amplicons will comprise the optional 5'-end sequence. These 5'-end sequences can be utilized as template for further round of amplification using primers hybridizing to these 5'-end sequences. Exemplary M13 5'-end sequence is shown below and listed as SEQ ID NO: 11.

```
                                           (SEQ ID NO: 11)
CAGGAAACAGCTATGACC
```

Exemplary T7 promoter sequence is shown below and listed as SEQ ID NO: 70.

```
                                           (SEQ ID NO: 70)
TAATACGACTCACTATAGGG
```

In some embodiments, the PCR reaction may be a seminested PCR, such that there is a common forward primer and an inner and outer reverse primer as shown in FIG. 2F and 22F.

Primers flanking the CGG repeat region of FMR1 gene: Methods for designing suitable primers that hybridize to the 5'-UTR of the FMR1 gene as exemplified in SEQ ID NO: 1 (or SEQ ID NO: 12 of US 2008/0113355) are known in the art such as H. Erlich, PCR Technology, Principles and Application for DNA Amplification (1989). In one embodiment, the 5'-primer (forward primer) can hybridize to the 5'-UTR within 500 or fewer nucleotides, within 300 or fewer nucleotides, within 200 or fewer nucleotides, within 100 or fewer nucleotides, within 50 or fewer nucleotides, within 25 or fewer nucleotides 5' of nucleotide position of 13833 of SEQ ID NO: 1. In another embodiment, the 3'-primer (reverse primer) can hybridize to the 5'-UTR within 500 or fewer nucleotides, within 300 or fewer nucleotides, within 200 or fewer nucleotides, within 100 or fewer nucleotides, within 50 or fewer nucleotides, within 25 or fewer nucleotides of 3' of nucleotide position of 13962 of SEQ ID NO: 1. Exemplary primers hybridizing to 5'-UTR flanking the CGG repeat region of FMR1 gene are provided below:

```
Forward:
                                           (SEQ ID NO: 12)
5'-GCTCAGCTCCGTTTCGGTTTCACTTCCGGT-3'

Reverse:
                                           (SEQ ID NO: 13)
5-AGCCCCGCACTTCCACTTTCGGTTTCACTTCCGGT-3'
```

Primers flanking the CCG repeat region of FMR2 gene: Methods for designing suitable primers that hybridize to the 5'-UTR of the FMR2 gene as exemplified in SEQ ID NO: 75 are known in the art such as H. Erlich, PCR Technology, Principles and Application for DNA Amplification (1989). In one embodiment, the 5'-primer (forward primer) can hybridize to the 5'-UTR within 500 or fewer nucleotides, within 300 or fewer nucleotides, within 200 or fewer nucleotides, within 100 or fewer nucleotides, within 50 or fewer nucleotides, within 25 or fewer nucleotides 5' of nucleotide position of 21 of SEQ ID NO: 75. In another embodiment, the 3'-primer (reverse primer) can hybridize to the 5'-UTR within 500 or fewer nucleotides, within 300 or fewer nucleotides, within 200 or fewer nucleotides, within 100 or fewer nucleotides, within 50 or fewer nucleotides, within 25 or fewer nucleotides of 3' of nucleotide position of 65 of SEQ ID NO: 75. Exemplary primers hybridizing to 5'-UTR flanking the CCG repeat region of FMR2 gene are provided below:

Forward:
(SEQ ID NO: 76)
5'-CGCCGCCTGTGCAGCCGCTG-3'

Reverse:
(SEQ ID NO: 77)
5-GCCCCGGCTGCCGCGCCGCG-3'

Reverse primers with CCG triplet sequences for detecting CGG repeat tract in the 5'-UTR of FMR1 gene: Reverse primers with one or more CCG triplet sequences will hybridize to the CGG repeats sequences and permit amplification of the repeat region. The reverse primers may vary in the number of CCG triplet sequences from 1-40 CCG triplets. In some embodiments, the primers may comprise at least: 2, 3, 4, 5, 6, 7, 8, 9, 10, 11, 12, 13, 14, 15 or more CCG triplets. In some embodiments, the primers may comprise at least 10 consecutive CCG triplets. In some embodiments, the primers may comprise less than three CCG triplets. In some embodiments, the primers may comprise less than three consecutive CCG triplets. In one embodiment, the primers comprise two consecutive CCG triplets. In some embodiments, the primers may comprise at least two sets of two consecutive CCG triplets: $(CCG)_2$. In some embodiments, at least two sets of two consecutive CCG triplets are separated from each other by at least one nucleotide. In some embodiments, the linking nucleotides can be A or T. In some embodiments, the nucleotides linking the two consecutive CCG triplets $(CCG)_2$ may form a stem loop structure. In some embodiments, the primers may comprise two consecutive CCG triplets $(CCG)_2$ and additional nucleotides at the 5'- and 3'-end. In some embodiments, two sets of two consecutive CCG triplets $(CCG)_2$ are linked to each other through non-phosphodiester linkage. Exemplary non-nucleotide linkers include C4, C6, C8, C10 linkers, polyethylene glycol (PEG) linkers: $PEG_4$, $PEG_6$, $PEG_{10}$, $PEG_{12}$, peptide nucleic acid linkage, phosphorothioester linkage. Exemplary arrangements of CCG triplets relative to each other are shown in FIG. 15. Optionally the primers comprising one or more CCG triplets of FIG. 15 may further comprise a sequence at the 5'-end that has at least 90% homology to the sequence directly downstream (i.e. at the 3'-end) of the CGG repeat tract. In some embodiments, such sequence can be at least 3, 5, 10 or more nucleotides.

In some embodiments, reverse primers comprising one or more CCG triplets may further comprise an optional sequence at the 5'-end that has no homology with the target sequence of SEQ ID NO: 1. In some embodiments, the optional sequence at the 5'-end that has no homology to human genome. In some embodiments, reverse primers comprising one or more CCG triplets may comprise a second portion and a third portion at the 5'-end of CCG triplets segment such that the second portion comprises a sequence that has at least 90% homology to the sequence directly downstream (i.e. at the 3'-end) of the CGG repeat tract and the third portion, which is at the 5'-end of the second portion, comprises a sequence that has no homology with the target sequence of SEQ ID NO: 1 (or any of the FMR1 gene).

Exemplary reverse primer sequences comprising CCG triplets are shown in the table below.

TABLE 2

Reverse primers having one or more CCG triplets

| Reverse Primer Sequence | SEQ ID NO: |
|---|---|
| CGCCGCCGCC | 14 |
| CCGCCGACCGCCG | 15 |
| CCGCCGTCCGCCG | 16 |
| CCGCCGGCCGCCG | 17 |
| CCGCCGCCCGCCG | 18 |
| CGCCGCCGACGCCGCCGCC | 19 |
| CGCCGCCGTCGCCGCCGCC | 20 |
| CGCCGCCGGCGCCGCCGCC | 21 |
| CGCCGCCGCCCGCCGCC | 22 |
| CTCGAGGCCCAGCCGCCG | 23 |
| CTCGAGGCCCAGCCGTCGCCG | 24 |
| CTCGAGGCCCAGCCGACGCCG | 25 |
| CTCGAGGCCCAGCCGGCGCCG | 26 |
| CAGGAAACAGCTATGACCCGCCG | 27 |
| CAGGAAACAGCTATGACGCCGCCGCC | 28 |
| CAGGAAACAGCTATGACCCGCCGACCGCCG | 29 |
| CAGGAAACAGCTATGACCCGCCGTCCGCCG | 30 |
| CAGGAAACAGCTATGACCCGCCGGCCGCCG | 31 |
| CAGGAAACAGCTATGACCCGCCGCCCGCCG | 32 |
| CAGGAAACAGCTATGACGCCGCCGACGCCGCCGCC | 33 |
| CAGGAAACAGCTATGACGCCGCCGTCGCCGCCGCC | 34 |
| CAGGAAACAGCTATGACGCCGCCGGCGCCGCCGCC | 35 |
| CAGGAAACAGCTATGACGCCGCCGCCCGCCGCC | 36 |
| CAGGAAACAGCTATGACCTCGAGGCCCACCGCCG | 37 |
| CAGGAAACAGCTATGACCTCGAGGCCCAGCCGTCGCCGCCG | 38 |
| CAGGAAACAGCTATGACCTCGAGGCCCAGCCGACGCCGCCG | 39 |
| CAGGAAACAGCTATGACCTCGAGGCCCAGCCGGCGCCGCCG | 40 |
| CAGGAAACAGCTATGACCCTCGAGGCCCAGCCGCCGCCGCCGCC | 71 |
| CAGGAAACAGCTATGACCCTCGAGGCCCAGCCGCCGCCGCCGCCGCC | 72 |
| CAGGAAACAGCTATGACCCTCGAGGCCCAGCCGCCGCC | 73 |
| CAGGAAACAGCTATGACCCTCGAGGCCCAGCCGCCG | 74 |

Forward primers with CGG triplet sequences for detecting CGG repeat tract in the 5'-UTR of FMR1 gene: Forward primers with one or more CGG triplet sequences will hybridize to the complementary strand of CGG repeats sequences and permit amplification of the repeat region. The forward primers may vary in the number of CGG triplet sequences from 1-40 CGG triplets. In some embodiments, the primers may comprise at least: 2, 3, 4, 5, 6, 7, 8, 9, 10, 11, 12, 13, 14, 15 or more CGG triplets. In some embodiments, the primers may comprise at least 10 consecutive CGG triplets. In some embodiments, the primers may comprise less than three CGG triplets. In some embodiments, the primers may comprise less than three consecutive CGG triplets. In one embodiment, the primers comprise two consecutive CGG triplets. In some embodiments, the primers may comprise at least two sets of two consecutive CGG triplets: (CGG)$_2$. In some embodiments, at least two sets of two consecutive CGG triplets are separated from each other by at least one nucleotide. In some embodiments, the linking nucleotides can be A or T. In some embodiments, the nucleotides linking the two consecutive CGG triplets (CGG)$_2$ may form a stem loop structure. In some embodiments, the primers may comprise two consecutive CGG triplets (CGG)$_2$ and additional nucleotides at the 5'- and 3'-end. In some embodiments, two sets of two consecutive CGG triplets (CGG)$_2$ are linked to each other through non-phosphodiester linkage. Exemplary non-nucleotide linkers include C4, C6, C8, C10 linkers, polyethylene glycol (PEG) linkers: PEG$_4$, PEG$_6$, PEG$_{10}$, PEG$_{12}$, peptide nucleic acid linkage, phosphorothoioester linkage. Exemplary arrangements of CGG triplets are shown in FIG. 16. Optionally the primers comprising one or more CGG triplets of FIG. 16 may further comprise a sequence at the 5'-end that has at least 90% homology to the sequence directly upstream (i.e. at the 5'-end) of the CGG repeat tract. In some embodiments, such sequence can be at least 3, 5, 10 or more nucleotides. In some embodiments, forward primers comprising one or more CGG triplets of FIG. 16 may further comprise an optional sequence at the 5'-end that has no homology with the target sequence of SEQ ID NO: 1. In some embodiments, the optional sequence at the 5'-end that has no homology to human genome. In some embodiments, forward primers comprising one or more CGG triplets of FIG. 16 may comprise a second portion and a third portion at the 5'-end of one or more CGG triplets such that the second portion comprises a sequence that has at least 90% homology to sequence directly upstream (i.e. at the 5'-end) of the CGG repeat tract, and the third portion, which is at the 5'-end of the second portion, comprises a sequence that has no homology with the target sequence of SEQ ID NO: 1 (or any of the FMR1 gene).

Exemplary forward primer sequences comprising CCG triplets are shown in the table below.

TABLE 3

| Forward primers having one or more CGG triplets | |
|---|---|
| Forward Primer Sequence | SEQ ID NO: |
| CGCGGCGGCG | 41 |
| CGGCGGACGGCGG | 42 |
| CGGCGGTCGGCGG | 43 |
| CGGCGGGCGGCGG | 44 |
| CGGCGGCCGGCGG | 45 |

TABLE 3-continued

| Forward primers having one or more CGG triplets | |
|---|---|
| Forward Primer Sequence | SEQ ID NO: |
| GGCGGCGGAGGCGGCGGCG | 46 |
| GGCGGCGGTGGCGGCGGCG | 47 |
| GGCGGCGGGGCGGCGGCG | 48 |
| GGCGGCGGCCGGCGGCG | 49 |
| CGTGCIGCAGCGCGGCGG | 50 |
| CGTGCIGCAGCGCGGTGGCGG | 51 |
| CGTGCIGCAGCGCGGAGGCGG | 52 |
| CGTGCIGCAGCGCGGGGGCGG | 53 |
| CAGGAAACAGCTATGACCGGCGG | 54 |
| CAGGAAACAGCTATGACCGGCGGCG | 55 |
| CAGGAAACAGCTATGACCGGCGGACGGCGG | 56 |
| CAGGAAACAGCTATGACCGGCGGTCGGCGG | 57 |
| CAGGAAACAGCTATGACCGGCGGCCGGCGG | 58 |
| CAGGAAACAGCTATGACCGGCGGGCGGCGG | 59 |
| CAGGAAACAGCTATGACCCGGCGGAGGCGGCGGCG | 60 |
| CAGGAAACAGCTATGACCCGGCGGTGGCGGCGGCG | 61 |
| CAGGAAACAGCTATGACCCGGCGGGGGCGGCGGCG | 62 |
| CAGGAAACAGCTATGACCCGGCGGCCGGCGGCG | 63 |
| CAGGAAACAGCTATGACCCGGCGGTCGGCGGCG | 64 |
| CAGGAAACAGCTATGACCCGGCGGGCGGCGGCG | 65 |
| CAGGAAACAGCTATGACCCGGCGGACGGCGGCG | 66 |
| CAGGAAACAGCTATGACCCGTGCIGCAGCGCGGTGGCGGCGG | 67 |
| CAGGAAACAGCTATGACCCGTGCIGCAGCGCGGAGGCGGCGG | 68 |
| CAGGAAACAGCTATGACCCGTGCIGCAGCGCGGGGGCGGCGG | 69 |

Reverse primers with CGG triplet sequences for detecting CCG repeat tract in the 5'-UTR of FMR2 gene: Reverse primers with one or more CGG triplet sequences will hybridize to the CCG repeats sequences and permit amplification of the repeat region. The reverse primers may vary in the number of CGG triplet sequences from 1-40 CGG triplets. In some embodiments, the primers may comprise at least: 2, 3, 4, 5, 6, 7, 8, 9, 10, 11, 12, 13, 14, 15 or more CGG triplets. In some embodiments, the primers may comprise at least 10 consecutive CGG triplets. In some embodiments, the primers may comprise less than three CGG triplets. In some embodiments, the primers may comprise less than three consecutive CGG triplets. In one embodiment, the primers comprise two consecutive CGG triplets. In some embodiments, the primers may comprise at least two sets of two consecutive CGG triplets: (CGG)$_2$. In some embodiments, at least two sets of two consecutive CGG triplets are separated from each other by at least one nucleotide. In some embodiments, the linking nucleotides can be A or T. In some embodiments, the nucleotides linking the two consecutive CGG triplets (CGG)$_2$ may form a stem loop structure. In some embodiments, the primers may comprise two consecutive CGG triplets (CGG)$_2$ and additional nucleotides at the 5'- and 3'-end. In some embodiments, two sets of two consecutive CGG triplets (CGG)$_2$ are linked to each other through non-phosphodiester linkage. Exemplary non-nucleotide linkers include C4, C6, C8, C10 linkers, polyethylene glycol (PEG) linkers: PEG$_4$, PEG$_6$, PEG$_{10}$, PEG$_{12}$, peptide nucleic acid linkage, phosphorothoioester linkage. Exemplary arrangements of CGG triplets are shown in FIG. 16. Optionally the primers comprising one or more CGG triplets of FIG. 16 may further comprise a sequence at the 5'-end that has at least 90% homology to the sequence directly downstream (i.e. at the 3'-end) of the CCG repeat tract. In some embodiments, such sequence can be at least 3, 5, 10 or more nucleotides. In some embodiments, reverse primers comprising one or more CGG triplets of FIG. 16 may further comprise an optional sequence at the 5'-end that has no homology with the target sequence of SEQ ID NO: 75. In some embodiments, the optional sequence at the 5'-end that has no homology to human genome. In some embodiments, reverse primers comprising one or more CGG triplets of FIG. 16 may comprise a second portion and a third portion at the 5'-end of one or more CGG triplets such that the second portion comprises a sequence that has at least 90% homology to sequence directly downstream (i.e. at the 3'-end) of the CCG repeat tract, and the third portion, which is at the 5'-end of the second portion, comprises a sequence that has no homology with the target sequence of SEQ ID NO: 75 (or any of the FMR2 gene).

Exemplary reverse primer sequences comprising CGG triplets for detecting CCG repeat tract in the 5'-UTR of FMR2 gene can be any of the CGG triplet containing forward primers used to detect CCG repeat tract in the 5'-UTR of FMR1 gene as listed in Table 3 above.

Forward primers with CCG triplet sequences for detecting CCG repeat tract in the 5'-UTR of FMR2 gene: Forward primers with one or more CCG triplet sequences will hybridize to the complementary strand of CCG repeats sequences and permit amplification of the repeat region. The forward primers may vary in the number of CCG triplet sequences from 1-40 CCG triplets. In some embodiments, the primers may comprise at least: 2, 3, 4, 5, 6, 7, 8, 9, 10, 11, 12, 13, 14, 15 or more CCG triplets. In some embodiments, the primers may comprise at least 10 consecutive CCG triplets. In some embodiments, the primers may comprise less than three CCG triplets. In some embodiments, the primers may comprise less than three consecutive CCG triplets. In one embodiment, the primers comprise two consecutive CCG triplets. In some embodiments, the primers may comprise at least two sets of two consecutive CCG triplets: (CCG)$_2$. In some embodiments, at least two sets of two consecutive CCG triplets are separated from each other by at least one nucleotide. In some embodiments, the linking nucleotides can be A or T. In some embodiments, the nucleotides linking the two consecutive CCG triplets (CCG)$_2$ may form a stem loop structure. In some embodiments, the primers may comprise two consecutive CCG triplets (CCG)$_2$ and additional nucleotides at the 5'- and 3'-end. In some embodiments, two sets of two consecutive CCG triplets (CCG)$_2$ are linked to each other through non-phosphodiester linkage. Exemplary non-nucleotide linkers include C4, C6, C8, C10 linkers, polyethylene glycol (PEG) linkers: PEG$_4$, PEG$_6$, PEG$_{10}$, PEG$_{12}$, peptide nucleic acid linkage, phosphorothoioester linkage. Exemplary arrangements of CCG triplets relative to each other are shown in FIG. 15. Optionally the primers comprising one or more CCG triplets of FIG. 15 may further comprise a sequence at the 5'-end that has at least 90% homology to the sequence directly upstream (i.e. at the 5'-end) of the CCG repeat tract. In some embodiments, such sequence can be at least 3, 5, 10 or more nucleotides.

In some embodiments, forward primers comprising one or more CCG triplets may further comprise an optional sequence at the 5'-end that has no homology with the target sequence of SEQ ID NO: 75. In some embodiments, the optional sequence at the 5'-end that has no homology to human genome. In some embodiments, forward primers comprising one or more CCG triplets may comprise a second portion and a third portion at the 5'-end of CCG triplets segment such that the second portion comprises a sequence that has at least 90% homology to the sequence directly upstream (i.e. at the 5'-end) of the CCG repeat tract and the third portion, which is at the 5'-end of the second portion, comprises a sequence that has no homology with the target sequence of SEQ ID NO: 75 (or any of the FMR2 gene).

Exemplary forward primer sequences comprising CCG triplets for detecting CCG repeat tract in the 5'-UTR of FMR2 gene can be any of the CCG triplet containing reverse primers used to detect CCG repeat tract in the 5'-UTR of FMR1 gene as listed in Table 2 above.

PCR Assay Condition:

Exemplary PCR assay mix may comprise 1× PCR buffer; 2 mM MgCl$_2$; 6% DMSO (Sigma); 1.7% Q solution (Qiagen); 0.2 mM each of dGTP, dATP, dCTP, and dTTP; 1 unit of Roche FastStarTaq polymerase; and 0.6 µM each of the forward primer, reverse primer, and M13 reverse linker primer. The dNTP concentration can vary from 50-300 uM.

Optionally, dGTP may be partially or completely replaced with a dGTP analogue such as 7-deaza-2-deoxyGTP to improve the amplification efficiency of the highly GC rich CGG repeat sequence. dGTP analogues are described in U.S. Pat. Nos. 5,658,764 and 4,804,748. 7-deaza-dGTP prevents the Hoogsteen bond formation without interfering Watson-Crick base pairing and is incorporated by Taq polymerase (Seela et al. Biochemistry 1982; 21: 4338-4343). Several reagents may optionally be added to the PCR reaction mixture to improve amplification efficiency of the highly GC rich CGG repeat sequence of FMR1 gene and CCG repeat sequence of FMR2 gene. Exemplary reagents include but not limited to betaine, formamide, glycerol, dimethyl sulfoxide (DMSO). In one embodiment, the betaine concentration may be from 1M to 3M. In some embodiments, the betaine concentration can be 1.5M to 2.5M. In some embodiments, the DMSO concentration can be between 1%-3%. In some other embodiments, the DMSO concentration can be 1.5%. The PCR assay may further include controls such as positive controls and negative controls. Exemplary controls include nucleic acid samples with known status of CGG repeats for FMR1 gene and CCG repeats for FMR2 gene. Positive controls for normal or wild type FMR1 gene (i.e., less than 55 tandem CGG repeats), the premutation (55-200 tandem CGG repeats), and the full mutation (greater than 200 tandem CGG repeats) may be used. Similarly, for FMR2 gene, positive controls for normal or wild type FMR2 gene (i.e., less than 31 tandem CCG repeats), the premutation (60-200 tandem CCG repeats), and the full mutation (greater than 200 tandem CCG repeats) may be used.

Nucleic Acid Detection

Expansion of CGG repeats in the 5'-UTR of the FMR1 gene and CCG repeats in the 5'-UTR of the FMR2 gene can be detected by methods known in the art. Exemplary methods include but are not limited to sequencing, hybridization of specific probes such as Southern blot, detection by size such as by capillary electrophoresis, column chromatography or mass spectrometry. Detectable labels can be used to identify the probe hybridized to a nucleic acid such as genomic nucleic acid. Detectable labels include but are not limited to fluorophores, isotopes (e.g., $^{32}P$, $^{33}P$, $^{35}S$, $^{3}H$, $^{14}C$, $^{125}I$, $^{131}I$), electron-dense reagents (e.g., gold, silver), nanoparticles, enzymes commonly used in an ELISA (e.g., horseradish peroxidase, beta-galactosidase, luciferase, alkaline phosphatase), chemiluminiscent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

Probes

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in preferred embodiments, amplified fractions are separated on an agarose gel and stained with ethidium bromide by methods known in the art to detect amplified fragments or may be detected by Southern blot.

Hybridization

The degree of complementarity between nucleic acid strands has significant effects on the efficiency and strength of hybridization between nucleic acid strands. This is of particular importance in detection methods that depend upon binding between nucleic acids. In one embodiment, the complementarity between the probe and the genomic nucleic acid may be "partial" in which only some of the nucleic acids' bases are matched according to the base pairing rules. In another embodiment, complementarity between the probe and the genomic nucleic acid may be "complete," "total," or "full".

The methods of the present invention can incorporate all known methods and means and variations thereof for carrying out DNA hybridization, see, e.g., Sambrook, et al., 1989, Molecular Cloning: A Laboratory Manual, Second Edition, Cold Spring Harbor Press, Plainview, N.Y.

The nucleic acid such as genomic nucleic acids and probes chosen for the nucleic acids are contacted under hybridization conditions. Hybridization conditions for nucleic acids in the methods of the present invention are well known in the art. For example, hybridization conditions may be high, moderate or low stringency conditions. Ideally, nucleic acids will hybridize only to complementary nucleic acids and will not hybridize to other non-complementary nucleic acids in the sample. The hybridization conditions can be varied to alter the degree of stringency in the hybridization and reduce background signals as is known in the art. For example, if the hybridization conditions are high stringency conditions, a nucleic acid will detectably bind to nucleic acid target sequences with a very high degree of complementarity. Low stringency hybridization conditions will allow for hybridization of sequences with some degree of sequence divergence. The hybridization conditions will vary depending on the biological sample, and the type and sequence of nucleic acids. One skilled in the art will know how to optimize the hybridization conditions to practice the methods of the present invention.

Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5× Denhardt's solution, 5× SSC (saline sodium citrate) 0.2% SDS (sodium dodecyl sulphate) at 42° C., followed by washing in 0.1× SSC, and 0.1% SDS at 65° C. Moderate stringency refers to conditions equivalent to hybridization in 50% formamide, 5× Denhardt's solution, 5× SSC, 0.2% SDS at 42° C., followed by washing in 0.2× SSC, 0.2% SDS, at 65° C. Low stringency refers to conditions equivalent to hybridization in 10% formamide, 5× Denhardt's solution, 6× SSC, 0.2% SDS, followed by washing in 1× SSC, 0.2% SDS, at 50° C.

Detectable Label

The term "detectable label" as used herein refers to a molecule or a compound or a group of molecules or a group of compounds associated with a probe or primer and is used to identify the probe hybridized to a genomic nucleic acid or reference nucleic acid or the amplicon into which the primer incorporated.

Detectable labels include but are not limited to fluorophores, isotopes (e.g. 32P, 33P,35S, 3H, 14C, 125I, 131I), electron-dense reagents (e.g., gold, silver), nanoparticles, enzymes commonly used in an ELISA (e.g., horseradish peroxidase, beta-galactosidase, luciferase, alkaline phosphatase), chemiluminiscent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

In some embodiments, the detectable label is a fluorophore. Suitable fluorescent moieties include but are not limited to the following fluorophores working individually or in combination: 4-acetamido-4'-isothiocyanatostilbene-2, 2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120),7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl) aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC).

Other fluorescent nucleotide analogs can be used, see, e.g., Jameson et al. Meth. Enzymol. 1997; 278: 363-390; Zhu et al. Nucleic Acids Res. 1994; 22: 3418-3422. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield et al. Mol. Cell. Probes. 1995; 9:145-156.

Detectable labels can be incorporated into nucleic acid probes by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3™ or Cy5,™ and then incorporated into nucleic acid probes during nucleic acid synthesis or amplification. Nucleic acid probes can thereby be labeled when synthesized using Cy3™- or Cy5™-dCTP conjugates mixed with unlabeled dCTP.

Detection of Nucleic Acid by Size:

Methods for detecting the presence or amount of polynucleotides are well known in the art and any of them can be used in the methods described herein so long as they are capable of separating individual polynucleotides by the difference in size of the amplicons. The separation technique used should permit resolution of nucleic acid as long as they differ from one another by at least one nucleotide. The separation can be performed under denaturing or under non-denaturing or native conditions—i.e., separation can be performed on single- or double-stranded nucleic acids. It is preferred that the separation and detection permits detection of length differences as small as one nucleotide. It is further preferred that the separation and detection can be done in a high-throughput format that permits real time or contemporaneous determination of amplicon abundance in a plurality of reaction aliquots taken during the cycling reaction. Useful methods for the separation and analysis of the amplified products include, but are not limited to, electrophoresis (e.g., agarose gel electrophoresis, capillary electrophoresis (CE)), chromatography (HPLC), and mass spectrometry.

In one embodiment, CE is a preferred separation means because it provides exceptional separation of the polynucleotides in the range of at least 10-3,000 base pairs with a resolution of a single base pair. CE can be performed by methods well known in the art, for example, as disclosed in U.S. Pat. Nos. 6,217,731; 6,001,230; and 5,963,456, which are incorporated herein by reference. High-throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE 5000 series and CEQ series from Beckman Instruments Inc (Fullerton, Calif.); and ABI PRISM 3730 genetic analyzer (Applied Biosystems, Foster City, Calif.). Near the end of the CE column, in these devices the amplified DNA fragments pass a fluorescent detector which measures signals of fluorescent labels. These apparatuses provide automated high throughput for the detection of fluorescence-labeled PCR products.

The employment of CE in the methods described herein permits higher productivity compared to conventional slab gel electrophoresis. By using a capillary gel, the separation speed is increased about 10 fold over conventional slab-gel systems.

With CE, one can also analyze multiple samples at the same time, which is essential for high-throughput. This is achieved, for example, by employing multi-capillary systems. In some instances, the detection of fluorescence from DNA bases may be complicated by the scattering of light from the porous matrix and capillary walls. However, a confocal fluorescence scanner can be used to avoid problems due to light scattering (Quesada et al. Biotechniques. 1991; 10: 616-25.

In some embodiments, nucleic acid may be analyzed and detected by size using agarose gel electrophoresis. Methods of performing agarose gel electrophoresis are well known in the art. See Sambrook et al., Molecular Cloning: A Laboratory Manual (2nd Ed.) (1989), Cold Spring Harbor Press, N.Y.

In some embodiments, nucleic acid may be analyzed by HPLC. HPLC columns for separation of nucleic acid are available commercially such as HYDROCELL NS 1500, DEAE NP 10, QA NP 10 columns from Biochrom Labs Inc. (IN, USA) allow separation of nucleic acids. Ion pair reverse phase HPLC can also be used for DNA fragment analysis.

DNA Sequencing:

In some embodiments, detection of nucleic acid is by DNA sequencing. Sequencing may be carried out by the dideoxy chain termination method of Sanger et al.(Proc. Natl. Acad. Sci. USA 1977; 74: 5463-5467) with modifications by Zimmermann et al. Nucleic Acids Res. 1990; 18: 1067. Sequencing by dideoxy chain termination method can be performed using Thermo Sequenase (Amersham Pharmacia, Piscataway, N.J.), Sequenase reagents from US Biochemicals or Sequatherm sequencing kit (Epicenter Technologies, Madison, Wis.). Sequencing may also be carried out by the "RR dRhodamine Terminator Cycle Sequencing Kit" from PE Applied Biosystems (product no. 403044, Weiterstadt, Germany), Taq DyeDeoxy™ Terminator Cycle Sequencing kit and method (Perkin-Elmer/Applied Biosystems) in two directions using an Applied Biosystems Model 373A DNA or in the presence of dye terminators CEQ™ Dye Terminator Cycle Sequencing Kit, (Beckman 608000).

Alternatively, sequencing can be performed by a method known as Pyrosequencing (Pyrosequencing, Westborough, Mass.). Detailed protocols for Pyrosequencing can be found in: Alderborn et al. Genome Res. 2000; 10: 1249-1265.

Correlation of the Number of CGG repeats in 5'-UTR of FMR1 Gene and CCG Repeats in 5'-UTR of FMR2 Gene to Normal or Carrier/Affected Status In some embodiments, individuals that are afflicted with a disease associated with an expansion of the CGG repeat region of the FMR1 gene can be distinguished from those that are normal. In some embodiments, a nucleic acid sample from the individual comprising the CGG repeat region is amplified using primers having one or more CCG triplets generate broad range of amplicons having varying lengths. The amplicons are separated into fractions according to size to have a distinctive pattern of tapering or "stutter". Male and female individuals can be differentiated into normal (5-44 CGG repeats), intermediate, premutation (55-200 CGG repeats), and full mutation alleles (>200 CGG repeats) based on the size separation of the amplicons.

In some embodiments, individuals that are afflicted with a disease associated with an expansion of the CCG repeat region of the FMR2 gene can be distinguished from those that are normal. In some embodiments, a nucleic acid sample from the individual comprising the CCG repeat region is amplified using primers having one or more CGG triplets generate broad range of amplicons having varying lengths. The amplicons are separated into fractions according to size to have a distinctive pattern of tapering or "stutter". Male and female individuals can be differentiated into normal (6-30 CCG repeats), intermediate (31-60), premutation (61-200 CCG repeats), and full mutation alleles (>200 CCG repeats) based on the size separation of the amplicons.

Approaches to Patient Screening for FMR1 CGG Repeat Mutation Status and FMR2 CCG Repeat Mutation Status In one embodiment, individuals may be tested for FMR1 CGG mutation status using the triplet primed amplification method of the invention in combination with other assays. In another embodiment, individuals may be tested for FMR2 CCG mutation status using the triplet primed amplification method of the invention in combination with other assays. One such assay also known as Capillary Southern Assay (CSA) was described by Strom et al. (Genet Med. 2007; 9(4):199-207) (see also US 20080124709 by Strom et al.). In the method described by Strom et al., gender of the nucleic acid sample is first confirmed by using an initial multiplex PCR that amplifies the FMR1 comprising the CGG triplet repeats, a region of the amelogenin gene that yields different fragment sizes from the X and Y chromosomes for gender determination, and a polymorphic region of the androgen insensitivity gene used as an internal control. The amplicons from the initial PCR reaction are then analyzed by an automated capillary DNA sequencer. After the initial PCR reaction and gender determination, the samples are further analyzed by the CSA method. The method involves restriction digestion of nucleic acid comprising the FMR1 gene and the 5'-UTR into multiple fragments and separating the fragments by capillary electrophoresis. The presence or absence of FMR1 gene is detected in the size separated fragments by gene specific PCR. The size of the fractions is indicative of CGG repeat expansion.

Figure 17:
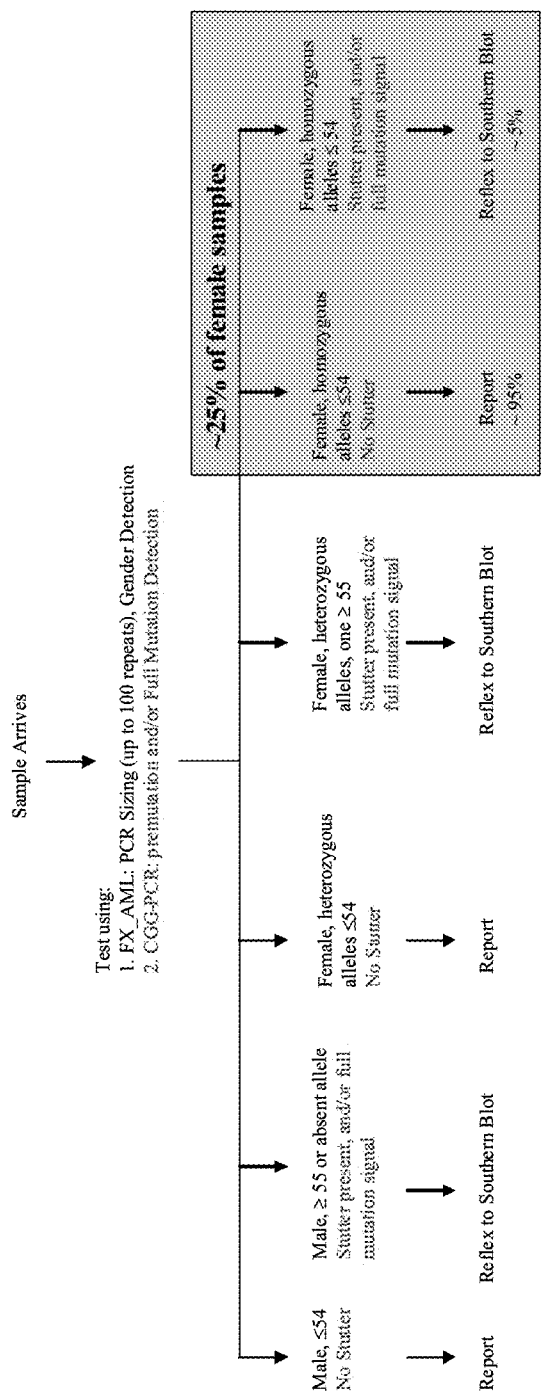
FIG. 17 shows an exemplary testing algorithm for samples submitted for Fragile X testing. Samples received will be tested using two different PCR based assays. Reaction 1 can be used for sizing normal, intermediate and small premutations, as well as gender determination using Capillary Southern Assay (Strom et al. Genet Med. 2007; 9(4): 199-207). Reaction 2 (triplet primed amplification of the invention) will detect the presence of expanded alleles and full mutations. Samples showing evidence of stutter or full mutation amplification will be further analyzed by Southern blot analysis for methylation status and sizing. As shown in the figure, the use of triplet primed amplification will significantly reduce the number of Southern blot analyses to be performed because the method clearly distinguishes normal homozygous females, which represent ~95% of all female samples from full mutation carriers.

The triplet primed amplification method of the invention is useful for identifying larger premutations and full mutations. The CSA method enables accurate sizing of repeat number in the normal, intermediate, and small premutation zone as well as gender identification/confirmation. The combination of both the CSA method and triplet primed amplification for each individual would yield results for both males and females, and this would serve the purpose for carrier and/or newborn screening. The triplet primed amplification method should significantly reduce the number of Southern blot analyses to be performed as the method clearly distinguishes normal homozygous females, which represent 95% of all female samples from full mutation carriers. A schematics of the two different assays run simultaneously for determining CGG repeat expansion is shown in FIG. 17.

The CSA method of Strom et al. can also be applied to the detection and confirmation of CCG repeat mutation status of FMR2 gene. In some embodiments, the FMR1 CGG mutation status and the FMR2 CCG mutation status can be determined simultaneously in a single assay. In another embodiment, the FMR1 CGG mutation status and the FMR2 CCG mutation status can be determined using the same sample using two separate assays.

Estimation of Premutation and Full Mutation Frequency in FMR1 Gene

In some embodiments, estimation of the number of CGG triplets in the CGG repeat tract of FMR 1 gene will allow an artisan to determine the premuation carrier frequency and full mutations in a population. The estimation of the number of CGG triplets in the CGG repeat tract of FMR 1 gene will also allow to calculate the incidence of FXS, FXTAS and FXPOI in a population. Premuation carrier frequency in females can be estimated from the experimental results and can be expressed as the fraction of female population tested to have premutation (≥55 CGG repeats) in FMR1 gene. The premuation carrier frequency in males as well as the full mutation frequency in both males and females can be calculated from the premuation carrier frequency in females. Full mutation frequency in an individual (male or female) can be calculated based on the premutation carrier frequency of a female using the following equation:

Full mutation frequency=premutation carrier frequency in females×S×0.5 where S is the rate of expansion of a premutation into a full mutation and was calculated to be 0.107 (i.e. ~10.7% of premutations expand to full mutations), while 0.5 is the probability of inheriting either allele.

Premutation carrier frequency in males can be calculated using the equation:

Premut. carrier frequency in males=premut. carrier frequency in females×(1-S)×0.5

Estimation of the Incidence of FXTAS and FXPOI in a Populations

In some embodiments, the incidence of FXTAS and FXPOI in a populations can be calculated by utilizing the estimated frequency of premutations in males or females, the reported penetrance of alleles in male and female carriers, and frequency of larger premutation alleles. The incidence of FXTAS can be calculated using the following equation:

incidence of FXTAS premutation carrier frequency in males×$P_{FETAS}$×frequency of alleles ≥70 CCG repeats where $P_{FXTAS}$ is penetrance in patients of larger premutation alleles (≥70 CGG repeats) in FXTAS estimated to be ⅓ (0.33).

The incidence of FXPOI incidence can be calculated using the following equation:

incidence of FXPOI premutation carrier frequency in females⊖$P_{FXPOI}$×frequency of alleles ≥70 CCG repeats where PFXPOI is the penetrance of large premutation alleles (≥70 CGG repeats) in FXPOI estimated to be ~20%-28%.

EXAMPLE 1

Samples

Residual archived DNA from patient samples already processed for fragile X analysis using existing assays were de-identified and used in the development of the PCR method. DNA was extracted using the Qiagen M96 robot and reagents (Qiagen, Carlsbad, Calif.), Qiagen Gentra robot and reagents, and Qiagen 9604 reagents. The samples included a homozygous normal female (28/28 repeats), a heterozygous normal female (18/21), a premutation female (31/64), full mutation females (19/450 and 29/530), a normal male (28), a premutation male (74), and mosaic full mutation male (105/350). Once conditions for the PCR were established, a larger set of 47 anonymized, previously genotyped samples (Table 4), weighted toward full mutation carriers (male or female), were used to test the robustness of the assay.

TABLE 4

Panel of Previously FMR1 Genotyped Samples Used to Test Performance of the Triplet-Primed PCR/Capillary Electrophoresis-Based Assay.

| Sample # | Previous Genotype Call | Southern Blot Analysis | Classification by Triplet-Primed PCR/CE |
|---|---|---|---|
| 1 | 23/800 | | FF |
| 2 | 29/590 | | FF |
| 3 | 687 | | FM |
| 4 | 19/88 | | PF |
| 5 | 104 | | PM |
| 6 | 82 | | PM |
| 7 | 28/400 | | FF |
| 8 | 506-1006 | | FM |
| 9 | 29/286 | | FF |
| 10 | 28/98 | | PF |
| 11 | 660 | | FM |
| 12 | 400 | | FM |
| 13 | 29/29 | | NF |
| 14 | 696 | | FM |
| 15 | 67/500 | | FM |
| 16 | 28/29 | | NF |
| 17 | 78/2000 | 78 (60%, unmethylated)/ 2000 (40%, methylated) | FM |
| 18 | 45 | | GM |
| 19 | QC Blank | | No Amplification |
| 20 | 23/400-1250 | | FF |
| 21 | 650 | | FM |
| 22 | 850 | | FM |
| 23 | 45/600 | | FF |
| 24 | 30/550 | | FF |
| 25 | 30/49 | | GF |
| 26 | 713 | | FM |
| 27 | 500 | | FM |
| 28 | 400 | | FM |
| 29 | 30/520 | | FF |
| 30 | 19/19 | | HF |
| 31 | 500 | | FM |
| 32 | 30/30 | | HF |
| 33 | 32/73 | | PF |
| 34 | 31/480 | | FF |
| 35 | 170-240 | | FM |
| 36 | 400 | | FM |
| 37 | 600 | | FM |
| 38 | 200-500 | 200 (10%, unmethlyated)/ 200-500 (90%, methylated) | FM |
| 39 | 420 | | FM |
| 40 | 30/74 | | PF |
| 41 | 853 | | FM |
| 42 | 30/313 | | FF |
| 43 | 606 | | FM |
| 44 | 433 | | FM |
| 45 | 140/(200-400) | 140 (5-10%, unmethylated)/ 200-400 (90-95%, methylated) | FF |
| 46 | 300-500 | | FM |
| 47 | 590-1143 | | FM |
| 48 | 666 | | FM |

NF: normal female;
GF: intermediate female;
PF: premutation female;
FF: affected female;
NM: normal male;
GM: intermediate male;
PM: premutation male;
FM: affected male.

To evaluate assay sensitivity, three DNA sets were made using archived, previously genotyped samples, each set harboring two DNA samples mixed at different ratios; set # A contained DNA samples from two males, one from a normal male with 28 CGG repeats, and one from affected male with 850 CGG repeats; set B contained two males, a normal male (28 CGG) and affected male (853), and set C contained two female samples, a normal (28/28) and an affected female (19/450).

To determine whether assay methods could detect fragile X CGG mutation status on blood spots, residual blood from previously genotyped patients were spotted on Guthrie cards. Blood spots were punched from each card using BSD1000 GenePunch Instrument to generate two punches (3.2 mm each) per patient and DNA was extracted using Qiagen BioSprint reagents. DNA from blood spots was analyzed by the triplet-primed PCR/capillary electrophoresis as described in Example 2. A total of 37 samples containing the different FMR1 CGG expansions in males and females were tested (Table 5). The series contained fourteen samples with intermediate repeats, nine samples with pre-mutations, and four samples with full mutations (as determined by Southern blot analysis), one female (20/500 repeats) and three males (300-700; 1250; 1250 repeats).

TABLE 5

Samples used for blood spots.

| Sample # | Genotype* | Previous Result | Classification by Triplet-Primed PCR/CE |
|---|---|---|---|
| 1 | 29/46 | IF | No Expansion |
| 2 | 23/55 | PF | PF |
| 3 | 28/66 | PF | PF |
| 4 | 31/53 | IF | No Expansion |
| 5 | 20/500 | FF | FF |
| 6 | 60 | PM | PM |
| 7 | 46 | IM | No Expansion |
| 8 | 53 | IM | No Expansion |
| 9 | 28/28 | HF | No Expansion |
| 10** | — | — | No Amplification |
| 11 | 31/45 | IF | No Expansion |
| 12 | 30/49 | IF | No Expansion |
| 13 | 29/29 | HF | No Expansion |
| 14 | 19/54 | IF | No Expansion |
| 15 | 30 | NM | No Expansion |

TABLE 5-continued

Samples used for blood spots.

| Sample # | Genotype* | Previous Result | Classification by Triplet-Primed PCR/CE |
|---|---|---|---|
| 16 | 34/50 | IF | No Expansion |
| 17 | 300-700 | FM | FM |
| 18 | 44/57 | PF | PF |
| 19 | 32/45 | IF | No Expansion |
| 20** | — | — | No Amplification |
| 21 | 50 | IM | No Expansion |
| 22 | 30/51 | IF | No Expansion |
| 23 | 29/70 | PF | PF |
| 24 | 1250 | FM | FM |
| 25 | 46 | IM | No Expansion |
| 26 | 30/30 | HF | No Expansion |
| 27 | 29/78 | PF | PF |
| 28 | 29/29 | HF | No Expansion |
| 29 | 30/64 | PF | PF |
| 30** | — | — | No Amplification |
| 31 | 1250 | FM | FM |
| 32 | 35/59 | PF | PF |
| 33 | 30/30 | HF | No Expansion |
| 34 | 30/66 | PF | PF |
| 35 | 30/30 | HF | No Expansion |
| 36 | 29/29 | HF | No Expansion |
| 37 | 30/30 | HF | No Expansion |
| 38 | 30/30 | HF | No Expansion |
| 39 | 32/47 | IF | No Expansion |
| 40** | — | — | No Amplification |
| 41 | 30/49 | IF | No Expansion |

Genotype is listed as the number of triplet repeats on each FMR1 allele.
Abbreviations are as in Table 4. No Expansion includes normal and intermediate alleles.
**Samples 10, 20, 30 and 40 contained blank cards for cross contamination detection. These samples showed no amplification (NA).

To determine the premutation frequency in US population, residual anonymized DNA samples submitted for Cystic Fibrosis (CF) carrier screening and samples submitted for screening for diseases more prevalent in Ashkenazi Jews were used. A total of 13770 samples were analyzed in this study, >99% of the sample were from females. Table 6 shows the breakdown of samples by self-identified ethnicity. Greater than 43% did not provide ethnicity information, while 4.9% of samples listed as other or mixed ethnicities. Caucasian accounted for 20.8% of the total samples, Hispanics accounted for 12.5% of samples, samples from each of African Americans and Asians accounted for 1.8% of the total samples.

TABLE 6

Composition of the population studied.

| Ethnicity | Samples Screened | % Patients |
|---|---|---|
| Caucasian | 2866 | 20.8 |
| African American/Black | 247 | 1.8 |
| Hispanic | 1723 | 12.5 |
| Ashkenazi Jewish | 2011 | 14.6 |
| Asian | 254 | 1.8 |
| Other | 674 | 4.9 |
| Not given | 5995 | 43.5 |
| Total | 13770 | 100.0 |

EXAMPLE 2

Assay Development and Assay Conditions

The CGG repeats in the FMR1 gene were amplified by PCR. The PCR reaction included a fluorescently labeled forward primer and reverse primers comprising at least two CCG triplets such that the reverse primers can anneal to CGG repeat sequence. In one example, the reverse primer also comprised the junction sequence of the 3'-end of the CGG repeat tract and flanking sequence and a portion of the sequence downstream of CGG repeat. The reverse primers having at least two CCG triplets and without such junction sequence will hybridize randomly inside the CGG repeat sequence and initiate DNA synthesis. This will result in a range of amplicons of different sizes (stutter). The reverse primers further comprised a M13 linker sequence at its 5'-end such that a M13 primer can anneal to this linker sequence and further amplify the amplicons thus generated.

The PCR mix for amplification of all normal, premutation, and full mutations of the CGG repeats were optimized by formulating various combinations of mixes using Roche Expand polymerase PCR mix buffer 2 or 3, Roche High-GC PCR mix, and incorporating various additives at different concentrations including Roche Q-solution, DMSO, HiDi Formamide, Tween-20, or combinations thereof. Initially, Roche Expand kit without the addition of deaza-dGTP was tested. However, Roche FastStarTaq kit reagents (Roche Applied Science, Indianapolis, Ind.) provided better performance in terms of signal intensity under identical cycling conditions.

The PCR mix contained 1× PCR buffer; 2 mM $MgCl_2$; 6% DMSO (Sigma); 1.7% Q solution (Qiagen); 0.2 mM each of 7-deaza-2-deoxyGTP, dATP, dCTP, and dTTP; 1 unit of Roche FastStarTaq polymerase; and 0.6 µM each of the forward primer (FMR1F), reverse primer, and M13 reverse linker primer. Several variations of the reverse primers were tested together with the FMR1F forward primer. The sequences of the primers are listed below in Table 7.

TABLE 7

Primers used in the PCR reaction

| Primer | Sequence | SEQ ID NO: |
|---|---|---|
| FMR1F Forward | 6-FAM_TGTAAAACGACGGCCAGTGCTCAGCTCCGT TTCGGTTTCACTTCCGGT | 2 |
| FMR1R Reverse | CAGGAAACAGCTATGACCctcgaggcccaGCCGCCG CCGCC | 3 |
| FMR1CCGR Reverse | CAGGAAACAGCTATGACCCCGCCGCCGCC | 4 |
| CGG1 Reverse | CAGGAAACAGCTATGACCCGCCGCCGCC | 5 |
| CGG2 Reverse | CAGGAAACAGCTATGACCCCGCCGDCGCCGCCGCC | 6 |
| CGG3 Reverse | CAGGAAACAGCTATGACCCCGCCGCCGCCGCCGCCG CCGCCGCCGCCG | 7 |
| CGG4 Reverse | CAGGAAACAGCTATGACCCCGCCGCCGCCGCCGCCG CCG | 8 |
| CGG3-1 Reverse | CAGGAAACAGCTATGACCCCGCCGCCGCCGCCGCCG CCGCCGCC | 9 |
| CGG4-1 Reverse | CAGGAAACAGCTATGACCCCGCCGCCGCCGCCGCCG CC | 10 |

TABLE 7-continued

Primers used in the PCR reaction

| Primer | Sequence | SEQ ID NO: |
|---|---|---|
| FMR1R_7 Reverse | CAGGAAACAGCTATGACCCTCGAGGCCCAGCCGCCG CCGCCGCC | 71 |
| FMR1R_8 Reverse | CAGGAAACAGCTATGACCCTCGAGGCCCAGCCGCCG CCGCCGCCGCC | 72 |
| FMR1R_9 Reverse | CAGGAAACAGCTATGACCCTCGAGGCCCAGCCGCCG CC | 73 |
| FMR1R_10 Reverse | CAGGAAACAGCTATGACCCTCGAGGCCCAGCCGCCG | 74 |
| M13 reverse linker primer | CAGGAAACAGCTATGACC | 11 |

D: A, G or T

Three microliters of genomic DNA (10-150 ng total) was added for a final PCR reaction volume of 15 µl. The cycling program, performed on an ABI 9700 thermal cycler, was started by incubating the mix at 98° C. for 10 minutes to activate the polymerase, followed by 10 cycles of denaturation at 97° C. for 35 sec, annealing at 64° C. for 2 minutes, and extension at 68° C. for 8 minutes, followed by 25 cycles of denaturation at 97° C. for 35 sec, annealing at 64° C. for 2 minutes, and extension at 68° C. for 8 min 20 sec (with 20 sec extension each additional cycle). For all 35 cycles, the ramp rate was adjusted to 64% for the denaturation and extension steps (ramping up at 0.5° C.), and to 25% for the annealing step (ramping down at 0.5° C.). Two microliters of the PCR product (some times diluted 1:5 in H$_2$O) were mixed with HiDi Formamide and Map marker-1000 size standard (Bioventures Inc., Murfreesboro, Tenn.) and samples were injected on an ABI 3730 DNA Analyzer equipped with a 36-cm capillary loaded with Pop-7 polymer (Applied Biosystems) at 3 volts for 7 seconds. Data were analyzed using GeneMapper software (Applied Biosystems).

The forward primer FMR1F is fluorescently labeled with FAM and anneals to 5'-UTR of FMR1 gene upstream of the CGG repeats. The reverse primers were designed to comprise at least two consecutive CCG triplets such that the primers anneal to the CGG repeat sequences of the FMR1 gene. Reverse primer FMR1R (SEQ ID NO: 3) comprise 4 CCG triplet sequences and the junction sequence directly next to the 3'-end of the CGG repeat tract, the later indicated in bold lowercase. The reverse primers also comprise M13 linker sequence at its 5'-end (underlined) which provides hybridization sites for M13 reverse linker primer in further round of amplification. Reverse primers FMR1CCGR, CGG1, CGG2, CGG3, CGG4, CGG3-1, CGG4-1, FMR1_7, FMR1_8, FMR1_9, FMR1_10 can hybridize randomly to the CGG repeat sequence of FMR1 gene and initiate DNA synthesis to generate a range of amplicons of different sizes (stutter). A schematics of the PCR assay indicating the forward and reverse primers binding sites relative to the CGG repeat sequences is shown in FIG. 2.

The inclusion of the M13 linker in the reverse primers also helped to boost the signal by about 30%. The incorporation of ramping in the cycling program helped further boost signal amplification by at least three fold.

EXAMPLE 3

Figure 3:
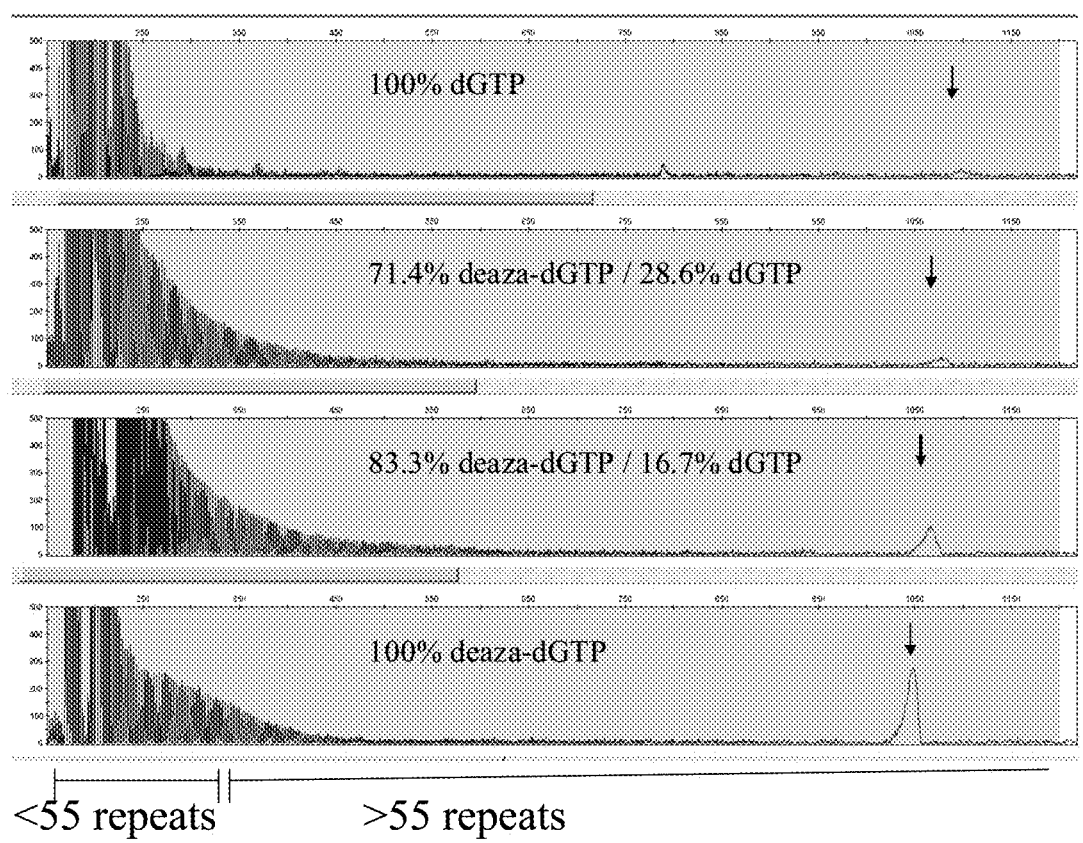
FIG. 3 is an electropherogram showing the effect of 7-deaza-2-deoxyGTP on full mutation detection in FMR1 gene. The primers used to amplify the CGG repeat region were FMR1F, FMR1R, FMR1CCGR, and M13R. PCR master mixes were formulated with shown concentrations of 7-deaza-dGTP and dGTP. An affected female DNA sample (19/450) was used in the PCR reactions. The positions of the normal and intermediate alleles (<55 CGG repeats) and premutation and full mutation alleles 55 CGG repeats) are indicated below the electropherograms. The arrow shows the signal for the full mutation. Replacing dGTP with 7-deaza-dGTP influences the migration and detectability of the amplified full mutation fragment.
Figure 4:
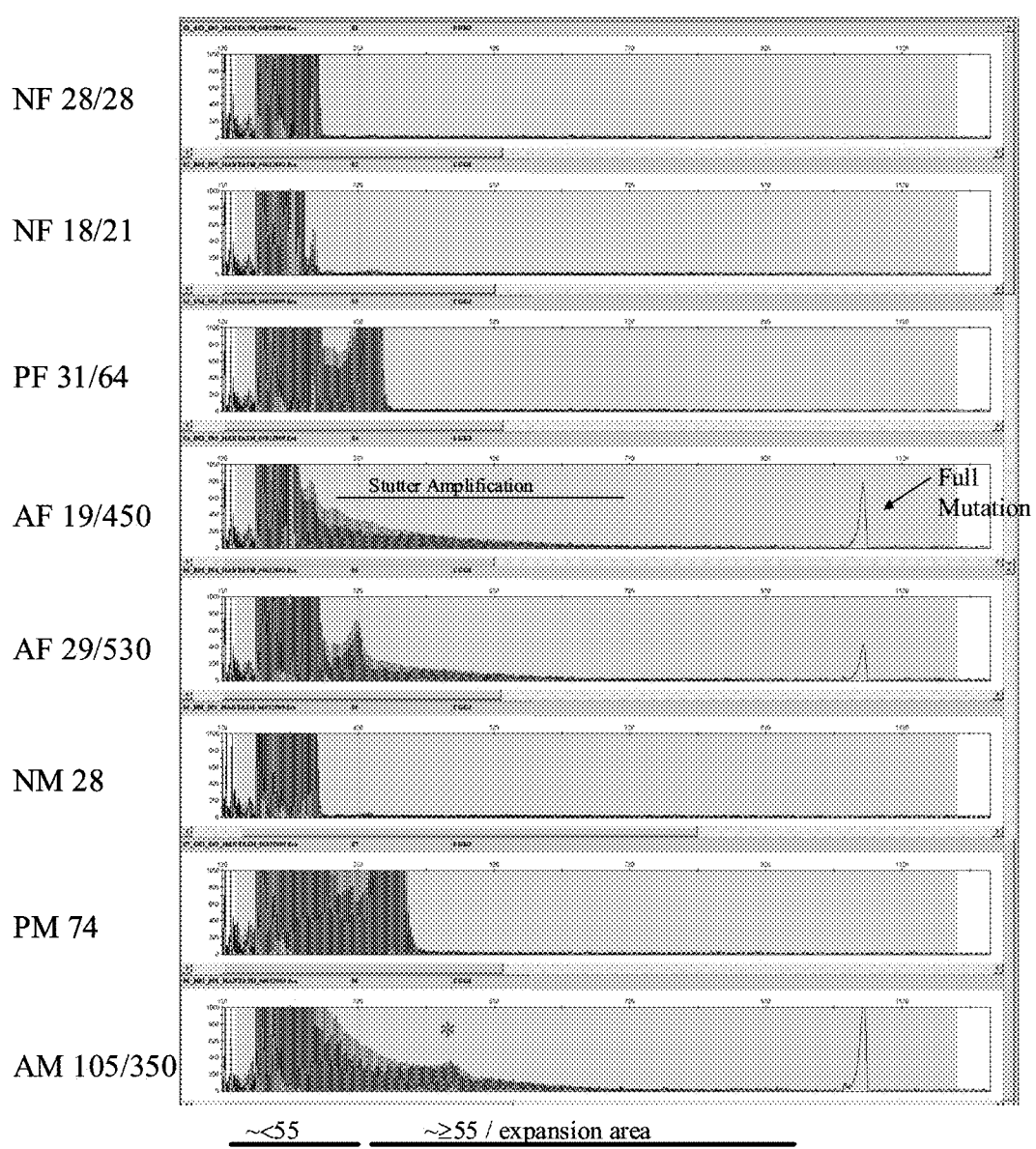
FIG. 4 is an electropherogram showing exemplary amplification results of th CGG repeat tract of 5'-UTR of FMR1 gene obtained from normal, carrier and affected female and male fragile X patients using primers FMR1F and FMR1R and M13R in presence of 7-deaza-dGTP. The status of alleles as to number of repeats is shown for each patient. The assay distinguishes between normal females or males, including normal homozygous females, from full mutation carrier females or males. The last panel shows a sample from a mosaic male with 105/350 alleles. The 105 repeat allele is marked by an asterisk.

Effect of the Addition of 7-deaza-2-deoxyGTP on PCR Amplification of CGG Repeats The effect of substituting dGTP with 7-deaza-2-deoxyGTP in the PCR reaction was tested to improve the amplification efficiency of the highly GC rich CGG repeat sequence. Deaza-dGTP prevents the Hoogsteen bond formation without interfering Watson-Crick base pairing and is incorporated by Taq polymerase (Seela et al. Biochemistry 1982; 21: 4338-4343). The effect of increasing concentration of 7-deaza-2-deoxyGTP was tested in the PCR reaction mixture using genomic DNA isolated from a heterozygote female carrier (29/530). Increasing the concentration of 7-deaza-2-deoxyGTP not only boosted the signal from stutter amplification, but also led to the appearance of a peak that migrated very late on the ABI 3730 capillary and was evident only when a full mutation was present (FIG. 3 and FIG. 4). Even though amplicons containing 7-deaza-2-deoxyGTP do not stain with ethidium bromide, the presence of a premutation and a full mutation could be detected in a single PCR reaction by stutter and full mutation signals, thus distinguishing homozygous normal females from heterozygous full mutation-carrier females.

Using a panel of eight anonymized, previously genotyped samples, various possibilities of CGG triplet repeat status were tested. The assay could distinguish between normal and intermediate alleles (<55 CGG repeats) from premutation and full mutation alleles (with ≥55 CGG repeats) as shown in the electropherogram (FIG. 4). Normal females and normal males display alleles only in the gray (or left hand shaded) area of the electropherogram, while premutation males and females, display alleles in the pink area (or right hand shaded), with stutter amplification prior to the actual premutation peak. Full mutation carrying males and females display, in addition to normal allele in females, a tapering stutter amplification followed by a signal at the end of electropherogram that is present only whenever a full mutation is present. Most significantly, normal homozygote females can be distinguished from full mutation carrier females using this method (FIG. 4).

EXAMPLE 4

Amplification of CGG Repeats by Different Reverse Primers

The efficiency of amplification of CGG repeats by the reverse primers were tested using a PCR reaction mixture comprising 1× PCR buffer; 2 mM MgCl$_2$; 6% DMSO (Sigma); 1.7× Q solution (Qiagen); 0.2 mM each of 7-deaza-2-deoxyGTP, dATP, dCTP, and dTTP; 1 unit of Roche FastStarTaq polymerase; and 0.6 µM each of the forward primer (FMR1F), M13 reverse linker primer, and one of the reverse primers: FMR1R, CGG1, CGG2, CGG3, CGG4, CGG3-1 and CGG4-1 using genomic DNA isolated from 4 samples: full mutation female (FF 23/800) full mutation male (FM 687), premutation female (PF 19/88) and homozygous female (HF 29/29).

All reverse primers generated a stutter pattern of amplicons for the three samples: full mutation female, full mutation male and premutation female (FIGS. 8-14). Reverse primers FMR1R, CGG1, CGG2, CGG4-1 generated full mutation peaks which appeared around the 1050 bases for samples FF 23/800 and FM 687 as indicated in the electropherogram of FIGS. 8, 9, 10 and 14.

EXAMPLE 5

Effect of the Addition of Various Concentrations of GTP, 2-deoxyGTP and 7-deaza-2-deoxyGTP on PCR Amplification of CGG Repeats by Different Reverse Primers at Different Annealing Temperatures The effect of increasing concentration of GTP, 2-deoxyGTP, and 7-deaza-2-deoxy GTP on the amplification efficiency of the highly GC rich CGG repeat sequence were tested. Varying amounts of GTP, 2-deoxyGTP, and 7-deaza-2-deoxyGTP were added to the PCR reaction mixture comprising 1× PCR buffer; 2 mM $MgCl_2$; 6% DMSO (Sigma); 1.7× Q solution (Qiagen); 0.2 mM each of dATP, dCTP, and dTTP; 1 unit of Roche FastStarTaq polymerase; and 0.6 µM each of the forward primer (FMR1F), M13 reverse linker primer, and one of the reverse primers: FMR1R, FMR1R_7, FastStarTaq polymerase; and 0.6 µM each of the forward primer (FMR1F), M13 reverse linker primer, and reverse primer FMR1R at an annealing temperature of 64° C. Results from each of the amplification conditions were compared to the reference condition to determine the efficiency of detecting stutter pattern and full mutation.

The addition of GTP to the reaction mixture up to a final concentration of 200 µM did not have a significant effect on the amplification efficiency of the highly GC rich CGG repeat sequence. The amplification efficiencies were comparable or better in reaction conditions having 7-deaza-2-deoxyGTP concentration of .85 mM to 1 mM. The amplification efficiencies with reverse primer FMR1R_9 under various reaction conditions were comparable or better than the results obtained from the reference condition, while the amplification efficiencies with reverse primer FMR1R_8 under various reaction conditions tested were worse than the results obtained from the reference condition. A comparison of the results of the different reaction conditions to the reference condition is presented in Table 8 below.

TABLE 8

Comparison of amplification efficiency for detection of stutter pattern and full mutation in presence of GTP, 7-deaza-2-deoxyGTP, using various reverse primers

| Condition | Primer Forward | Primer Reverse | Length of CCG | Deaza-dGTP uM | dGTP uM | GTP uM | % dGTP/GTP | Annealing Temp (° C.) | Result | Stutter | Full Mutation |
|---|---|---|---|---|---|---|---|---|---|---|---|
| Ref | FMR1F | FMR1R | 3⅔ | 200 | 0 | | 0.0 | 64 | Reference Condition | Present | Present |
| 1 | FMR1F | FMR1R_9 | 2⅔ | 650 | 12 | | 1.8 | 60 | Comparable or better | Present | Present/Strong |
| 2 | FMR1F | FMR1R_9 | 2⅔ | 650 | 12 | | 1.8 | 64 | Better | Present | Present/Strong |
| 3 | FMR1F | FMR1R_9 | 2⅔ | 1000 | 12 | | 1.2 | 60 | Comparable or better | Present | Present/Strong |
| 4 | FMR1F | FMR1R_9 | 2⅔ | 1000 | 12 | | 1.2 | 64 | Better | Present | Present/Strong |
| 5 | FMR1F | FMR1R_9 | 2⅔ | 850 | 6 | | 0.7 | 60 | Comparable or better | Present | Present/Strong |
| 6 | FMR1F | FMR1R_9 | 2⅔ | 850 | 6 | | 0.7 | 64 | Better than Std | Present | Present/Strong |
| 7 | FMR1F | FMR1R_9 | 2⅔ | 850 | 2 | | 0.2 | 60 | Comparable or better | Present | Present/Strong |
| 8 | FMR1F | FMR1R_9 | 2⅔ | 850 | 2 | | 0.2 | 64 | Better | Present | Present/Strong |
| 9 | FMR1F | FMR1R | 3⅔ | 500 | 12 | | 2.3 | 64 | Worse | Present | Absent/week |
| 10 | FMR1F | FMR1R | 3⅔ | 650 | 12 | | 1.8 | 64 | Worse | Present | weak |
| 11 | FMR1F | FMR1R | 3⅔ | 1000 | 12 | | 1.2 | 64 | Comparable | Present | Present |
| 12 | FMR1F | FMR1R | 3⅔ | 200 | | 12 | 5.7 | 64 | Comparable | Present | Present |
| 13 | FMR1F | FMR1R_10 | 2 | 500 | | 12 | 2.3 | 60 | | | |
| 14 | FMR1F | FMR1R | 3⅔ | 500 | | 12 | 2.3 | 64 | | | |
| 15 | FMR1F | FMR1R | 3⅔ | 850 | 6 | | 0.7 | 64 | Comparable or better | Present | Present |
| 16 | FMR1F | FMR1R | 3⅔ | 850 | 2 | | 0.2 | 64 | Comparable or better | Present | Present |
| 17 | FMR1F | FMR1R_7 | 4⅔ | 650 | 12 | | 1.8 | 70 | Comparable or better | Present | Present |
| 17 | FMR1F | FMR1R_7 | 4⅔ | 1000 | 12 | | 1.2 | 67 | Comparable or better | Present | Present |
| 19 | FMR1F | FMR1R_7 | 4⅔ | 200 | 0 | | 0.0 | 64 | Worse | Present | Absent/weak |
| 20 | FMR1F | FMR1R_8 | 5⅔ | 500 | 12 | | 2.3 | 64 | Worse | Present | Absent/weak |
| 21 | FMR1F | FMR1R_8 | 5⅔ | 200 | 0 | | 0.0 | 64 | Worse | Present | Absent/weak |

FMR1R_8, FMR1R_9, and FMR1R_10 using genomic DNA isolated from a heterozygote female carrier at different annealing temperatures. The amplicons were separated into fractions according to size to have a distinctive pattern of tapering or "stutter". Full mutation alleles (>200 CGG repeats) were determined based on the size separation of the amplicons. A reference assay condition was arbitrarily determined to comprise 1× PCR buffer; 2 mM $MgCl_2$; 6% DMSO (Sigma); 1.7× Q solution (Qiagen); 0.2 mM each of 7-deaza-2-deoxyGTP, dATP, dCTP, and dTTP; 1 unit of Roche

EXAMPLE 6

Assessment of the Robustness of the Assay to Detect CGG Repeats

To assess the robustness of the PCR assay of Example 2, previously genotyped DNA samples were tested using primers FMR1F and FMR1R, M13R in presence of 7-deaza-dGTP. The person performing the test was blinded to the status of CGG repeats in this panel, and the results scored by a second person. The panel of anonymized forty-seven samples contained homozygous females (N=3), normal heterozygous females (N=1), intermediate female (N=1), pre-mutation females (N=4), and full mutation females (N=11), in addition to intermediate male (N=1), premutation male (N=2), and full mutation males (N=24) (Table 2) The panel assembled was heavy on full mutation carrier males and females. All the samples were identified correctly showing the capability of the new method in identifying presence of full mutations, and distinguishing them from normal homozygous females, or normal heterozygous females with two close alleles (samples H2, 28/29).

EXAMPLE 7

Detection of Mosaics

Figure 5:
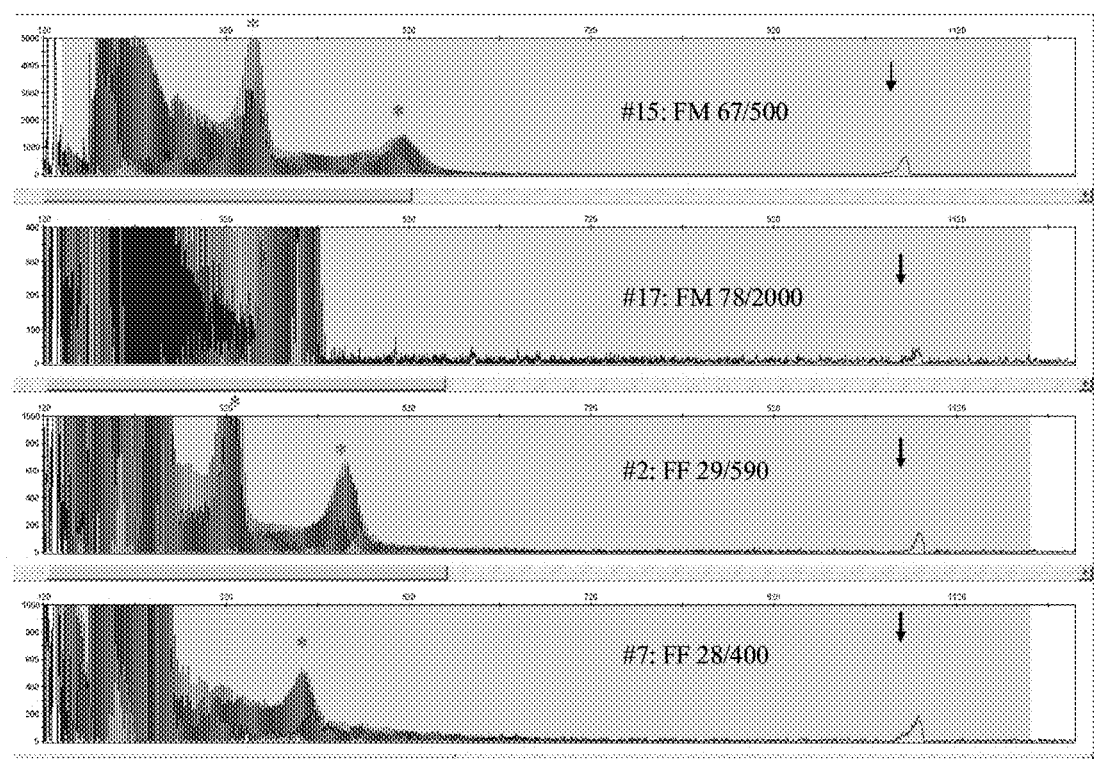
FIG. 5 is an electropherogram showing exemplary amplification results of the CGG repeat tract of 5'-UTR of FMR1 gene in mosaic males and females using primers FMR1F and FMR1R and M13R in presence of 7-deaza-dGTP. Samples 15, 17 from male patients, and samples 2 and 7 from female patients (identified in Table 4) have mosaic premutation and full mutations as shown. Sample 17 shows weak signal for full mutation. Other samples show robust stutter with pre- and full mutation amplification. Premutations are marked by an asterisk while mutations are marked by an arrow.

The ability to detect in a patient blood sample mosaic alleles of premutation and full mutations identified were tested using the PCR assay discussed in Example 2. FIG. 4 shows the results of a mosaic male with a premutation allele of 105 repeats and a full mutation allele of 350, identified from a blood sample. Mosaic samples listed in Table 2 with mosaic full mutations including two male samples (samples 15, 17) and two female samples (samples 2, 7) were tested. Sample 17, which was mosaic for 78 and 2000 repeats showed amplification signal for the longest full mutation (FIG. 5). The signal for the full mutation was weak but detectable. Previous Southern blot analysis of this sample showed the unmethylated premutation allele accounted for 60% of alleles while the methylated full mutation 2000 repeat allele accounted for the rest in this affected male sample. The method also detected mosaic premutations in full mutation carrier females (FIG. 5). These results show that the new PCR method is able to detect mosaic alleles in both males and females.

EXAMPLE 8

Assay Sensitivity

Figure 6A:
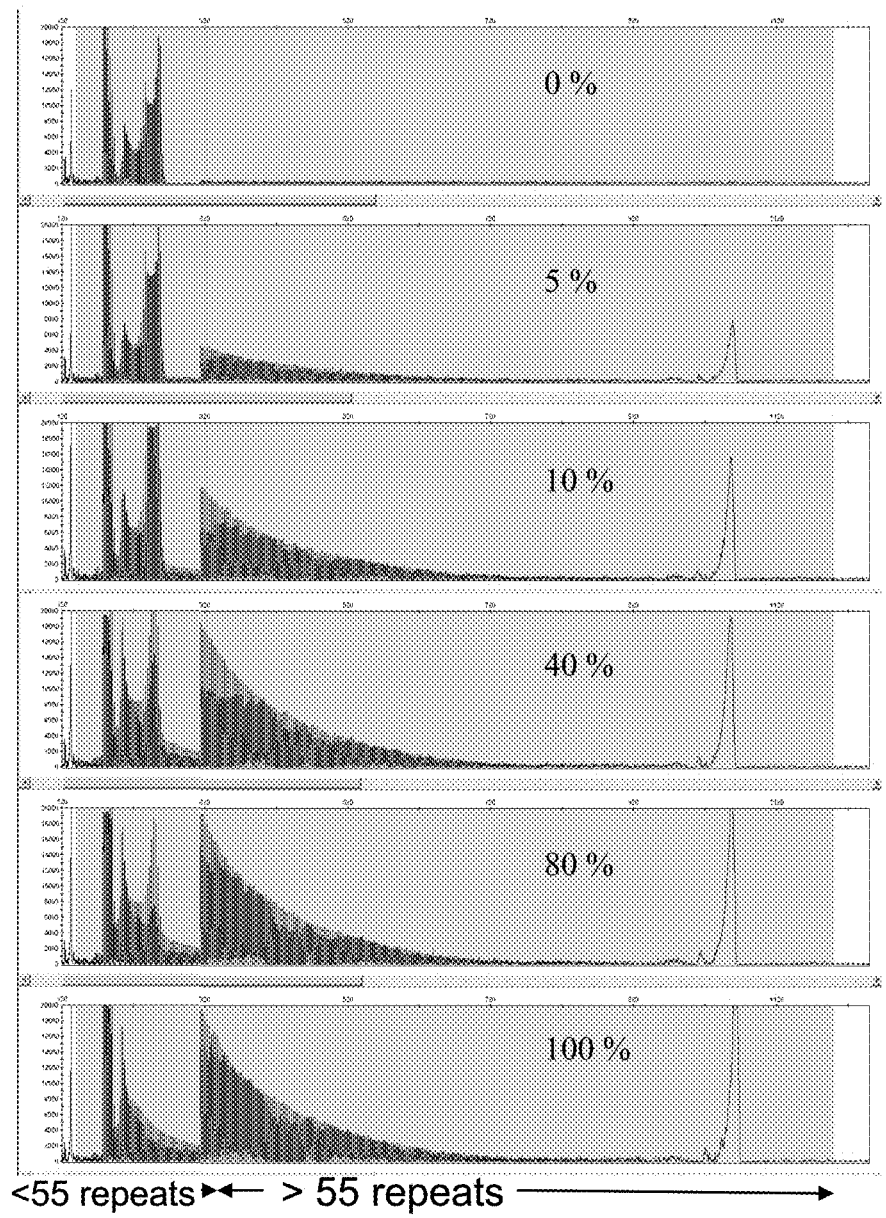

Assay sensitivity was tested by mixing DNA samples from males and females with normal of full mutations creating artificial mosaics. Three DNA sets were prepared using archived, previously genotyped samples, each set harboring two DNA samples mixed at different ratios; set "A" contained DNA samples from two males, one from a normal male with 28 CGG repeats, and one from affected male with 850 CGG repeats; set "B" contained two different male DNAs, a normal male (28 CGG repeats) and affected male (853 CGG repeats), and set "C" contained two female samples, a normal (28/28 repeats) and an affected female (19/450 repeats). FIG. 6 shows the results from detecting these samples. For male DNA, the full mutation was detectable at levels of 5% in set "A" and 10% in set "C". As shown in FIG. 6, the intensity of the stutter amplification and the full mutation signals increase as the level of full mutation increases. In set "B", from mixed male samples, it is interesting to note the ability of the assay to detect as low as 11% mosaic full mutation content in female DNA that contained alleles of three lengths (19, 28, and 450 repeats), where the smaller, normal alleles would have been favored during PCR. At 10% mosaic content, a weak signal from a full mutation is present (FIG. 6C), while stutter amplification is appearing reliably at 20% content of the full mutation. On average, full mutation expansion could be detected by both the stutter amplification and full mutation signal detection, at levels as low as 5% to 10% in both males and females.

EXAMPLE 9

Concordance Study

The assay results of new PCR method were compared against the existing assay method which is composed of a two step-process: a PCR incorporating gender marker, and a subsequent Southern blot analysis for any sample with an expansion length of 45 repeats or above, as well as any apparent homozygous females. Previously genotyped 1,275 whole blood samples were analyzed using the new PCR mix including PCR primers FMR1F and FMR1R, M13R and 7-deaza dGTP; the results indicated 100% concordance with the existing method. As shown in Table 9, of these 1,275 samples a total of six patient samples (three female, three male) harbored full mutations.

TABLE 9

Concordance of Triplet-Primed PCR/Capillary Electrophoresis Method with Existing PCR/Southern Blot Method for Determination of FMR1 Trinucleotide Expansion Status

| Classification | Number |
| --- | --- |
| Normal (HF, HetF, NM) | 1237 |
| Intermediate Female | 15 |
| Intermediate Male | 7 |
| Premutation Female | 10 |
| Premutation Male | 0 |
| Full Mutation Female | 3 |
| Full Mutation Male | 3 |

HF, normal homozygous female;
HetF, normal heterozygous female;
NM, normal male.

EXAMPLE 10

Detection from Blood Spots and Saliva

Figure 7:
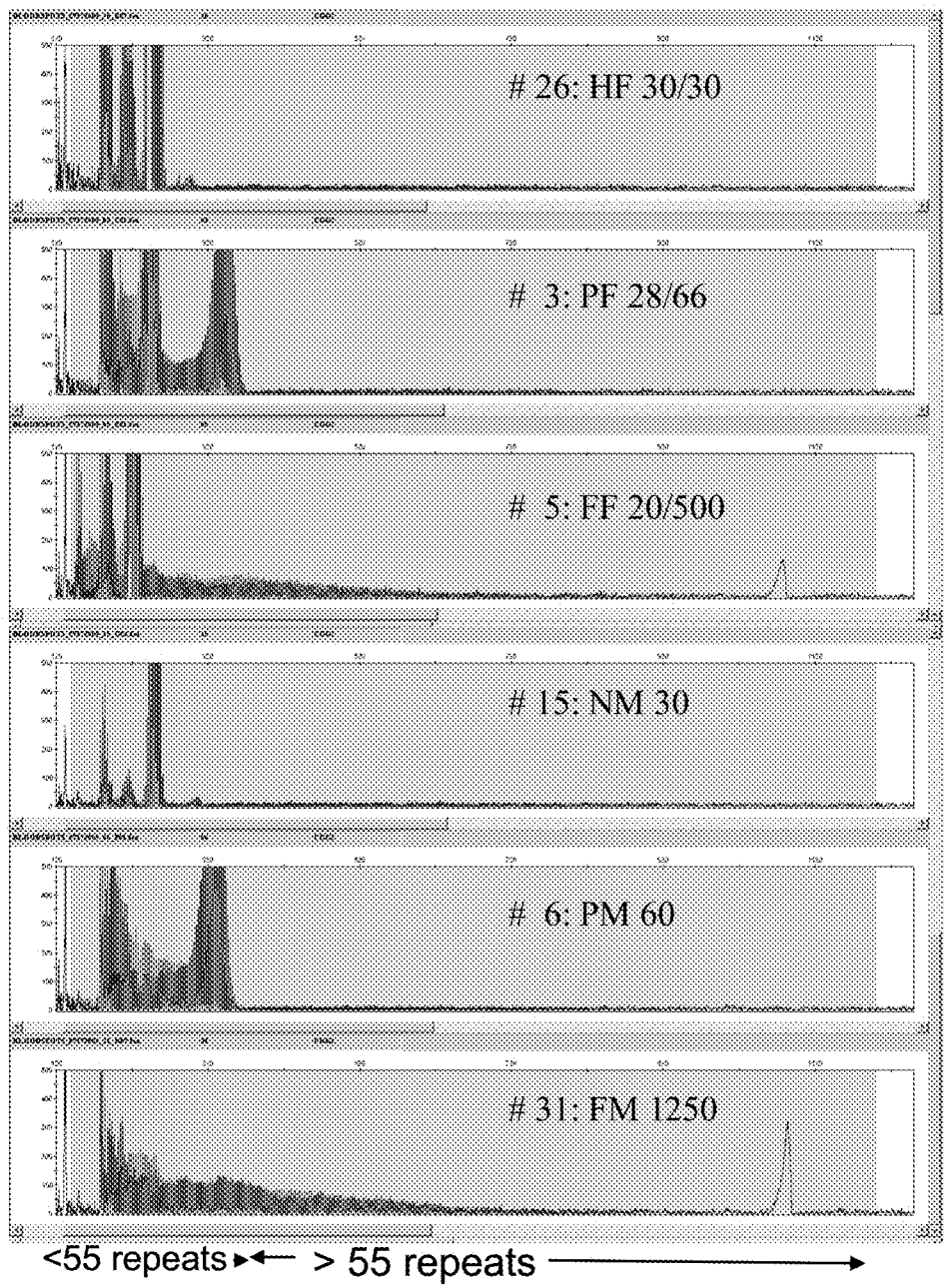
FIG. 7 is an electropherogram showing the results for detection of normal, premutation and full mutation carriers in the 5'-UTR of FMR1 gene from blood spots. Blood samples were spotted on filter cards, and punched using BSD1000 GenePunch. DNA from two spots was extracted and PCR was performed using primers FMR1F and FMR1R and M13R in presence of 7-deaza-dGTP. The number in each panel corresponds to the patient numbers in Table 5. The mutation status and CCG repeat allele content for each sample is also shown. The method can identify full mutations and distinguish normal females, including homozygous females, from carrier females.
Figure 8:
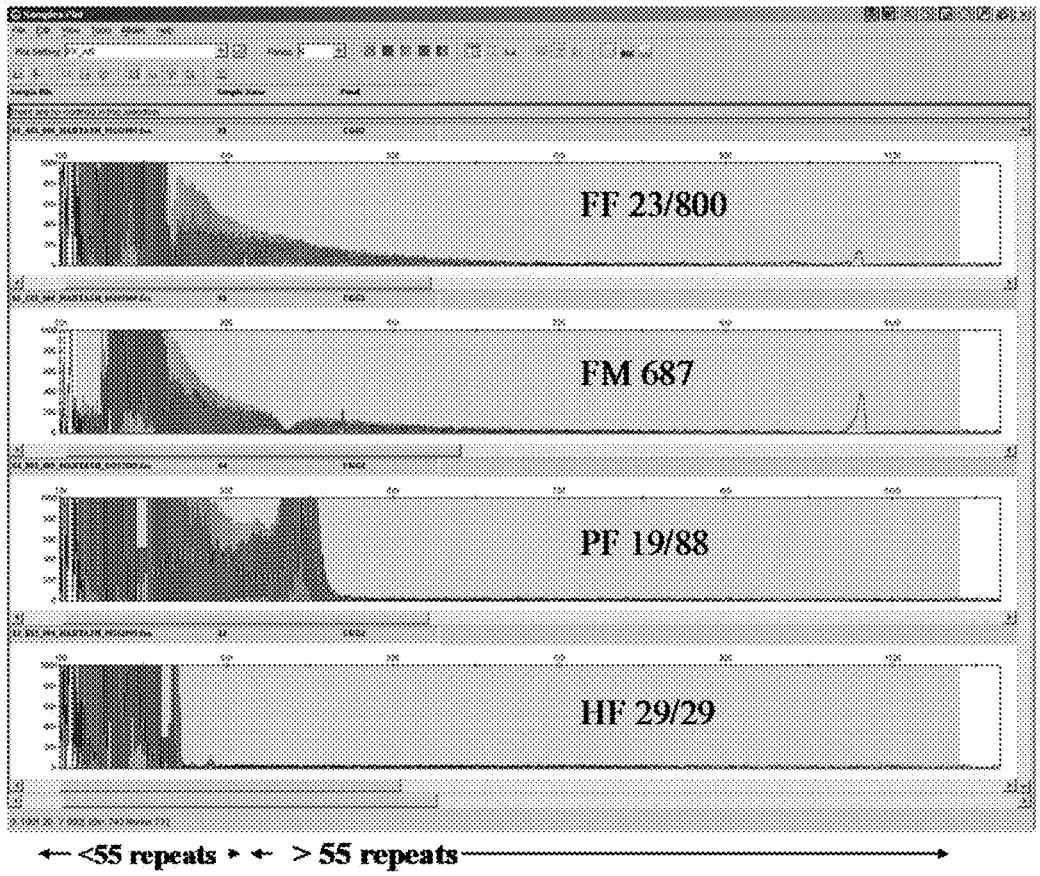
FIG. 8 is an electropherogram showing the results of amplification of the 5'-UTR of FMR1 gene using reverse primer FMR1R (SEQ ID NO: 3), forward primer FMR1F, and M13R in presence of 7-deaza-dGTP.
Figure 9:
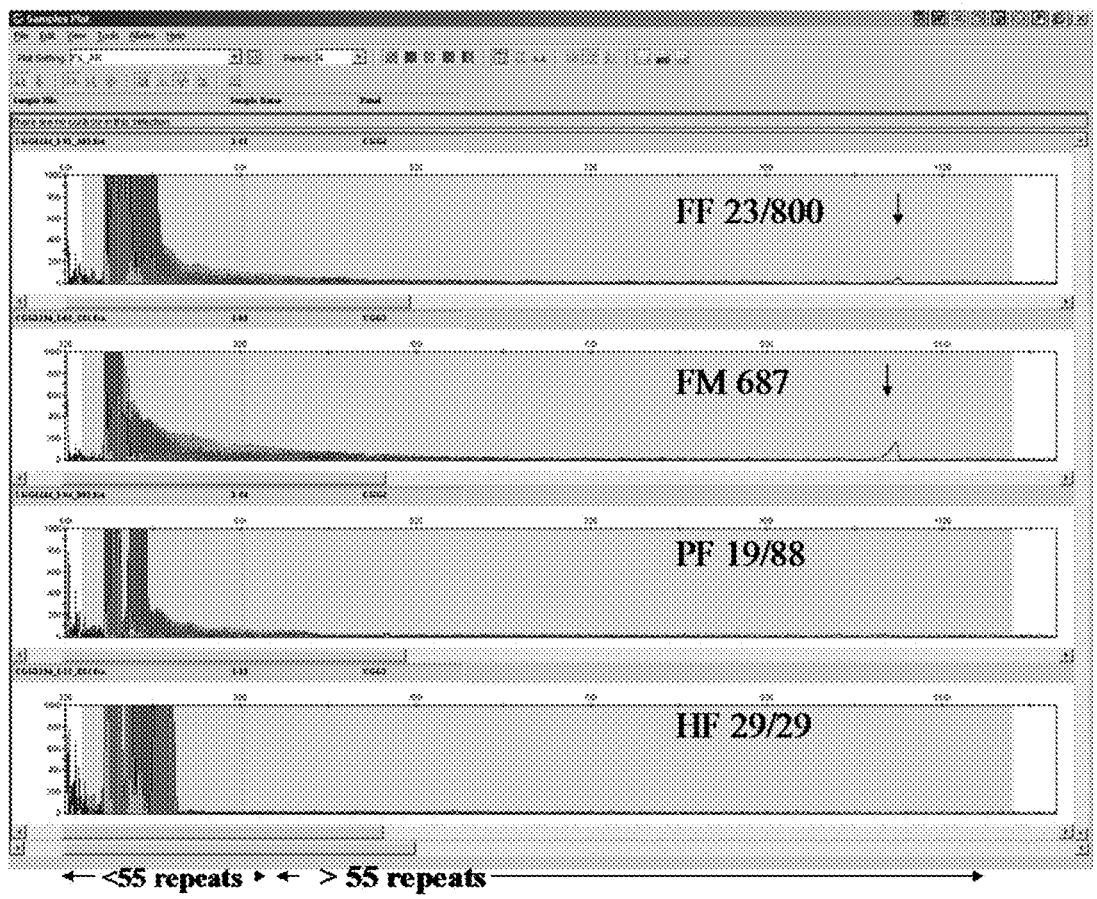
FIG. 9 is an electropherogram showing the results of amplification of the 5'-UTR of FMR1 gene using reverse primer CGG1 (SEQ ID NO: 5), forward primer FMR1F, and M13R in presence of 7-deaza-dGTP. The samples used in the assay are the same as in FIG. 8. The mutation status and CCG repeat allele content are shown.
Figure 10:
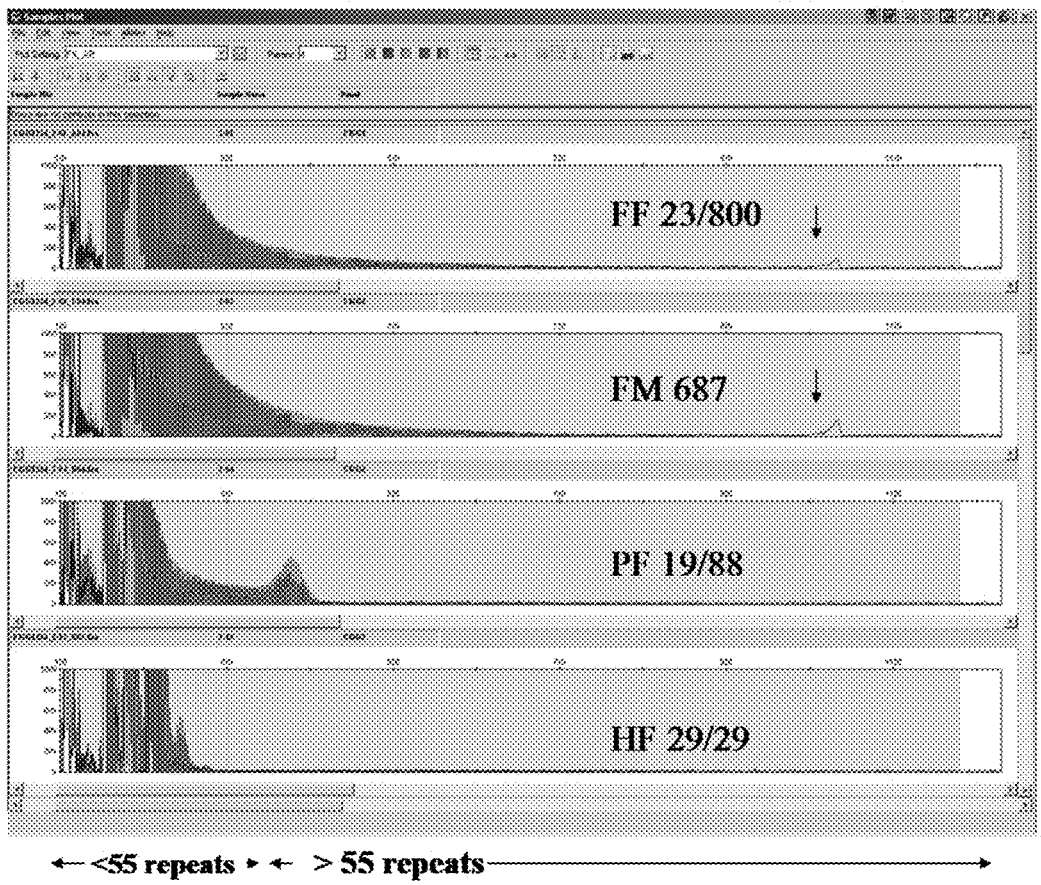
FIG. 10 is an electropherogram showing the results of amplification of the 5'-UTR of FMR1 gene using reverse primer CGG2 (SEQ ID NO: 6), forward primer FMR1F, and M13R in presence of 7-deaza-dGTP. The samples used in the assay are the same as in FIG. 8. The mutation status and CCG repeat allele content are shown.
Figure 11:
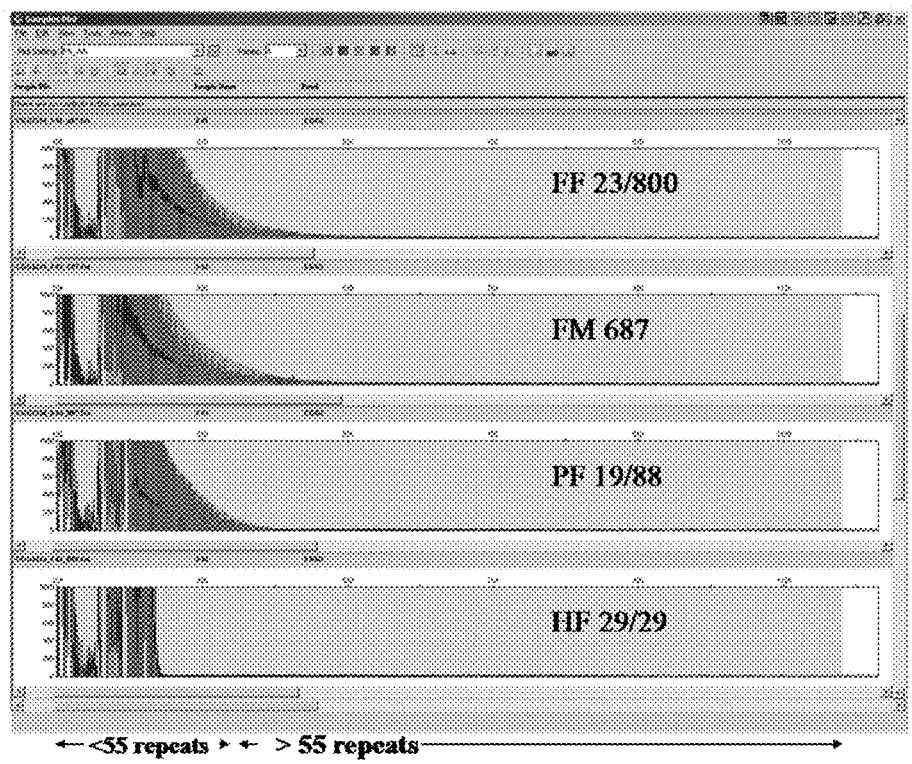
FIG. 11 is an electropherogram showing the results of amplification of the 5'-UTR of FMR1 gene using reverse primer CGG3 (SEQ ID NO: 7), forward primer FMR1F, and M13R in presence of 7-deaza-dGTP. The samples used in the assay are the same as in FIG. 8. The mutation status and CCG repeat allele content are shown.
Figure 12:
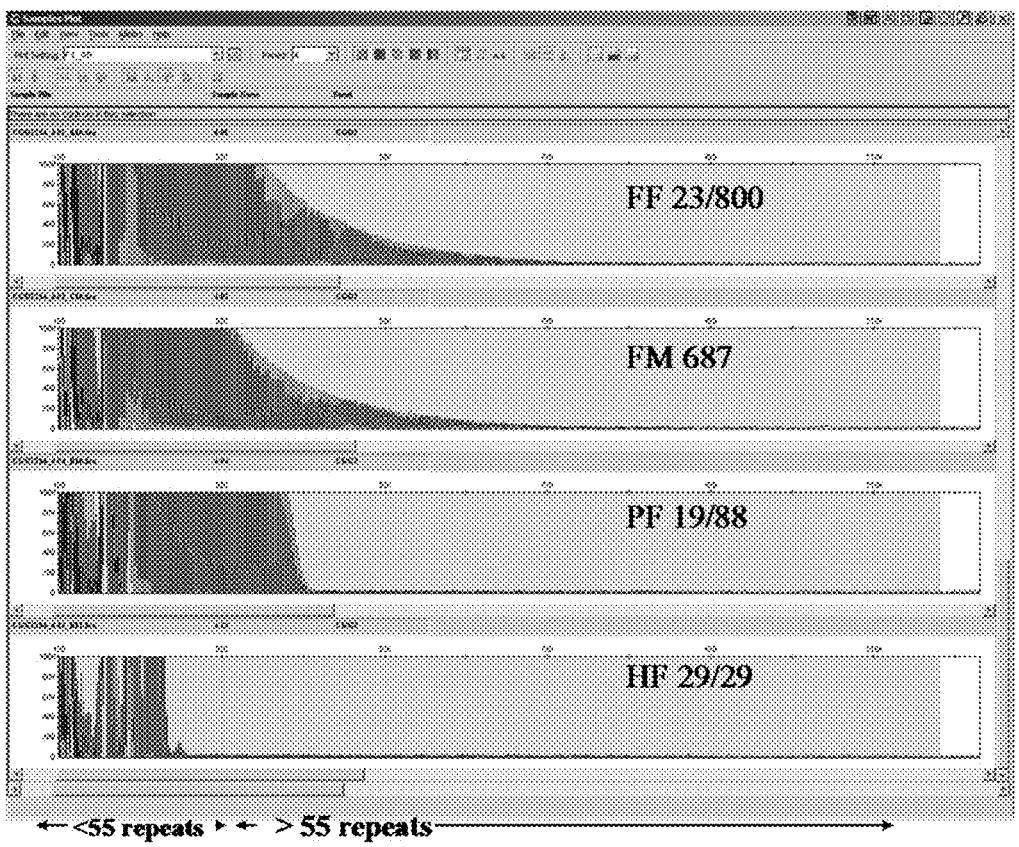
FIG. 12 is an electropherogram showing the results of amplification of the 5'-UTR of FMR1 gene using reverse primer CGG4 (SEQ ID NO: 8), forward primer FMR1F, and M13R in presence of 7-deaza-dGTP. The samples used in the assay are the same as in FIG. 8. The mutation status and CCG repeat allele content are shown.
Figure 13:
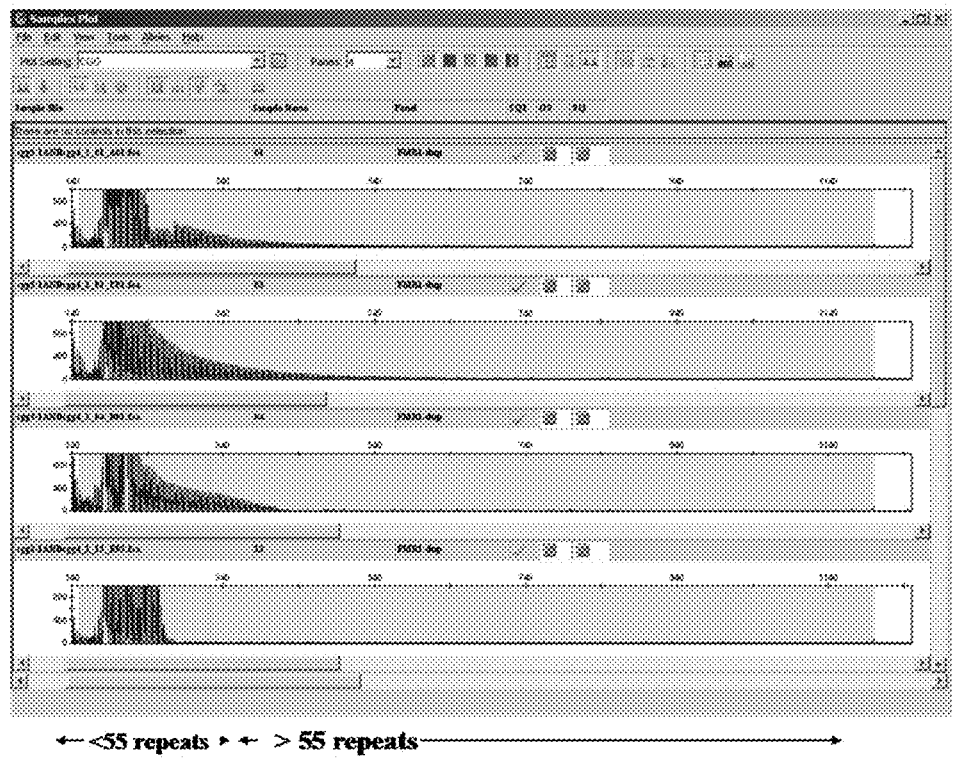
FIG. 13 is an electropherogram showing the results of amplification of the 5'-UTR of FMR1 gene using reverse primer CGG3-1 (SEQ ID NO: 9), forward primer FMR1F, and M13R in presence of 7-deaza-dGTP. The samples used in the assay are the same as in FIG. 8.
Figure 14:
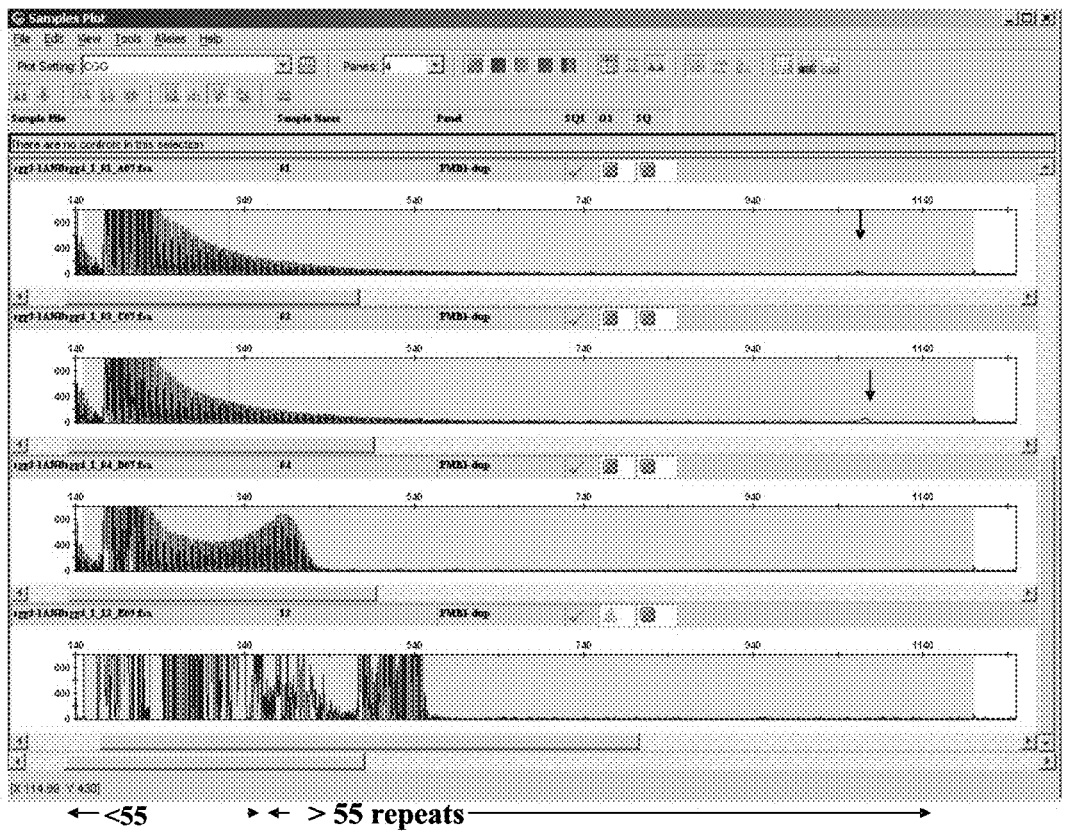
FIG. 14 is an electropherogram showing the results of amplification of the 5'-UTR of FMR1 gene using reverse primer CGG 4-1 (Nucleotides 1-36 of SEQ ID NO: 10), forward primer FMR1F, and M13R in presence of 7-deaza-dGTP. The samples used in the assay are the same as in FIG. 8.

The CGG repeat-primed PCR assay was tested for the detection of CGG repeats in FMR1 gene from blood spots, since newborn screening programs rely on blood spotted on Guthrie cards. Residual blood from previously genotyped patients were spotted on Guthrie cards. Blood spots were punched from each card using BSD1000 GenePunch Instrument to generate two punches (3.2 mm each) per patient and DNA was extracted using Qiagen BioSprint reagents. DNA from blood spots was analyzed by the new PCR method. A total of 37 samples containing the different FMR1 CGG expansions in males and females were tested (Table 5). Of the 37 samples, fourteen samples had intermediate repeats, nine samples had pre-mutations, and four samples had full mutations (as determined by Southern blot analysis): one female (20/500 repeats) and three males (300-700; 1250; 1250). FIG. 7 shows an example of the results obtained. All the samples where genotyped correctly by the new qualitative method as harboring normal, intermediate, pre-mutation or full mutations.

EXAMPLE 11

Estimation of Premutation Carrier Frequency in US Population

A total of 13770 genomic DNA samples were analyzed by CCG repeat-primed PCR assay for the presence of premutations and/or full mutation. The DNA samples were obtained from individual samples submitted for CF screening and screening diseases prevalent among Ashkenazi Jews. The PCR reaction mixture comprised 1× reaction buffer, $MgCl_2$ at final concentration of 2 mM, 1 unit of FastStarTaq polymerase (all from Roche Applied Science, Indianapolis, Ind.), 0.6 µM each of FMR1F, FMR1R and M13R primers, 0.2 µM each of the nucleotidesddATP, dCTP, dTTP and 7-deaza-2-deoxy GTP, 1.7× Q solution (Qiagen, Carlsbad, Calif.) and 6% DMSO (Sigma, St. Louis, Mo.). The PCR reaction products were separated on ABI 3730 DNA Analyzer (Applied Biosystems, Carlsbad, Calif.) and analyzed using GeneMapper Software (Applied Biosystems, Carlsbad, Calif.) as described above. Samples showing fragments containing ~50 or more CGG repeats were further analyzed using the Capillary Southern Assay (CSA) was described by Strom et al. (Genet Med. 2007; 9(4):199-207) (see also US 20080124709 by Strom et al.). The method includes a multiplex PCR assay together with capillary electrophoresis (CE) and Southern blot to determine the gender of the individual, the size of the CE fractions which is indicative of CGG repeat expansion.

Figure 18A:
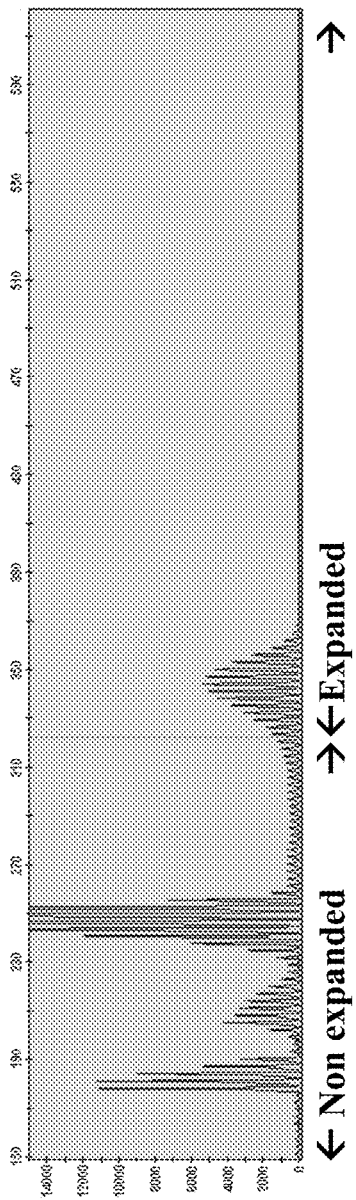
FIGS. 18A-B show exemplary results of an CCG repeat-primed PCR assay and subsequent confirmation by Capillary Southern Analysis (CSA) for the detection of CGG repeats in the 5'-UTR of FMR1 gene.
Figure 18B:
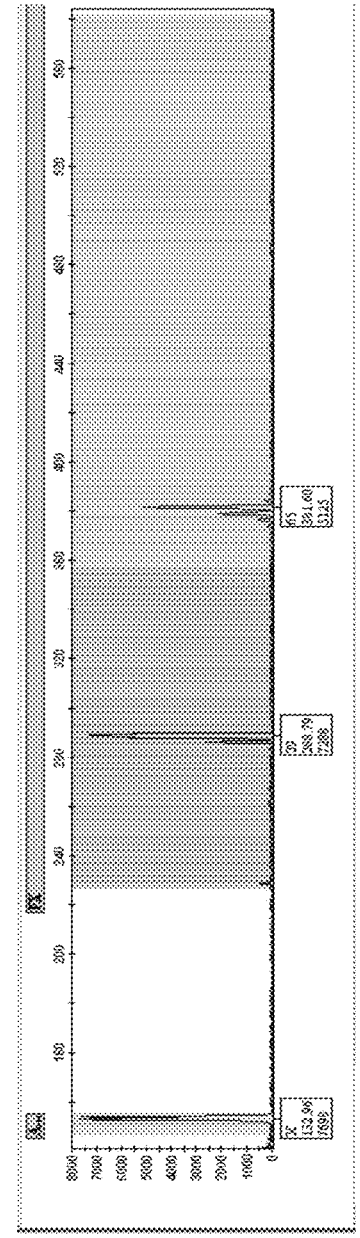

FIG. 18A provides an example of the results obtained for a CCG repeat-primed PCR assay. The sample was identified as harboring a non expanded allele (<55 repeats, indicated) and an expanded allele (>CGG 55 repeats, indicated). The sample was reanalyzed using CSA method with gender confirmation. As shown in FIG. 18B, the sample was confirmed to be from a female as only the X-chromosome copy of the Amelogenin gene was amplified. The sample showed heterozygosity for 29 and 65 repeats.

Figure 19:
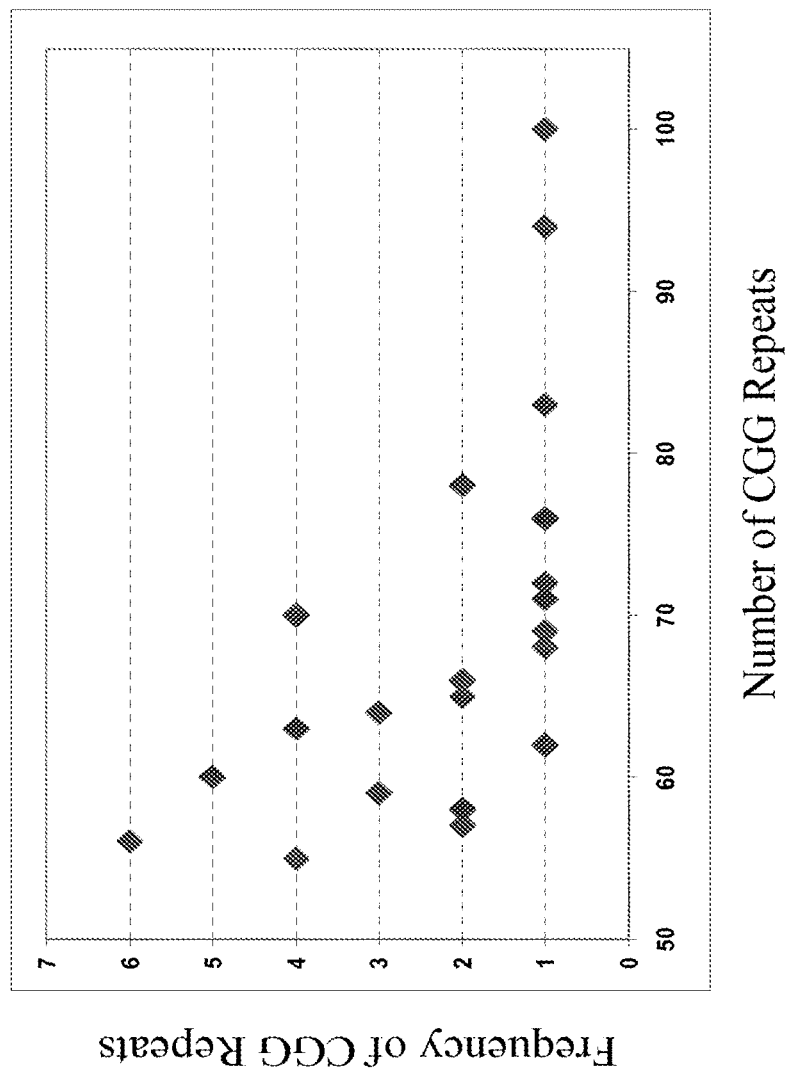
FIG. 19 shows the distribution of the 48 premutation alleles of the FMR1 gene identified in DNA samples submitted for Cystic Fibrosis screening.

A total of 11759 samples from CF-screened females were analyzed as a representative of the US population. Forty eight premutations (>55 CGG repeats) were identified from the CF-screened samples showing a premutation carrier frequency of 1:245. The distribution of the 48 premutation alleles identified is shown in FIG. 19. Twelve of the 48 alleles (25%) harbored ≥70 CGG repeats.

Figure 20B:
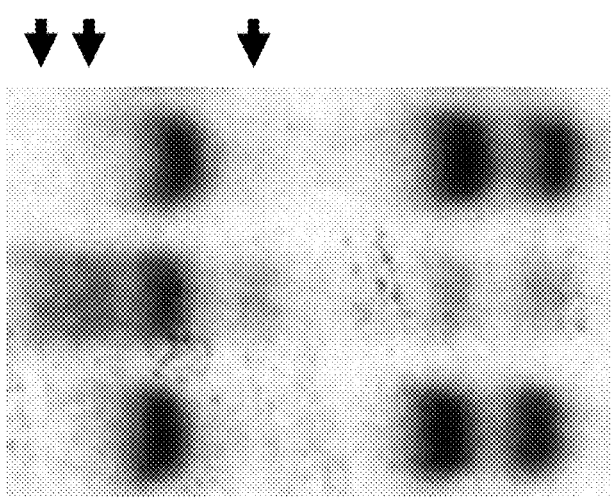
FIGS. 20A-B show the identification of a full mutation allele (>200 CGG repeats) of the FMR1 gene in a sample obtained from a Caucasian female.
Figure 20A:
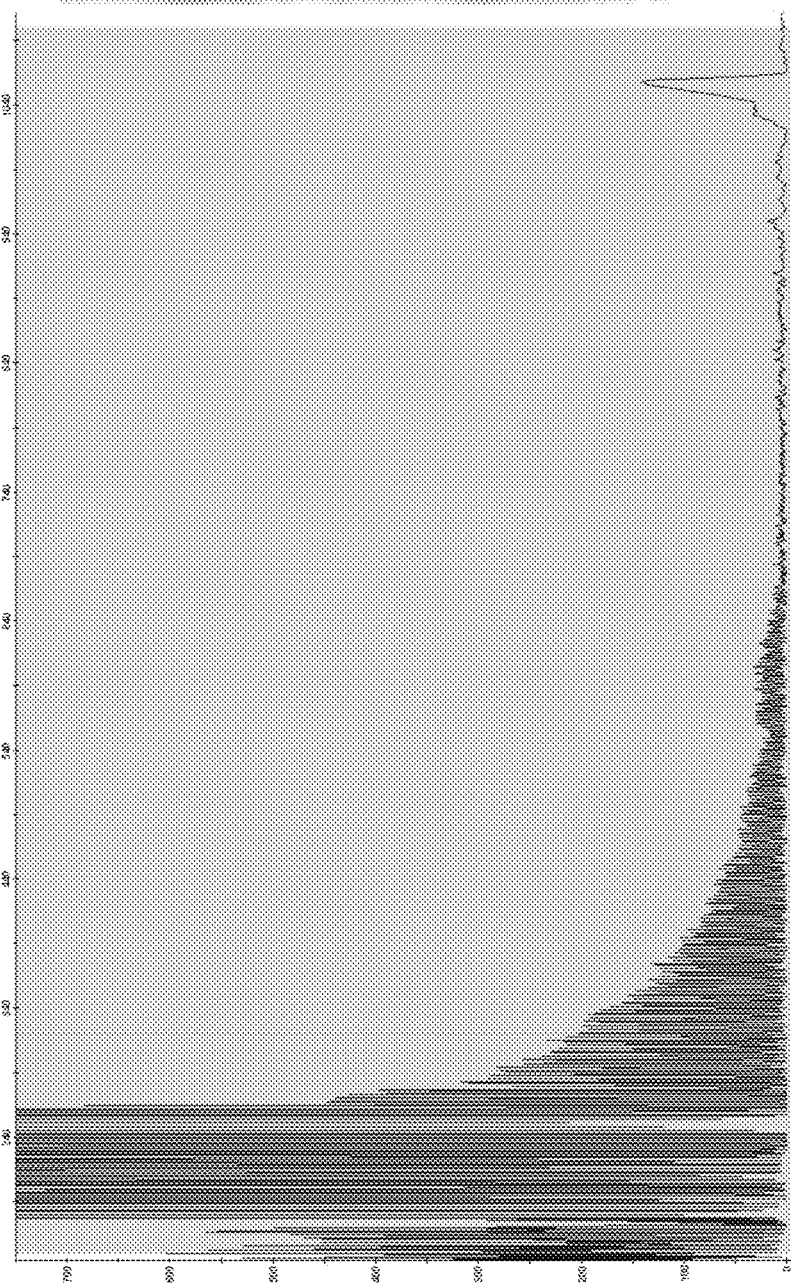

One female sample from a Caucasian patient showed evidence of full mutation as shown by stutter pattern of amplification and detection of the late migrating fragment on capillary electrophoresis (FIG. 20A). That sample was further analyzed by Capillary Southern Assay and was shown to harbor 30/(400-800) repeats, confirming the finding of CCG triplet primed PCR. The methylation status of the DNA sample was analyzed by digestion with EcoRI and XhoI restriction endonuclease followed by agarose gel electrophoresis. The sample showed the appearance of additional DNA fragments (indicated by arrow) along with the expected sizes indicating heterogeneity in DNA methylation (FIG. 20B).

The distribution of premutation carrier frequency among different US sub population or ethnic groups were estimated by analyzing a total of 13770 samples including DNA samples submitted for Cystic Fibrosis (CF) carrier screening and samples submitted for screening for diseases more prevalent in Ashkenazi Jews. Premutation carrier frequency in females was estimated from the experimental results of the CCG primed PCR assay and the premutation carrier frequencies in males were calculated from the estimated premuation carrier frequency in females.

Premutation carrier frequency in males can be calculated using the equation:

Premutation carrier frequency in males=premutation carrier frequency in females X (1-S)×0.5 where S is the rate of expansion of a premutation into a full mutation and was calculated to be 0.107 (i.e. ~10.7% of premutations expand to full mutations), while 0.5 is the probability of inheriting either allele.

A total of 63 premutations were identified among the 13770 samples resulting in a premutation carrier frequency of 1:219. This frequency is higher due the over representation of the samples from Ashkenazi Jews. Therefore, taking the CF-screened population as approximate representative of the US population, the premutation carrier frequency was found to be 1:245 (48 premutation samples identified out of 11759 CF-screened females). Table 10 shows the results from the various self-identified ethnic groups within CF population samples tested. Premutation carrier frequency among 2866 Caucasians was 1:169, while it was 1:287 in 1723 Hispanics. No premutations were identified in Asians, while the frequency in African American was 1:124. In Ashkenazi Jewish samples, 15 premutations were detected from 2011 DNA samples with a premutation carrier frequency of 1:134. Only one tested sample from Ashkenazi Jews harbored a premutation ≥70 CGG repeats (80 repeats).

TABLE 10

Distribution of premutation carrier frequency in different US subpopulation

| Ethnicity | # Samples Screened | # Premutations Identified | Frequency |
| --- | --- | --- | --- |
| Caucasian | 2866 | 17 | 1:169 |
| Hispanic | 1723 | 6 | 1:287 |
| African American/Black | 247 | 2 | 1:124 |
| Ashkenazi Jewish | 2011 | 15 | 1:134 |
| Asian | 254 | 0 | N/A |
| Other | 674 | 2 | 1:337 |
| Not Given | 5995 | 21 | 1:285 |
| Total | 13770 | 63 | 1:219 |

The results were analyzed using Fisher Exact test and differences between various groups did not reach statistical significance using two-tailed P values and shown in Table 11 below. The number of African American and Asians analyzed in the study were low to make any definite conclusion regarding frequency of premutation, the lack of detection of premutations in self-identified Asians is consistent with published reports (Otsuka et al. Brain Dev. 2010; 32(2): 110-114; Tzeng et al. Am. J. Med. Genet. A 2005; 133A: 37-43).

TABLE 11

Statistical analysis of differences in premutation frequencies in various subpopulation two tailed P values

| | Caucasian | Hispanic | African American/Black | AJ | Asian |
| --- | --- | --- | --- | --- | --- |
| Caucasian | | >0.2 | >0.5 | >0.5 | >0.2 |
| Hispanic | | | >0.2 | >0.1 | >0.2 |
| African American/Black | | | | >0.5 | >0.2 |
| AJ | | | | | >0.1 |
| Asian | | | | | |

To provide for a better approximation of the permutation carrier frequency in US subpopulation or ethnic group, the permutation carrier frequency in each ethnic group in the study was calculated, the data was then extrapolated using the US Census Bureau and approximate Census numbers. Table 12 shows the approximation of permutation carrier frequencies in US subpopulation or ethnic groups based on US Census Bureau data. The permutation carrier frequency in US females is estimated to be 1:177 and that for US males to be 1:396. This calculated frequency may be revised once better information obtained from African Americans and Asians is taken into account.

TABLE 12

Estimated distribution of permutation carrier frequency in different US subpopulation or ethnic group based on US Census Bureau data

| Ethnicity | % of US population[1] | Premutation Carrier Frequency | Estimated Number of females in the U.S. Population[1] | Number of premutation Carriers |
|---|---|---|---|---|
| Caucasians[2] | 65.6 | 1:169 | 98,759,970[3] | 584,379 |
| Hispanic/Latino | 15.4 | 1:287 | 23,875,899 | 83,191 |
| Black of African-American | 12.8 | 1:124 | 19,844,903 | 160,040 |
| Asian | 4.5 | 1:1500[3] | 6,976,724 | 4,651 |
| Ashkenazi Jewish | 2.2 | 1:134 | 2,945,160[3] | 21,979 |
| Total | | | 152,402,657 | 854,239 |
| U.S. Female premutation carrier frequency | | | | 1:178 |
| U.S. Male premutation carrier frequency[4] | | | =1/178 × (1-0.107) × 0.5 | 1:400 |
| Full mutation frequency in the U.S. population[4] | | | =1/178 × 0.107 × 0.5 | 1:3335 |

[1]Information from U.S. Census Bureau: State and County QuickFacts accessed May 31, 2010 (http://quickfacts.census.gov/qfd/states/00000.html). Numbers may not add to actual total U.S. population due to self identification of two or more ethnicities. Estimates of female numbers assumes females account for 50% of the population.
[2]Caucasians did not include Ashkenazi Jews to better estimate overall carrier frequency.
[3]Rough estimate from published reports from Taiwan and Japan.
[4]Calculated using the equations discussed above.

EXAMPLE 12

Estimation of Full Mutation Frequency in US Population

Full mutation frequency in an individual (male or female) can be calculated based on the premutation carrier frequency of a female and using the following equation:

Full mutation frequency=premutation carrier frequency in females×S×0.5 where S is the rate of expansion of a premutation into a full mutation and was calculated to be 0.107 (i.e. ~10.7% of premutations expand to full mutations), while 0.5 is the probability of inheriting either allele.

The calculated full mutation frequency in the U.S. population (males and females) is 1/177×0.107×0.5=1:3308. In Caucasians, the predicted full mutation carrier frequency is 1:3159 individuals while in Hispanics it is 1:5364, and in Ashkenazi Jews 1:2505.

EXAMPLE 13

Estimation of FXTAS and FXPOI Incidence in US Population

The incidence of FXTAS and FXPOI in a populations was calculated using the following equation:

incidence of FXTAS=premutation carrier frequency in males×$P_{FETAS}$×frequency of alleles ≥70 CGG repeats where $P_{FXTAS}$ is penetrance in patients of larger premutation alleles (≥70 CGG repeats) estimated to be ⅓ (0.33).

The incidence of FXPOI incidence was calculated using the following equation:

incidence of FXPOI=premutation carrier frequency in females×$P_{FXPOI}$×frequency of alleles ≥70 CGG repeats where $P_{FXPOI}$ is the penetrance of large premutation alleles(≥70 CGG repeats) in FXPOI, estimated to be ~20%-28%.

To determine the incidence of FXTAS in US population, the calculated frequency of premutation in males was first determined based on the premutation carrier frequency in females as discussed above. The calculated premutation carrier frequency in males was 1:396. The calculated incidence of FXTAS in the US-screened population was estimated to be 1:4808 males based on the above equation.

For incidence of FXPOI, the penetrance of 20% of larger premutations alleles and frequency of alleles ≥70 CGG repeats were used in the calculation similar to FXTAS. Using this information the calculated incidence of FXPOI in females is 1:3557 in US. This incidence might actually vary if women who suffer from FXPOI were not present in the CF-screened samples.

EXAMPLE 14

Detection of CCG Repeats in the 5'-UTR of FMR2 Gene

The CCG repeats in the FMR2 gene can be amplified by PCR. The PCR reaction will include a fluorescently labeled forward primer and reverse primers comprising CGG triplets such that the reverse primers can anneal to CCG repeat sequence. In one example, the reverse primer may comprise the junction sequence of the 3'-end of the CCG repeat tract and flanking sequence and a portion of the sequence downstream of CCG repeat. The reverse primers having at least two CGG triplets and without such junction sequence will hybridize randomly inside the CCG repeat sequence and initiate DNA synthesis. This will result in a range of amplicons of different sizes (stutter). The reverse primers may further comprise a M13 linker sequence at its 5'-end such that a M13 primer can anneal to this linker sequence and further amplify the amplicons thus generated.

The PCR mix for amplification of all normal, premutation, and full mutations of the CCG repeats may contain 1× PCR buffer; 2 mM $MgCl_2$; 6% DMSO (Sigma); 1.7× Q solution (Qiagen); 0.2 mM each of 7-deaza-2-deoxyGTP, dATP, dCTP, and dTTP; 1 unit of Roche FastStarTaq polymerase; and 0.6 µM each of the forward primer (SEQ ID NO: 76), reverse primer, and M13 reverse linker primer. Several variations of the reverse primers can be tested together with the forward primer. The sequences of the reverse primers are listed in Table 3 above.

Three microliters of genomic DNA (10-150 ng total) may be added for a final PCR reaction volume of 15 µl. The cycling program, can be performed on an ABI 9700 thermal cycler, can be started by incubating the mix at 98° C. for 10 minutes to activate the polymerase, followed by 10 cycles of denaturation at 97° C. for 35 sec, annealing at 64° C. for 2 minutes, and extension at 68° C. for 8 minutes, followed by 25 cycles of denaturation at 97° C. for 35 sec, annealing at 64° C. for 2 minutes, and extension at 68° C. for 8 min 20 sec (with 20 sec extension each additional cycle). For all 35 cycles, the ramp rate can be adjusted to 64% for the denaturation and extension steps (ramping up at 0.5° C.), and to 25% for the annealing step (ramping down at 0.5° C.). Two microliters of the PCR product (some times diluted 1:5 in $H_2O$) may be mixed with HiDi Formamide and Map marker-1000 size standard (Bioventures Inc., Murfreesboro, Tenn.) and samples can be injected on an ABI 3730 DNA Analyzer equipped with a 36-cm capillary loaded with Pop-7 polymer (Applied Biosystems) at 3 volts for 7 seconds. Data can be analyzed using GeneMapper software (Applied Biosystems).

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A primer pair for amplifying all or a portion of a CGG repeat tract in the 5'-untranslated region (5'-UTR) of fragile X related mental retardation gene 1 (FMR1), comprising an upstream primer and a downstream primer wherein: (i) the downstream primer comprises a CCG repeat segment which contains less than four consecutive CCG triplet repeats and hybridizes to the junction between the 3' end of the CGG repeat tract in the FMR1 gene and sequence directly 3' thereto or hybridizes to a region in the CGG repeat tract in the FMR1 gene, wherein the downstream primer consists of a sequence selected from the group consisting of SEQ ID NOs: 3-6 and 14-40; and (ii) the upstream primer comprises a CGG repeat segment which contains less than four consecutive CGG triplet repeats and hybridizes to the junction between the 5' end of the CGG repeat tract in the FMR1 gene and sequence directly 5' thereto or hybridizes to a region in the CGG repeat tract in the FMR1 gene, wherein the upstream primer consists of a sequence selected from the group consisting of SEQ ID NOs: 2, 41-69, 73, and 74, wherein said downstream primer and/or said upstream primer is detectably labeled with a fluorophore or a radio-label.

2. The primer pair of claim 1, wherein said downstream primer comprises a second nucleic acid sequence with no sequence homology to said FMR1 gene, said second nucleic acid sequence located 5' to said CCG triplet repeat sequence and said upstream primer comprises additional nucleic acid sequence with no sequence homology to said FMR1 gene, said additional nucleic acid sequence located 5' to said CGG repeat sequence.

3. The primer pair of claim 1, wherein said downstream primer further comprises a second nucleic acid sequence 5' to said CCG triplet repeat sequence, said second nucleic acid sequence comprising sequence adjacent to the 3' end of the CGG repeat tract in the FMR1 gene and said upstream primer further comprises a first additional nucleic acid sequence 5' to said CGG repeat sequence, said first additional nucleic acid sequence comprising sequence adjacent to the 5' end of the CGG repeat tract in said FMR1 gene.

4. The primer pair of claim 1, wherein said downstream primer comprises two sets of two consecutive CGG triplets separated from each other by at least one nucleotide or said upstream primer comprises two sets of two consecutive CCG triplets separated from each other by at least one nucleotide.

5. The primer pair of claim 1, wherein said downstream primer consists of a sequence selected from the group consisting of SEQ ID NOs: 15-22 and 29-36 or wherein said upstream primer consists of a sequence selected from the group consisting of SEQ ID NOs: 42-49 and 56-66.

* * * * *